(12) United States Patent
Kawaoka et al.

(10) Patent No.: US 9,926,535 B2
(45) Date of Patent: *Mar. 27, 2018

(54) HIGH TITER RECOMBINANT INFLUENZA VIRUSES FOR VACCINES

(71) Applicant: Wisconsin Alumni Research Foundation (WARF), Madison, WI (US)

(72) Inventors: Yoshihiro Kawaoka, Middleton, WI (US); Taisuke Horimoto, Bankyotan (JP); Shin Murakami, Mito (JP)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/000,851

(22) Filed: Jan. 19, 2016

(65) Prior Publication Data

US 2016/0208223 A1    Jul. 21, 2016

Related U.S. Application Data

(63) Continuation of application No. 11/729,557, filed on Mar. 29, 2007, now Pat. No. 9,254,318.

(60) Provisional application No. 60/787,766, filed on Mar. 31, 2006.

(51) Int. Cl.
| | |
|---|---|
| *C12N 7/00* | (2006.01) |
| *A61K 39/145* | (2006.01) |
| *C12N 15/85* | (2006.01) |
| *A61K 39/12* | (2006.01) |
| *C07K 14/005* | (2006.01) |
| *C12N 9/24* | (2006.01) |
| *A61K 39/00* | (2006.01) |

(52) U.S. Cl.
CPC ............ *C12N 7/00* (2013.01); *A61K 39/12* (2013.01); *A61K 39/145* (2013.01); *C07K 14/005* (2013.01); *C12N 9/2402* (2013.01); *C12N 15/85* (2013.01); *A61K 2039/525* (2013.01); *A61K 2039/5254* (2013.01); *C12N 2760/16051* (2013.01); *C12N 2760/16121* (2013.01); *C12N 2760/16134* (2013.01); *C12N 2760/16151* (2013.01); *C12N 2800/107* (2013.01); *C12Y 302/01018* (2013.01)

(58) Field of Classification Search
None
See application file for complete search history.

(56) References Cited

U.S. PATENT DOCUMENTS

| | | | |
|---|---|---|---|
| 4,071,618 A | 1/1978 | Konobe et al. | |
| 4,659,569 A | 4/1987 | Mitsuhashi et al. | |
| 5,166,057 A | 11/1992 | Palese et al. | |
| 5,716,821 A | 2/1998 | Wertz et al. | |
| 5,789,229 A | 8/1998 | Wertz et al. | |
| 5,820,871 A | 10/1998 | Palese et al. | |
| 5,840,520 A | 11/1998 | Clarke et al. | |
| 5,854,037 A | 12/1998 | Palese et al. | |
| 5,948,410 A | 9/1999 | Van Scharrenburg et al. | |
| 5,994,526 A | 11/1999 | Meulewaeter et al. | |
| 6,033,886 A | 3/2000 | Conzelmann | |
| 6,037,348 A | 3/2000 | Colacino et al. | |
| 6,146,642 A | 11/2000 | Garcia-Sastre et al. | |
| 6,194,546 B1 | 2/2001 | Newton et al. | |
| 6,455,298 B1 | 9/2002 | Groner et al. | |
| 6,544,785 B1 | 4/2003 | Palese et al. | |
| 6,656,720 B2 | 12/2003 | Groner et al. | |
| 6,825,036 B2 | 11/2004 | Makizumi et al. | |
| 6,872,395 B2 | 3/2005 | Kawaoka | |
| 6,951,752 B2 | 10/2005 | Reiter et al. | |
| 6,951,754 B2 | 10/2005 | Hoffmann | |
| 6,974,695 B2 | 12/2005 | Vogels et al. | |
| 7,037,707 B2 | 5/2006 | Webster et al. | |
| 7,176,021 B2 | 2/2007 | Kawaoka | |
| 7,226,774 B2 | 6/2007 | Kawaoka | |
| 7,312,064 B2 | 12/2007 | Hoffmann | |
| 7,507,411 B2 | 3/2009 | Zhou et al. | |
| 7,566,458 B2 | 7/2009 | Yang et al. | |
| 7,585,657 B2 | 9/2009 | Kawaoka | |
| 7,588,769 B2 | 9/2009 | Kawaoka | |
| 7,670,837 B2 | 3/2010 | Schwartz | |
| 7,833,788 B2 | 11/2010 | Pau et al. | |
| 7,883,844 B2 | 2/2011 | Nouchi et al. | |
| 7,955,833 B2 | 6/2011 | Reiter et al. | |
| 7,959,930 B2 | 6/2011 | De Wit et al. | |
| 7,972,843 B2 | 7/2011 | Hoffmann | |
| 7,993,924 B2 | 8/2011 | Billeter et al. | |

(Continued)

FOREIGN PATENT DOCUMENTS

| | | |
|---|---|---|
| AU | 2012204138 B2 | 5/2014 |
| AU | 2014202470 | 11/2016 |

(Continued)

OTHER PUBLICATIONS

"Australian Application Serial No. 2014202470, Respojnse filed Jul. 4, 2016 to Subsequent Examiners Report dated Feb. 1, 2016", 3 pgs.
"Australian Application Serial No. 2014202470, Response filed Jul. 20, 2016 to Subsequent Examiners Report dated Jul. 19, 2016", 15 pgs.
"Australian Application Serial No. 2014202470, Subsequent Examinsers Report dated Feb. 1, 2016", 2 pgs.
"Australian Application Serial No. 2014202470, Subsequent Examiners Report dated Jul. 19, 2016", 3 pgs.

(Continued)

*Primary Examiner* — Benjamin P Blumel
(74) *Attorney, Agent, or Firm* — Schwegman Lundberg & Woessner, P.A.

(57) ABSTRACT

The invention provides a composition useful to prepare high titer influenza viruses, e.g., in the absence of helper virus, which includes at least five internal genes from an influenza virus isolate that replicates to high titers in embryonated chicken eggs or MDCK cells.

23 Claims, 17 Drawing Sheets

(56) References Cited

U.S. PATENT DOCUMENTS

| | | | |
|---|---|---|---|
| 8,012,736 B2 | 9/2011 | Hoffman et al. |
| 8,048,430 B2 | 11/2011 | Yang et al. |
| 8,057,806 B2 | 11/2011 | Kawaoka et al. |
| 8,093,033 B2 | 1/2012 | Kemble et al. |
| 8,114,415 B2 | 2/2012 | Hoffmann et al. |
| 8,119,337 B2 | 2/2012 | Gregersen |
| 8,119,388 B2 | 2/2012 | Schwartz et al. |
| 8,309,099 B2 | 11/2012 | Hoffmann |
| 8,354,114 B2 | 1/2013 | Lu et al. |
| 8,357,376 B2 | 1/2013 | Liu et al. |
| 8,409,843 B2 | 4/2013 | Kemble et al. |
| 8,460,914 B2 | 6/2013 | Gregersen |
| 8,475,806 B2 | 7/2013 | Kawaoka |
| 8,524,497 B2 | 9/2013 | Reiter et al. |
| 8,546,123 B2 | 10/2013 | Lewis |
| 8,574,591 B2 | 11/2013 | Hoffmann et al. |
| 8,574,593 B2 | 11/2013 | Yang et al. |
| 8,580,277 B2 | 11/2013 | Yang et al. |
| 8,591,914 B2 | 11/2013 | Yang et al. |
| 9,254,318 B2 | 2/2016 | Kawaoka et al. |
| 2002/0164770 A1 | 11/2002 | Hoffmann |
| 2002/0197705 A1 | 12/2002 | Kawaoka |
| 2003/0035814 A1 | 2/2003 | Kawaoka et al. |
| 2003/0044962 A1 | 3/2003 | Makizumi et al. |
| 2003/0073223 A1 | 4/2003 | Groner et al. |
| 2003/0119183 A1 | 6/2003 | Groner |
| 2004/0002061 A1 | 1/2004 | Kawaoka |
| 2004/0063141 A1 | 4/2004 | Lok |
| 2004/0077086 A1 | 4/2004 | Reiter et al. |
| 2004/0219170 A1 | 11/2004 | Kawaoka |
| 2005/0003349 A1 | 1/2005 | Kawaoka |
| 2005/0037487 A1 | 2/2005 | Kawaoka et al. |
| 2005/0118140 A1 | 6/2005 | Vorlop et al. |
| 2005/0158342 A1 | 7/2005 | Kemble et al. |
| 2005/0186563 A1 | 8/2005 | Hoffmann |
| 2005/0202553 A1 | 9/2005 | Groner et al. |
| 2005/0232950 A1 | 10/2005 | Kawaoka |
| 2005/0266026 A1 | 12/2005 | Hoffmann et al. |
| 2006/0166321 A1 | 7/2006 | Kawaoka et al. |
| 2006/0188977 A1 | 8/2006 | Schwartz et al. |
| 2006/0246092 A1 | 11/2006 | Neirynck et al. |
| 2008/0233560 A1 | 9/2008 | Hoffmann |
| 2008/0254067 A1 | 10/2008 | Trepanier et al. |
| 2008/0274141 A1 | 11/2008 | Groner et al. |
| 2008/0311148 A1 | 12/2008 | Hoffmann |
| 2008/0311149 A1 | 12/2008 | Hoffmann |
| 2009/0081252 A1 | 3/2009 | Gregersen |
| 2009/0181446 A1 | 7/2009 | Nouchi et al. |
| 2010/0112000 A1 | 5/2010 | Schwartz et al. |
| 2010/0183671 A1 | 7/2010 | Gregersen et al. |
| 2010/0247572 A1 | 9/2010 | Kawaoka |
| 2011/0027314 A1 | 2/2011 | Broeker et al. |
| 2011/0045022 A1 | 2/2011 | Tsai |
| 2011/0110978 A1 | 5/2011 | Kawaoka et al. |
| 2012/0020997 A1 | 1/2012 | Hoffman et al. |
| 2012/0034600 A1 | 2/2012 | Gregersen |
| 2012/0115206 A1 | 5/2012 | Schwartz et al. |
| 2012/0156241 A1 | 6/2012 | De Wit et al. |
| 2012/0207785 A1 | 8/2012 | Fabry et al. |
| 2013/0095135 A1 | 4/2013 | Collignon et al. |
| 2013/0183741 A1 | 7/2013 | Park et al. |
| 2013/0316434 A1 | 11/2013 | Reiter et al. |
| 2015/0017205 A1 | 1/2015 | Kawaoka et al. |

FOREIGN PATENT DOCUMENTS

| | | | |
|---|---|---|---|
| CN | 1826407 B | 9/2013 |
| EP | 0702085 A1 | 3/1996 |
| EP | 1201760 A1 | 5/2002 |
| EP | 2010557 B1 | 2/2014 |
| EP | 1631663 B1 | 8/2016 |
| IL | 171931 A | 5/2015 |
| JP | 2004500842 A | 1/2004 |
| JP | 2005523698 A | 8/2005 |
| JP | 2005245302 A | 9/2005 |
| JP | 2005535288 A | 11/2005 |
| JP | 2009-532352 a | 9/2009 |
| JP | 2014-039551 A | 3/2014 |
| JP | 2014131516 A | 7/2014 |
| JP | 2016-524915 A | 8/2016 |
| JP | 2016-169225 A | 9/2016 |
| MX | 285206 | 3/2011 |
| WO | WO-96/10632 A1 | 4/1996 |
| WO | WO-96/40955 A1 | 12/1996 |
| WO | WO-97/37000 A1 | 10/1997 |
| WO | WO-98/02530 A1 | 1/1998 |
| WO | WO-98/53078 A1 | 11/1998 |
| WO | WO-99/28445 A1 | 6/1999 |
| WO | WO-00/53786 A1 | 9/2000 |
| WO | WO-0060050 A2 | 10/2000 |
| WO | WO-00/60050 A3 | 1/2001 |
| WO | WO-01/79273 A2 | 10/2001 |
| WO | WO-0183794 A2 | 11/2001 |
| WO | WO-2001083794 A2 | 11/2001 |
| WO | WO-03068923 A2 | 8/2003 |
| WO | WO-03/076462 A1 | 9/2003 |
| WO | WO-03091401 A2 | 11/2003 |
| WO | WO-2003091401 A2 | 11/2003 |
| WO | WO-2004/094466 A2 | 11/2004 |
| WO | WO-2004/112831 A3 | 12/2004 |
| WO | WO-04112831 A2 | 12/2004 |
| WO | WO-2004112831 A2 | 12/2004 |
| WO | WO-2005062820 A2 | 7/2005 |
| WO | WO-2007126810 A2 | 11/2007 |
| WO | WO-2011/056591 A1 | 5/2011 |
| WO | WO-2015/009743 A1 | 1/2015 |

OTHER PUBLICATIONS

"Chinese Application Serial No. 200780020095.1, Office Action dated Apr. 26, 2016", 3 pgs.

"Chinese Application Serial No. 200780020095.1, Response filed Jun. 30, 2016 to Office Action dated Apr. 26, 2016", W/ English Translation of Claims, 22 pgs.

"Japanese Application Serial No. 2014-049025, Examiners Decision of Final Refusal dated Feb. 2, 2016", W/ English Translation, 5 pgs.

Result 17, NCBI Blast nucleotide search of SEQ ID No. 2, database "nr".

Result 1, NCCBI Blast nucleotide search of SEQ ID No. 3, database "nr"; Result 4, NCBI Blast nucleotide search of SEQ ID No. 4, database "nr".

Result 2, NCBI Blast nucleotide search of SEQ ID No. 5, database "nr"; Result 4, NCBI Blast nucleotide search of SEQ ID No. 6, database "nr".

Results 1, NCBI Blast nucleotide search of SEQ ID No. 7, database "nr"; Result 1, NCBI Blast nucleotide search of SEQ ID No. 8, database "nr".

Result 7, NCBI Blast nucleotide search of SEQ ID: 1, database "nr".

"U.S. Appl. No. 11/729,557, Advisory Action dated May 9, 2011", 3 pgs.

"U.S. Appl. No. 11/729,557, Advisory Action dated Dec. 24, 2014", 3 pgs.

"U.S. Appl. No. 11/729,557, Final Office Action dated Feb. 2, 2011", 14 pgs.

"U.S. Appl. No. 11/729,557, Final Office Action dated Aug. 20, 2009", 13 Pgs.

"U.S. Appl. No. 11/729,557, Final Office Action dated Sep. 12, 2014", 14 pgs.

"U.S. Appl. No. 11/729,557, Non Final Office Action dated Feb. 18, 2015", 13 pgs.

"U.S. Appl. No. 11/729,557, Non Final Office Action dated Feb. 26, 2014", 16 pgs.

"U.S. Appl. No. 11/729,557, Non-Final Office Action dated Jan. 30, 2009", 20 pgs.

"U.S. Appl. No. 11/729,557, Non-Final Office Action dated Feb. 22, 2010", 16 pgs.

"U.S. Appl. No. 11/729,557, Non-Final Office Action dated Aug. 23, 2010", 15 pgs.

"U.S. Appl. No. 11/729,557, Notice of Allowance dated Sep. 30, 2015", 11 pgs.

(56) References Cited

OTHER PUBLICATIONS

"U.S. Appl. No. 11/729,557, Respons filed Jun. 22, 2010 to Non Final Office Action dated Feb. 22, 2010", 33 pgs.
"U.S. Appl. No. 11/729,557, Response filed Apr. 27, 2011 to Final Office Action dated Feb. 2, 2011", 14 pgs.
"U.S. Appl. No. 11/729,557, Response filed Apr. 30, 2009 to Non Final Office Action dated Jan. 30, 2009", 18 pgs.
"U.S. Appl. No. 11/729,557, Response filed May 22, 2014 to Non Final Office Action dated Feb. 26, 2014", 13 pgs.
"U.S. Appl. No. 11/729,557, Response filed May 28, 2008 to Restriction Requirement dated Nov. 28, 2007", 13 pgs.
"U.S. Appl. No. 11/729,557, Response filed Jun. 22, 2010 to Non Final Office Action dated Feb. 22, 2010", 16 pgs.
"U.S. Appl. No. 11/729,557, Response filed Jun. 22, 2015 to non Final Office Action dated Feb. 18, 2015", 13 pgs.
"U.S. Appl. No. 11/729,557, Response filed Oct. 28, 2010 to Non Final Office Action dated Aug. 23, 2010", 13 pgs.
"U.S. Appl. No. 11/729,557, Response filed Dec. 1, 2009 to Final Office Action dated Aug. 26, 2009", 16 pgs.
"U.S. Appl. No. 11/729,557, Response filed Dec. 11, 2014 to Final Office Action dated Sep. 12, 2014", 15 pgs.
"U.S. Appl. No. 11/729,557, Restriction Requirement dated Nov. 28, 2007", 9 pgs.
"Australian Application Serial No. 2007245192, Office Action dated Aug. 25, 2011", 2 pgs.
"Australian Application Serial No. 2007245192, Response filed Feb. 28, 2012 to Office Action dated Aug. 25, 2011", 22 pgs.
"Australian Application Serial No. 2012204138, First Examiner Report dated Jul. 16, 2013", 4 pgs.
"Australian Application Serial No. 2012204138, Response filed Dec. 24, 2013 to First Examiner Report dated Jul. 16, 2013", 21 pgs.
"Canadian Application Serial No. 2,647,985 , Office Action dated May 15, 2013", 3 pgs.
"Canadian Application Serial No. 2,647,985 , Response filed Sep. 30, 2013 to Office Action dated May 15, 2013".
"Chinese Application Serial No. 200780020095.1, Decision on Rejection dated Jul. 22, 2013", (w/ English Translation), 11 pgs.
"Chinese Application Serial No. 200780020095.1, First Office Action dated Jun. 24, 2011", (w/English Translation), 13 pgs.
"Chinese Application Serial No. 200780020095.1, Office Action dated Jan. 29, 2013", (w/English Translation), 10 pgs.
"Chinese Application Serial No. 200780020095.1, Office Action dated Mar. 5, 2015", (w/English Translation), 12 pgs.
"Chinese Application Serial No. 200780020095.1, Office Action dated May 3, 2012", With English Translation, 10 pgs.
"Chinese Application Serial No. 200780020095.1, Response filed Jun. 9, 2013 to Office Action dated Jan. 29, 2013", (w/ English Translation of Claims), 10 pgs.
"Chinese Application Serial No. 200780020095.1, Response filed Jun. 23, 2015 to Office Action dated Mar. 5, 2015", (w/ English Translation of Claims), 16 pgs.
"Chinese Application Serial No. 200780020095.1, Response filed Sep. 17, 2012 to Office Action dated May 3, 2012", (w/ English Translation of Claims), 17 pgs.
"Chinese Application Serial No. 200780020095.1, Response filed Nov. 5, 2013 to to Decision on Rejection dated Jul. 22, 2013", (w/ English Translation of Claims), 12 pgs.
"Chinese Application Serial No. 200780020095.1, Response filed Nov. 8, 2011 to Office Action dated Jun. 24, 2011", (w/ English Translation of Amended Claims), 20 pgs.
"European Application Serial No. 07754132.4, Office Action dated Apr. 28, 2009", 4 pgs.
"European Application Serial No. 07754132.4, Office Action dated Sep. 5, 2011", 5 pgs.
"European Application Serial No. 07754132.4, Office Action dated Nov. 2, 2012", 4 pgs.
"European Application Serial No. 07754132.4, Response filed Feb. 5, 2010 to Office Action dated Apr. 28, 2009", 15 pgs.
"European Application Serial No. 07754132.4, Response filed Mar. 15, 2012 to Office Action dated Sep. 5, 2011", 21 pgs.
"European Application Serial No. 07754132.4, Response filed May 10, 2013 to Office Action dated Nov. 2, 2012", 14 pgs.
"European Application Serial No. 07754132.4, Response filed Jun. 26, 2013", 8 pgs.
"Japanese Application Serial No. 2009-502945, Examiners Decision of Final Refusal dated Nov. 12, 2013", (w/ English Translation), 8 pgs.
"Japanese Application Serial No. 2009-502945, Office Action dated Oct. 23, 2012", (w/ English Translation), 16 pgs.
"Japanese Application Serial No. 2009-502945, Response filed Apr. 10, 2013 to Office Action dated Oct. 23, 2012", (w/ English Translation of Claims), 18 pgs.
"Japanese Application Serial No. 2014-049025, Office Action dated Jun. 16, 2015", (w/ English Translation), 6 pgs.
"PCT Application No. PCT/US2004/016680, International Search Report", (dated Feb. 2, 2005), 7 pgs.
"PCT Application Serial No. PCT/US2007/007562, International Preliminary Report on Patentability dated Oct. 9, 2008", 5 pgs.
"PCT Application Serial No. PCT/US2007/007562, International Search Report dated Jan. 14, 2008", 8 pgs.
"PCT Application Serial No. PCT/US2007/007562, Written Opinion dated Jan. 14, 2008", 9 pgs.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Chen, H, et al., "Generation and evaluation of a high-growth reassortant H9N2 influenza A virus as a pandemic vaccine candidate", Vaccine, 21(17-18), (May 16, 2003), 1974-9.
De, B. P., et al., "Reverse Genetics of Negative Strand RNA Viruses", Indian Journal of Biochemistry & Biophysics, 31, (1994), 367-375.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Elliott, R. M., et al., "Rescue of Infectious Bunyavirus Entirely From Cloned cDNA", 10th International Conference on Negative Strand Virus, (Abstract No. 96), (1997), 1 pg.
Fodor, E., "Rescue of Influenza A Virus from Recombinant DNA", Journal of Virology, 73(11), (Nov. 1999), 9679-9682.
Hoffmann, E., et al., "A DNA transfection system for generation of influenza A virus from eight plasmids", Proc Natl Acad Sci U S A., 97(11), (May 23, 2000), 6108-13.
Hoffmann, E., et al., "A DNA transfection system for generation of influenza A virus from eight plasmids", Proc. Natl. Acad. Sci., 97(11), (2000), 6108-6113.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Holmes, E. C, et al., "Whole-Genome Analysis of Human Influenza A Virus Reveals Multiple Persistent Lineages and Reassortment Among Recent H3N2 Viruses", PLoS Biology, 3(9), (2005), 1579-1589.
Horimoto, T., et al., "Generation of Influenza A Viruses with Chimeric (Type A/B) Hemagglutinins", Journal of Virology, 77(14), (2003), 8031-8038.
Horimoto, T., et al., "The Development and Characterization of H5 Influenza Virus Vaccines Derived from a 2003 Human Isolate", Vaccine, 24(17), (2006), 3669-3676.
Katinger, D., et al., "Attenuated Influenza Viruses as a Vector for Mucosal Immunization Against HIV-1", Vaccines, 97, Cold Spring Harbor, (1997), 315-319.
Kiseleva, et al., "Role of individual genes of the A-Leningrad/134/17/57 (H2N2) cold-adapted donor strain in manifestation of the

(56) References Cited

OTHER PUBLICATIONS temperature-sensitive phenotype of reassortant influenza A viruses", International Congress Series, vol. 1263, (2004), 547-550.

Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.

Lazarovits, et al., "Endocytosis of Chimeric Influenza Virus Hemaggulutinin Proteins That Lack a Cytoplasmic Recognition Feature for Coated Pits", The Journal of Cell Biology, vol. 134, No. 2, (1996), 339-348.

Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.

Matsuoka, et al., "Neuraminidase Stalk Length and Additional Glycosylation of the Hemagglutinin Influence the Virulence of Influenza H5N1 Viruses for Mice", Journal of Virology, vol. 83, No. 9 (2009), pp. 4704-4708.

Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.

Neumann, G., et al., "Generation of influenza A virus from cloned cDNAs—historical perspective and outlook for the new millenium. ", Rev Med Virol., 12(1), XP002314285, (Jan.-Feb. 2002), 13-30.

Neumann, G., et al., "Generation of influenza A viruses entirely from cloned cDNAs", Proc. Natl. Acad. Sci. USA, 96(16), (1999), 9345-9350.

Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.

Odagiri, T., et al., "Nucleotide Sequence of the PA Gene of Influenza A/WSN/33 (H1N1)", Nucleic Acids Research, 18 (3), Department of Virology, (Jan. 9, 1990).

Orkin, S. H, et al., "Report and Recommendations of the Panel to Assess the NIH Investment in Research on Gene Therapy", http://www.nih.gov/news/panelrep.html, (Dec. 7, 1995), 37 pgs.

Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.

Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.

Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.

Verma, I. M, et al., "Gene Therapy—Promises, Problems and Prospects", Nature, 389, (Sep. 18, 1997), 239-242.

Voeten, J. T, et al., "Characterization of high-growth reassortant influenza A viruses generated in MDCK cells cultured in serum-free medium", Vaccine, vol. 17, (1999), 1942-1950.

Winter, G., et al., "The use of synthetic oligodeoxynucleotide primers in cloning and sequencing segment 8 of influenza virus (A/PR/8/34)", Nucleic Acids Res., 9(2), (1981), 237-245.

Yannarell, et al., "Factors affecting the yield of cold-adapted influenza virus vaccine", Journal of Virological Methods, vol. 64, (1997), 161-169.

"1.A.32 The Type B Influenza Virus NB Channel (NB-C) Family", Transport Protein Database, (University of California, San Diego, The Sailer Laboratory Bioinformatics Group) [online}. http://www.web.archive.org/web/20030131105524/http://tcdb.ucsd.edu/tcdb/tcfamilybrowse.php?tcname=1.A.32, (Archived Jan. 31, 2003), 1 pg.

"U.S. Appl. No. 09/834,095, Advisory Action dated Jan. 8, 2004", 3 pgs.

"U.S. Appl. No. 09/834,095, Final Office Action dated Aug. 26, 2003", 12 pgs.

"U.S. Appl. No. 09/834,095, Non-Final Office Action dated Nov. 4, 2002", 12 pgs.

"U.S. Appl. No. 09/834,095, Notice of Allowance dated Sep. 27, 2004", 13 pgs.

"U.S. Appl. No. 09/834,095, Office Action dated Apr. 20, 2004", 11 pgs.

"U.S. Appl. No. 09/834,095, Response filed Feb. 4, 2003 to Office Action dated Nov. 4, 2002", 14 pgs.

"U.S. Appl. No. 09/834,095, Response filed Jun. 12, 2003 to Restriction Requirement dated Apr. 22, 2003", 2 pgs.

"U.S. Appl. No. 09/834,095, Response filed Jun. 18, 2004 to Office Action dated Apr. 20, 2004", 11 pgs.

"U.S. Appl. No. 09/834,095, Response filed Aug. 1, 2002 to Restriction Requirement dated Jul. 1, 2002", 3 pgs.

"U.S. Appl. No. 09/834,095, Response filed Nov. 26, 2003 to Final Office Action dated Aug. 26, 2003", 10 pgs.

"U.S. Appl. No. 09/834,095, Restriction Requirement dated Apr. 22, 2003", 5 pgs.

"U.S. Appl. No. 09/834,095, Restriction Requirement dated Jul. 1, 2002", 9 pgs.

"U.S. Appl. No. 09/834,095, Supplemental Amendment filed Aug. 4, 2004", 7 pgs.

"U.S. Appl. No. 10/827,995, Final Office Action dated Nov. 15, 2006", 10 pgs.

"U.S. Appl. No. 10/827,995, Non-Final Office Action dated Jun. 2, 2006", 15 pgs.

"U.S. Appl. No. 10/827,995, Non-Final Office Action dated Oct. 25, 2007", 7 pgs.

"U.S. Appl. No. 10/827,995, Notice of Allowance dated Feb. 17, 2009", 9 pgs.

"U.S. Appl. No. 10/827,995, Notice of Allowance dated Jul. 2, 2008", 9 pgs.

"U.S. Appl. No. 10/827,995, Notice of Allowance dated Oct. 17, 2008", 7 pgs.

"U.S. Appl. No. 10/827,995, Notice of Non-Compliant Amendment dated Jul. 25, 2007", 4 pgs.

"U.S. Appl. No. 10/827,995, Proposed Examiner's Amendment dated Jun. 5, 2008", 6 pgs.

"U.S. Appl. No. 10/827,995, Response filed Mar. 3, 2008 to Office Action dated Oct. 25, 2007", 10 pgs.

"U.S. Appl. No. 10/827,995, Response filed May 14, 2007 Final Office Action dated Nov. 15, 2006", 16 pgs.

"U.S. Appl. No. 10/827,995, Response filed Aug. 13, 2007 to Notice of Non-Compliant Amendment dated Jul. 25, 2007", 16 pgs.

"U.S. Appl. No. 10/827,995, Response filed Aug. 17, 2006 Non-Final Office Action dated Jun. 2, 2006", 15 pgs.

"U.S. Appl. No. 10/855,875 , Response filed May 17, 2012 to Non Final Office Action dated Mar. 15, 2012", 15 pgs.

"U.S. Appl. No. 10/855,875, Final Office Action dated Mar. 11, 2008", FOAR, 20 Pgs.

"U.S. Appl. No. 10/855,875, Final Office Action dated Dec. 10, 2010", 15 pgs.

"U.S. Appl. No. 10/855,875, Final Office Action dated Aug. 2, 2006", 34 pgs.

"U.S. Appl. No. 10/855,875, Non Final Office Action dated Mar. 15, 2012", 15 pgs.

"U.S. Appl. No. 10/855,875, Non-Final Office Action dated Feb. 19, 2010", 7 pgs.

"U.S. Appl. No. 10/855,875, Non-Final Office Action dated Aug. 7, 2009", 32 pgs.

"U.S. Appl. No. 10/855,875, Non-Final Office Action dated Nov. 6, 2008", 12 pgs.

"U.S. Appl. No. 10/855,875, Non-Final Office Action dated Nov. 30, 2005", 13 pgs.

"U.S. Appl. No. 10/855,875, Non-Final Office Action dated May 3, 2007", 13 pgs.

"U.S. Appl. No. 10/855,875, Notice of Allowance dated Mar. 4, 2013", 8 pgs.

"U.S. Appl. No. 10/855,875, Preliminary Amendment filed Feb. 2, 2007", 14 pgs.

(56) References Cited

OTHER PUBLICATIONS

"U.S. Appl. No. 10/855,875, Response filed Jan. 29, 2007 to Final Office Action dated Aug. 2, 2007", 14 pgs.
"U.S. Appl. No. 10/855,875, Response filed Mar. 18, 2011 to Final Office Action dated Dec. 20, 2010", 15 pgs.
"U.S. Appl. No. 10/855,875, Response filed Aug. 17, 2010 to Non Final Office Action dated Feb. 19, 2010", 20 pgs.
"U.S. Appl. No. 10/855,875, Response filed Dec. 7, 2009 to Non Final Office Action dated Aug. 7, 2009", 15 pgs.
"U.S. Appl. No. 10/855,875, Response Filed Dec. 7, 2009 to Non-Final Office Action dated Aug. 7, 2009", 15 pgs.
"U.S. Appl. No. 10/855,875, Response filed Mar. 31, 2009 to Non Final Office Action dated Nov. 6, 2008", 14 pgs.
"U.S. Appl. No. 10/855,875, Response filed May 1, 2006 Non-Final Office Action dated Nov. 30, 2005", 13 pgs.
"U.S. Appl. No. 10/855,875, Response filed Aug. 18, 2008 to final Office Action dated Mar. 11, 2008", 15 pgs.
"U.S. Appl. No. 10/855,875, Response filed Sep. 20, 2005 to Restriction Requirement dated Jul. 26, 2005", 4 pgs.
"U.S. Appl. No. 10/855,875, Restriction Requirement dated Dec. 23, 2011", 9 pgs.
"U.S. Appl. No. 10/855,875, Restriction Requirement dated Jul. 26, 2005", 9 pgs.
"U.S. Appl. No. 10/855,875, Response filed Nov. 2, 2007 to Office Action dated May 3, 2007" 16 pgs.
"U.S. Appl. No. 11/043,768, Non-Final Office Action dated Sep. 27, 2010", 8 pgs.
"U.S. Appl. No. 11/043,768, Final Office Action dated Jun. 27, 2008", 8 pgs.
"U.S. Appl. No. 11/043,768, Non-Final Office Action dated Feb. 23, 2010", 6 pgs.
"U.S. Appl. No. 11/043,768, Non-Final Office Action dated Feb. 23, 2009", 7 pgs.
"U.S. Appl. No. 11/043,768, Non-Final Office Action dated Nov. 28, 2007", 9 pgs.
"U.S. Appl. No. 11/043,768, Notice of Allowance dated Jun. 29, 2011", 12 pgs.
"U.S. Appl. No. 11/043,768, Response filed May 2, 2011 to Final Office Action dated Feb. 3, 2011", 11 pgs.
"U.S. Appl. No. 11/043,768, Response filed Jun. 15, 2010 to Non Final Office Action dated Feb. 23, 2010", 9 pgs.
"U.S. Appl. No. 11/043,768, Response filed Jun. 23, 2009 to Non Final Office Action dated Feb. 23, 2009", 9 pgs.
"U.S. Appl. No. 11/043,768, Response filed Jun. 23, 2009 to Non-Final Office Action dated Feb. 23, 2009", 9 pgs.
"U.S. Appl. No. 11/043,768, Response filed Sep. 13, 2007 to Restriction Requirement dated Mar. 13, 2007", 10 pgs.
"U.S. Appl. No. 11/043,768, Response filed Oct. 26, 2010 to Non Final Office Action dated Sep. 27, 2010", 11 pgs.
"U.S. Appl. No. 11/043,768, Response filed Dec. 12, 2008 to Final Office Action dated Jun. 27, 2008", 9 pgs.
"U.S. Appl. No. 11/043,768, Response filed Mar. 10, 2008 to Office Action dated Nov. 28, 2007", 12 pgs.
"U.S. Appl. No. 11/043,768, Restriction Requirement dated Mar. 13, 2007", 9 pgs.
"U.S. Appl. No. 11/043,786, Final Office Action dated Feb. 3, 2011", 10 pgs.
"U.S. Appl. No. 12/467,492, Restriction Requirement dated Nov. 22, 2010", 6 pgs.
"U.S. Appl. No. 12/912,411, Advisory Action dated Feb. 5, 2014", 3 pgs.
"U.S. Appl. No. 12/912,411, Examiner Interview Summary dated Feb. 11, 2014", 2 pgs.
"U.S. Appl. No. 12/912,411, Final Office Action dated Jan. 14, 2015", 10 pgs.
"U.S. Appl. No. 12/912,411, Final Office Action dated Oct. 25, 2013", 11 pgs.
"U.S. Appl. No. 12/912,411, Non Final Office Action dated Jun. 7, 2013", 8 pgs.
"U.S. Appl. No. 12/912,411, Non Final Office Action dated Sep. 24, 2014", 11 pgs.
"U.S. Appl. No. 12/912,411, Response filed Jan. 27, 2014 to Final Office Action dated Oct. 25, 2013", 11 pgs.
"U.S. Appl. No. 12/912,411, Response filed Feb. 18, 2013 to Restriction Requirement dated Oct. 17, 2012", 9 pgs.
"U.S. Appl. No. 12/912,411, Response filed Feb. 25, 2014 to Final Office Action dated Oct. 25, 2013" 11 pgs.
"U.S. Appl. No. 12/912,411, Response filed Oct. 7, 2013 to Non Final Office Action dated Jun. 7, 2013", 10 pgs.
"U.S. Appl. No. 12/912,411, Response filed Dec. 31, 2014 to Non Final Office Action dated Sep. 24, 2014", 12 pgs.
"U.S. Appl. No. 12/912,411, Restriction Requirement dated Oct. 17, 2012", 9 pgs.
"U.S. Appl. No. 14/332,121, Non Final Office Action dated May 16, 2016", 9 pgs.
"U.S. Appl. No. 14/332,121, Notice of Allowance dated Feb. 15, 2017", 10 pgs.
"U.S. Appl. No. 14/332,121, Notice of Allowance dated Jun. 15, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement dated Jul. 30, 2015", 9 pgs.
"U.S. Appl. No. 14/332,121, Response filed Oct. 11, 2016 to Non Final Office Action dated May 16, 2016", 9 pgs.
"U.S. Appl. No. 14/332,121, Restriction Requirement dated Jul. 30, 2015", 9 pgs.
"U.S. Appl. No. 14/332,121, Supplemental Amendment filed Jan. 23, 2017", 10 pgs.
"U.S. Appl. No. 14/745,236, Non Final Office Action dated Feb. 2, 2017", 14 pgs.
"U.S. Appl. No. 14/745,236, Response filed May 2, 2017 to Non Final Office Action dated Feb. 2, 2017", 10 pgs.
"U.S. Appl. No. 14/745,236, Response filed Dec. 23, 2016 to Restriction Requirement dated Sep. 23, 2016", 8 pgs.
"U.S. Appl. No. 15/593,039, Preliminary Amendment filed Jul. 25, 2017", 7 pgs.
"U.S. Appl. No. 15/593,039, Supplemental Preliminary Amendment filed Jul. 26, 2017", 4 pgs.
"Application Serial No. 200480021259:9 Office Action dated Sep. 11, 2009", 7 pgs.
"Application Serial No. 200480021259.9 Office Action Response Filed Aug. 20, 2010", 26 pgs.
"Application Serial No. 2006-533439 Office Action dated Mar. 9, 2010", 20 pgs.
"Australian Application Serial No. 2001255336, Examiner's First Report dated Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2004249133, First Examiner's Report dated May 5, 2008", 4 pgs.
"Australian Application Serial No. 2004249133, Response filed Mar. 30, 2009 to First Examiner's Report dated May 5, 2008", 30 pgs.
"Brazilian Application Serial No. PI0410702-0, Office Action dated Mar. 13, 2012", (w/ English Translation), 4 pgs.
"Brazilian Application Serial No. PI0410702-0, Response filed May 7, 2012 to Office Action dated Mar. 13, 2012", (w/ English Translation of Claims), 11 pgs.
"Canadian Application Serial No. 2,406,180, Office Action dated Sep. 9, 2008", 5 pgs.
"Canadian Application Serial No. 2,406,180, Office Action dated Nov. 10, 2011", 3 pgs.
"Canadian Application Serial No. 2,406,180, Office action dated Nov. 23, 2009", 3 pgs.
"Canadian Application Serial No. 2,406,180, Office Action dated Dec. 10, 2010", 2 pgs.
"Canadian Application Serial No. 2,406,180, Response filed Jan. 26, 2009 to Official Action dated Sep. 9, 2008", 22 pgs.
"Canadian Application Serial No. 2,406,180, Response filed May 21, 2010 to Office action dated Nov. 23, 2009", 13 pgs.

(56) References Cited

OTHER PUBLICATIONS

"Canadian Application Serial No. 2,406,180, Response filed Jun. 14, 2011 to Office Action dated Dec. 10, 2010", 10 pgs.
"Canadian Application Serial No. 2,522,081, Amendment After Allowance filed Aug. 10, 2012", 3 pgs.
"Canadian Application Serial No. 2,522,081, Office Action dated Jun. 6, 2011", 2 pgs.
"Canadian Application Serial No. 2,522,081, Office Action dated Aug. 30, 2010", 2 pgs.
"Canadian Application Serial No. 2,522,081, Office Action dated Oct. 8, 2009", 6 pgs.
"Canadian Application Serial No. 2,522,081, Response filed Feb. 28, 2011 to Office Action dated Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action dated Jun. 6, 2011", 11 pgs.
"Canadian Application Serial No. 2,525,953, Office Action dated Jan. 21, 2016", 6 pgs.
"Canadian Application Serial No. 2,525,953, Office Action dated Jul. 31, 2012", 4 pgs.
"Canadian Application Serial No. 2,525,953, Office Action dated Aug. 1, 2016", 6 pgs.
"Canadian Application Serial No. 2,525,953, Office Action dated Aug. 16, 2013", 3 pgs.
"Canadian Application Serial No. 2,525,953, Office Action dated Nov. 6, 2014", 3 pgs.
"Canadian Application Serial No. 2,525,953, Office Action Response filed Dec. 22, 11", 17 pgs.
"Canadian Application Serial No. 2,525,953, Response filed Feb. 14, 2014 to Office Action dated Aug. 16, 2013", 16 pgs.
"Canadian Application Serial No. 2,525,953, Response filed Jul. 11, 2016 to Office Action dated Jan. 21, 2016", 21 pgs.
"Canadian Application Serial No. 205962, Office Action dated Jun. 22, 2011", 4 pgs.
"Canadian Application Serial No. 2406180, Response filed May 7, 2012 to Office Action dated Nov. 10, 2011", 11 pgs.
"Canadian Application Serial No. 2525953, Office Action dated Jun. 22, 2011", 4 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action dated Mar. 1, 2010", (w/ English Translation of Claims), 16 pgs.
"Chinese Application Serial No. 200480017037.X, Response filed Aug. 4, 2009 to Second Office Action dated Mar. 20, 2009", (w/ English Translation of Amended Claims), 15 pgs.
"Chinese Application Serial No. 200480017037.X, Second Office Action dated Mar. 20, 2009", (w/ English Translation), 7 pgs.
"Chinese Application Serial No. 200480017037.X, Third Office Action dated Mar. 1, 2010", (w/ English Translation), 9 pgs.
"Chinese Application Serial No. 200480021259.9, First Office Action dated Aug. 24, 2007", (w/ English Translation), 9 pgs.
"Chinese Application Serial No. 200480021259.9, Notice of Reexamination dated Jul. 3, 2012", (w/ English Translation), 10 pgs.
"Chinese Application Serial No. 200480021259.9, Office Action dated Jan. 11, 2011", (w/ English Translation), 15 pgs.
"Chinese Application Serial No. 200480021259.9, Office Action dated May 6, 2010", (w/ English Translation), 12 pgs.
"Chinese Application Serial No. 200480021259.9, Office Action dated Jul. 3, 2012", (w/ English Translation), 10 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Office Action dated Aug. 24, 2007", (w/ English Translation of Claims), 13 pgs.
"Chinese Application Serial No. 200480021259.9, Response filed Oct. 16, 2012 to Office Action dated Jul. 3, 2012", (w/ English Translation of Claims), 13 pgs.
"Chinese Application Serial No. 200780020095.1, Office Action dated Nov. 2, 2016", (w/ English Translation), 11 pgs.
"Chinese Application Serial No. 200780020095.1, Response filed Jan. 6, 2017 to Office Action dated Nov. 2, 2016", (w/ English Translation of Claims), 15 pgs.
"Chinese Application Serial No. 200480021259.9, Office Action dated May 8, 2009", (w/ English Translation), 6 pgs.
"Eurasian Application No. 200501890, Notice of Allowance dated Jun. 23, 2009", 1 pg.
"Eurasian Application Serial No. 200501890, Office Action dated Mar. 23, 2007", (w English Translation), 2 pgs.
"Eurasian Application Serial No. 200501890, Office Action dated Dec. 17, 2007", (w/ English Translation), 6 pgs.
"Eurasian Application Serial No. 200501890, Office Action dated Sep. 4, 2008", (English translation), 1 pg.
"Eurasian Application Serial No. 200501890, Response filed Mar. 26, 2008 to Office Action dated Dec. 17, 2007", W/ English Claims, 15 pgs.
"Eurasian Application Serial No. 200501890, Response filed Jun. 14, 2007 to Office Action dated Mar. 23, 2007", W/ English Claims, 11 pgs.
"Eurasian Application Serial No. 200501890, Response filed Dec. 7, 2008 to Office Action dated Sep. 4, 2008", (w/ English Translation of Claims), 14 pgs.
"Eurasian Application Serial No. 200501890, Response filed Dec. 17, 2008 to Office Action", (w/ English Translation of Claims), 13 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication Oct. 12, 2006", 4 pgs.
"European Application Serial No. 01928486.8 Office Action dated Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005". 4 pgs.
"European Application Serial No. 01928486.8, Office Action dated Feb. 19, 2009", 3 pgs.
"European Application Serial No. 01928486.8, Response filed Aug. 28, 2009 to Communication dated Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Jan. 30, 2006 to Communication dated Sep. 20, 2005", 9 pgs.
"European Application Serial No. 01928486.8, Response filed Dec. 9, 2009 to Office Action dated Oct. 1, 2009", 11 pgs.
"European Application Serial No. 04750333.9, Office Action mailed Jan. 22, 2009", 5 pgs.
"European Application Serial No. 04750333.9, Response filed Oct. 21, 2008 to Communication dated Apr. 11, 2008", 15 pgs.
"European Application Serial No. 04750333.9, Response filed Nov. 17, 2009 to Communications dated Jan. 22, 2009", 17 pgs.
"European Application Serial No. 04750333.9, Summons to Attend Oral Proceedings dated Aug. 3, 2011", 13 pgs.
"European Application Serial No. 04776133.3, Communication dated Mar. 30, 2006", 3 pgs.
"European Application Serial No. 04776133.3, EP Office Action dated Jan. 5, 2010", 4 pgs.
"European Application Serial No. 04776133.3, Examination Notification Art. 94(3) dated Jul. 28, 2015", 4 pgs.
"European Application Serial No. 04776133.3, Examination Notification Art. 94(3) dated Nov. 25, 2013", 5 pgs.

(56) References Cited

OTHER PUBLICATIONS

"European Application Serial No. 04776133.3, Response filed Jan. 25, 2007 to Communication dated Mar. 30, 2006", 20 pgs.
"European Application Serial No. 04776133.3, Response filed Apr. 30, 2014 to Examination Notification Art. 94(3) dated Nov. 25, 2013", 12 pgs.
"European Application Serial No. 04776133.3, Response filed Sep. 18, 2015 to Examination Notification Art. 94(3) dated Jul. 28, 2015", 47 pgs.
"European Application Serial No. 04776133.3, Response to Office Action filed Jul. 15, 2010", 9 pgs.
"European Application Serial No. 10777154.5, Examination Notification Art. 94(3) dated Oct. 6, 2014", 7 pgs.
"European Application Serial No. 10777154.5, Office Action dated Jul. 4, 2012", 2 pgs.
"European Application Serial No. 10777154.5, Response filed Jan. 14, 2013 to Office Action dated Jul. 4, 2012", 12 pgs.
"European Application Serial No. 14745060.5, Office Action dated Feb. 23, 2016", 2 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, (2006), 1 pg.
"Indian Application Serial No. 02082/KOLNP/2005, Examination Report dated Mar. 17, 2008", 1 pg.
"Indian Application Serial No. 02082/KOLNP/2005, Examination Report dated Dec. 28, 2007", 1 pg.
"Indian Application Serial No. 02082/KOLNP/2005, First Examination Report dated Jan. 25, 2007", 9 pgs.
"Indian Application Serial No. 02082/KOLNP/2005, Response filed Jan. 22, 2008 to Examination Report dated Dec. 28, 2007", 13 pgs.
"Indian Application Serial No. 02082/KOLNP/2005, Response filed Jun. 10, 2008 to Examination Report dated Mar. 17, 2008", 3 pgs.
"Indian Application Serial No. 02082/KOLNP/2005, Response filed Nov. 19, 2007 to First Examination Report dated Jan. 25, 2007", 26 pgs.
"Indian Application Serial No. 1026/KOLNP/2009, First Examiner Report dated Mar. 13, 2014", 2 pgs.
"Indian Application Serial No. 2272/KOLNP/2005, First Examination Report dated Mar. 17, 2008", 10 pgs.
"Indian Application Serial No. 2272/KOLNP/2005, Response filed Mar. 16, 2009 to Subsequent Examination Report dated Mar. 6, 2009", 12 pgs.
"Indian Application Serial No. 2272/KOLNP/2005, Response filed Oct. 11, 2008 to First Examination Report dated Mar. 17, 2008", 27 pgs.
"Indian Application Serial No. 2272/KOLNP/2005, Subsequent Examination Report dated Mar. 6, 2009", 1 pg.
"Influenza B/lee/40, neuraminidase & nb (seg 6) ma", Database EM_VI E.B.I. Hinxton U.K., (Jun. 13, 1985), 10 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report dated Oct. 15, 2002", 13 pgs.
"International Application Serial No. PCT/US01/11963, International Search Report dated May 7, 2002", 5 pgs.
"International Application Serial No. PCT/US01/11963, Response filed Sep. 9, 2002 to Written Opinion dated Aug. 7, 2002", 12 pgs.
"International Application Serial No. PCT/US01/11963, Written Opinion dated Jun. 14, 2002", 2 pgs.
"International Application Serial No. PCT/US01/11963, Written Opinion dated Aug. 7, 2002", 6 pgs.
"International Application Serial No. PCT/US2004/012050, International Search Report dated Feb. 2, 2005", 8 pgs.
"International Application Serial No. PCT/US2004/012050, Written Opinion dated Feb. 2, 2005", 12 pgs.
"International Application Serial No. PCT/US2004/016680, International Preliminary Report on Patentability dated Dec. 15, 2005", 11 pgs.
"International Application Serial No. PCT/US2010/054128, Preliminary Report on Patentability dated May 10, 2012", 10 pgs.
"International Application Serial No. PCT/US2010/054128, Search Report dated Feb. 23, 2011", 6 pgs.
"International Application Serial No. PCT/US2010/054128, Written Opinion dated Feb. 23, 2011", 8 pgs.
"international Application Serial No. PCT/US2014/046731, International Preliminary Report on Patentability dated Jan. 28, 2016", 12 pgs.
"International Application Serial No. PCT/US2014/046731, International Search Report dated Nov. 25, 2014", 9 pgs.
"International Application Serial No. PCT/US2014/046731, Written Opinion dated Nov. 25, 2014", 10 pgs.
"Israeli Application Serial No. 171831, Notification of Defects dated Nov. 10, 2008", (English Translation), 10 pgs.
"Israeli Application Serial No. 171372, Office Action dated Feb. 21, 2010", (Translation), 2 pgs.
"Israeli Application Serial No. 171372, Office Action dated Nov. 6, 2008", (Translation), 12 pgs.
"Israeli Application Serial No. 171372, Response filed Nov. 18, 2010 to Office Action dated Feb. 21, 2010", (Translation), 19 pgs.
"Israeli Application Serial No. 171831, Office Action dated Feb. 21, 2010", (English Translation), 2 pgs.
"Israeli Application Serial No. 171831, Office Action dated Apr. 18, 2012", (English Translation), 2 pgs.
"Israeli Application Serial No. 171831, Response filed Jan. 20, 2011 to Office Action dated Feb. 21, 2010", (English Translation), 18 pgs.
"Israeli Application Serial No. 171831, Response filed Jun. 24, 2009 to Notification of Defects dated Nov. 10, 2008", (w/ English Translation of Claims), 10 pgs.
"Israeli Application Serial No. 171831, Response filed Nov. 6, 2012 to Office Action dated Apr. 18, 2012", (w/ English Translation of Amended Claims), 54 pgs.
"Israeli Application Serial No. 238584, Office Action dated Apr. 14, 2016", (English Translation), 3 pgs.
"Israeli Application Serial No. 238584, Response filed Aug. 3, 2016 to Office Action dated Apr. 14, 2016", (English Translation of Claims), 19 pgs.
"Israeli Application Serial No. 171372,Office Action dated Feb. 20, 2011", (Translation), 2 pgs.
"Japanese Application No. 2001-576868, Office Action dated May 31, 2011", (w/ English Translation), 5 pgs.
"Japanese Application No. 2001-576868, Response filed Apr. 26, 2011 to Office Action dated Nov. 2, 2010", (w/ Translation of Amended Claims), 14 pgs.
"Japanese Application Serial No. 2001-576868, Office Action dated Nov. 2, 2010", w/ English Translation), 10 pgs.
"Japanese Application Serial No. 2001-576868, Response filed Dec. 1, 2011 to Office Action dated May 3, 2011", (w/ English Translation of Amended Claims), 37 pgs.
"Japanese Application Serial No. 2006-513125, Office Action dated Mar. 9, 2010", (English Translation), 11 pgs.
"Japanese Application Serial No. 2006-513125, Response filed Aug. 30, 2010 to Office Action dated Mar. 9, 2010", (w/ English Translation of Amended Claims), 60 pgs.
"Japanese Application Serial No. 2006-533439, Decision of Final Rejection dated Aug. 14, 2012", (w/ English Translation), 5 pgs.
"Japanese Application Serial No. 2006-533439, Office Action dated Mar. 27, 2012", w/ English Translation, 8 pgs.
"Japanese Application Serial No. 2006-533439, Response filed May 21, 2012 to Office Action dated Mar. 27, 2012", (w/ English Translation of Amended Claims), 19 pgs.
"Japanese Application Serial No. 2006-533439, Response filed Aug. 3, 2011 to Office Action dated Feb. 15, 2011", (w/ English Translation of Amended Claims), 18 pgs.
"Japanese Application Serial No. 2006-533439,Office Action dated Feb. 15, 2011", (w/ English Translation), 13 pgs.
"Japanese Application Serial No. 2006-533439; Office Action Response filed Jul. 9, 2010", (w/ English Translation of Claims), 25 pgs.

(56) References Cited

OTHER PUBLICATIONS

"Japanese Application Serial No. 2011-111048, Office Action dated Jun. 25, 2013", (w/ English Translation), 7 pgs.
"Japanese Application Serial No. 2011-111048, Office Action dated Sep. 18, 2012", (w/ English Translation), 10 pga.
"Japanese Application Serial No. 2011-111048, Response filed Sep. 25, 2012 to Office Action dated Jun. 25, 2013", (w/ English Translation of Amended Claims), 18 pgs.
"Japanese Application Serial No. 2011-111048. Response filed Mar. 15, 2013", (w/ Translation of Amended Clairns), 14 pgs.
"Japanese Application Serial No. 2012-273898, Office Action dated Jun. 10, 2014", (w/ English Translation), 7 pgs.
"Japanese Application Serial No. 2012-273898, Response filed Sep. 4, 2014 to Office Action dated Jun. 10, 2014", W/ English Claims, 9 pgs.
"Japanese Application Serial No. 2012-536963, Office Action dated Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2013-198377, Office Action dated Jan. 6, 2015", (w/ English Translation), 9 pgs.
"Japanese Application Serial No. 2016-110879, Office Action dated May 30, 2017", (w/ English Translation), 7 pgs.
"Japanese Application Serial No. 2006-513125,Final Office Action dated Jan. 18, 2011", (English Translation), 4 pgs.
"Korean Application Serial No. 10-2005-7020077, Response filed Apr. 28, 2008 to Examination Report dated Dec. 28, 2007", (w/ English Translation of Revised Claims), 41 pgs.
"Korean Application Serial No. 10-2005-7020077, Examination Report dated Dec. 28, 2007", (w/ English Translation) 8 pgs.
"Korean Application Serial No. 10-2005-7020077, Notice of Preliminary Rejection dated Jun. 28, 2007", (w/ English Translation), 9 pgs.
"Korean Application Serial No. 10-2005-7020077, Response filed Aug. 28, 2007 to Notice of Preliminary Rejection dated Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action dated Aug. 6, 2008", W/ English Translation, 4 pgs.
"Korean Application Serial No. 10-2005-7022564, Response and Amendment filed Dec. 29, 2008 to Office Action dated Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action dated Aug. 6, 2008", (w/ English Translation of Claims), 16 pgs.
"Mexican Application No. PA/a/2005/012712 Office Action dated Jul. 21, 2009", (w/ English Translation), 9 pgs/.
"Mexican Application Serial No. MX/a/2009/006341, Office Action dated Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action dated May 19, 2015", (w/ English Translation of Claims), 21 pgs.
"Mexican Application Serial No. MX/a/2012/009249, Office Action dated Feb. 5, 2016", W/ English Claims, 2 pgs.
"Mexican Application Serial No. MX/a/2012/009249, Office Action dated May 19, 2015", (English Translation), 1 pg.
"Mexican Application Serial No. MX/a/2012/009249, Response filed Mar. 29, 2016 to Office Action dated Feb. 5, 2016", (English Translation of Claims), 19 pgs.
"Mexican Application Serial No. PA/a/2005/011250, Office Action dated Aug. 23, 2010", W/ English Translation, 4 pgs.
"Mexican Application Serial No. PA/a/2005/011250, Response Filed Dec. 20, 2010 to Office Action dated Aug. 23, 2010", (w/ English Translation of Claims), 14 pgs.
"Mexican Application Serial No. PA/a/2005/012712 , Office Action dated Aug. 11, 2009", (English Translation), 5 pgs.
"Mexican Application Serial No. PA/a/2005/012712, Office Action dated May 12, 2010", (w/ English Translation), 19 pgs.
"Mexican Application Serial No. PA/a/2005/012712, Office Action dated Nov. 30, 2009", (w/ English Translation), 14 pgs.
"Mexican Application Serial No. PA/a/2005/012712, Official Action dated Mar. 5, 2009", (English Translation), 2 pgs.
"Mexican Application Serial No. PA/a/2005/012712, Response filed Sep. 27, 2010 to Office Action dated May 12, 2010", (w/ English Translation of Claims), 19 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 542935, Examination Report dated Feb. 25, 2008", 2 pgs.
"New Zealand Application Serial No. 542935 Examination Report dated Jun. 14, 2006" 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examinatiom Report dated Feb. 29, 2008", 2 pgs.
"New Zealand Application Serial No. 543446, Examination Report dated May 12, 2008", 2 pgs.
"New Zealand Application Serial No. 543446, Response dated Mar. 20, 2008 to Examination Report dated Feb. 29, 2008", 2 pgs.
"Nonstructural protein 1 [influenza B virus (B/Hong Kong/330/2001)]", GenBank AAT69443.1, (2006), 1 pg.
"Polymerase acidic [influenza A virus (A/swine/Shizuoka/120/97(H3N2))]", GenBank AAO15329.1, (2003), 1 pg.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
"Russian Federation Application No. 2005136233, Office Action dated Dec. 25, 2007", 2 pgs.
"Russian Federation Application No. 2005136233, Response filed May 29, 2008 to Office Action dated Dec. 25, 2007", (w/ Partial English Translation), 7 pgs.
"Russian Federation Application Serial No. 2005136233, First Office Action dated Feb. 27, 2007", (w/ English Translation), 5 pgs.
"Russian Federation Application Serial No. 2005136233, Response filed Jun. 14, 2007 to First Office Action dated Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singaporean Application Serial No. 200506858-0, Examination Report dated Feb. 9, 2007", 4 pgs.
"Singaporean Application Serial No. 200506858-0, Response filed Dec. 22, 2006 to Written Opinion dated Jul. 26, 2006", 18 pgs.
"Singaporean Application Serial No. 200506858-0, Written Opinion dated Jul. 26, 2006", 8 pgs.
"Singaporean Application Serial No. 200507468-7, Examination Report dated Mar. 19, 2008", 5 pgs.
"Singaporean Application Serial No. 200507468-7, Invitation to Respond to Written Opinion dated Jun. 12, 2007", 6 pgs.
"Singaporean Application Serial No. 200507468-7, Response filed Nov. 7, 2007 to Invitation to Respond to Written Opinion dated Jun. 12, 2007", 9 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.

(56) References Cited

OTHER PUBLICATIONS

"Ukrainian Application Serial No. 200512619, Office Action dated Feb. 27, 2009", (w/ English Translation), 21 pgs.
"Ukrainian Application Serial No. 200512619, Office Action dated Jun. 17, 2009", W/ No Translation, 3 pgs.
"Ukrainian Application Serial No. 200512619, Response filed Apr. 8, 2009 to Office Action dated Feb. 27, 2009", (w/ English Translation of Claims), 9 pgs.
Air, Gillian M., et al., "Antigenic, Sequence, and Crystal Variation in Influenza B Neuraminidase", Virology, 177(2), (1990), 578-587.
Author Unknown, "New Approaches to Influenza Vaccine", Medscape—Infections in Medicine®, © 1994-2003 by Medscape. [online]. [retrieved on Feb. 26, 2003]. Retrieved from the Internet: <URL: http://www.medscape.com/viewarticle/417404_3>, (2003), 4 pgs.
Bancroft, C. T, et al., "Evidence for segmant-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Betakova, T., et al., "The NB protein is an integral component of the membrane of influenza B virus.", J Gen Virol., 77 ( Pt 11), (Nov. 1996), 2689-94.
Bourmakina, S. V, et al., "Reverse genetics studies on the Filamentous morphology of influenza A Virus", Journal of General Virology (2003) 84,, (2003), 517-527.
Bowie, J. U., et al., "Deciphering the Message in Protein Sequences: Tolerance to Amino Acid Substitutions", Science, 247(4948), (1990), 1306-1310.
Boyer, J. C., et al., "Infectious transcripts and cDNA clones of RNA viruses". Virology, 198(2), (Feb. 1994), 415-426.
Brassard, D. L., et al., "Influenza B virus NB glycoprotein is a component of the virion", Virol., 220(2), No Document, (1996), 350-360.
Bridgen, A., "Rescue of a Segmented Negative-Strand RNA Virus Entirely From Cloned Complementary DNAs", Proc. Natl. Acad. Sci. USA, 93, (1996), 15400-15404.
Brown, E. G., et al., "Genetic analysis of mouse-adapted influenza A virus identifies roles for the NA, PB1, and PB2 genes in virulence", Virus Research, 61(1), (May 1999), 63-76.
Buchholz, U. J., et al., "Generation of Bovine Respiratory Syncytial Virus (BRSV) From cDNA: BRSV NS2 is Not Essentiial for Virus Replication in Tissue Culture, and the Human RSV Leader Region Acts as a Functional BRSV Genome Promoter", Journal of Virology, 173(1), (1999), 251-259.
Bukreyev, A., et al., "Recovery of infectious respiratory syncytial virus expressing an additional, foreign gene", Journal of Virology, 70(10), (Oct. 1996), 6634-6641.
Castrucci, Maria R., et al., "Reverse genetics system for generation of an influenza A virus mutant containing a deletion of the carboxyl-terminal residue of M2 protein.", J Virol., 69(5), (May 1995), 2725-8.
Chen, Z., et al., "Influenza A Virus NS1 Protein Targets Poly(A)-Binding Protein II of the Cellular 3'-End Processing Machinery", The EMBO Journal, 18(8), (1999), 2273-2283.
Clarke, D. K., et al., "Rescue of Mumps Virus From cDNA", Journal of Virology, 74(10), (2000), 4831-4838.
Collins, P. L., et al., "Chapter 41—Parainfluenza Viruses", In: Fields Virology, edited by Fields, B. N., et al. (3rd Edition, 1996, Lippincott-Raven Publishers, Philadelphia, PA, 1205-1241.
Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.
Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.
Conzelmann, K-K., "Genetic Engineering of Animal RNA Viruses", Trends in Microbiology, 4(10), (1996), 386-393.
Conzelmann, K.-K., "Genetic manipulation of non-segmented negative-strand RNA viruses", Journal of General Virology, 77(Pt. 3), (Mar. 1996), 381-389.
Conzelmann, K.-K., "Nonsegmented Negative-Strand RNA Viruses: Genetics and Manipulation of Viral Genomes", Annu. Rev. Genet., 32, (1998), 123-162.
Conzelmann, K.-K., "Rescue of Synthetic Genomic RNA Analogs of Rabies Virus by Plasmid-Encoded Proteins", Journal of Virology, 68(2), (1994), 713-719.
De, B. P., et al., "Requirements and Functions of Vesicular Stomatitis Virus L and NS Proteins in the Transcription Process in Vitro", Biochemical and Biophysical Research Communications, 126(1) (1985), 40-49.
De, B. P., et al., "Rescue of synthetic analogs of genome RNA of human parainfluenza virus type 3", Virology, 196(1), (Sep. 1993), 344-348.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.
De La Luna, S., et al., "Influenza Virus NS1 Protein Enhances the Rate of Translation Initiation of Viral mRNAs", Journal of Virology, 69(4), (1995), 2427-2435.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P., et al., "Recovery of infectious human parainfluenza virus type 3 from cDNA", Virology, 235(2), (Sep. 1, 1997), 323-332.
Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, M., "An influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Fahey, J. L., "Status of Immune-Based Therapies in HIV Infection and Aids", Clinincal and Experimental Immunology, 88(1), (1992), 1-5.
Fischer, W. B, et al., "Viral ion channels: structure and function.", Biochim Biophys Acta., 1561(1), (Mar. 19, 2002), 27-45.
Fodor, E., et al., "Rescue of Influenza A Virus from Recombinant DNA", Journal of Virology, 73(11), XP002151487; ISSN:0022-538X, (Nov. 1999), 9679-9682.

(56) References Cited

OTHER PUBLICATIONS

Forbes, Nicole E, et al., "Multifunctional Adaptive NS1 Mutations Are Selected upon Human Influenza Virus Evolution in the Mouse", Plos One, vol. 7, No. 2, (Feb. 21, 2012).

Fortes, P., et al., "Influenza Virus NS1 Protein Inhibits Pre-mRNA Splicing and Blocks mRNA Nucleocytoplasmic Transport", The EMBO Journal, 13(3), (1994), 704-712.

Garcia-Sastre, A., et al., "Genetic Manipulation of Negative-Strand RNA Virus Genomes", Annu. Rev. Microbiol., 47, (1993), 765-790.

Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.

Giddings, A M, et al., "The matrix protein of HIV-1 is not sufficient for assembly and release of virus-like particles", Virology, 248(1), (1998), 108-16.

Gotea, V, et al., "The functional relevance of somatic synonymous mutations in melanoma and other cancers", Pigment Cell & Melanoma Research, 28 issue 6, (Nov. 1, 2015), 673-686.

Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.

Grambas, S., et al., "Influence of amantadine resistance mutations on the pH regulatory function of the M2 protein of influenza A viruses", Virology, 191(2), (Dec. 1992), 541-549.

Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.

Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73(4), (1999), 2921-2929.

Hatada, E., et al., "Binding of Influenza A Virus NS1 Protein to dsRNA in vitro", Journal of General Virology, 73, (1992), 3325-3329.

Hatta, M., et al., "The NB protein of influenza B virus is not necessary for virus replication in vitro", Journal of Virology, 77(10), (May 2003), 6050-6054.

Hay, A. J., et al., "The role of the M2 protein in influenza A virus infection", Proceedings of the International Conference on Options for the Control of Influenza, Courchevel, (1992), 281-288.

He, B., et al., "Recovery of infectious SV5 from cloned DNA and expression of a foreign gene", Virology, 237(2), (1997), 249-260.

Helenius, A., "Unpacking the Incoming Influenza Virus", Cell, 69, (May 1992), pp. 577-578.

Hevey, Michael, et al., "Marburg virus vaccines based upon alphavirus replicons protect guinea pigs and nonhuman primates", Virology, 251(1), (Nov. 10, 1998), 28-37.

Hiromoto, Y., et al., "Phylogenetic Analysis of the Three Polymerase Genes (PB1, PB2 and PA) of Influenza B Virus", Journal of General Virology, 81, (Apr. 2000), 929-937.

Hoffman, M. A., et al., "An Infectious Clone of Human Parainfluenza Virus Type 3", Journal of Virology, 71(6), (1997), 4272-4277.

Holsinger, L. J., et al., "Influenza A Virus M2 Ion Channel Protein: a Structure-Function Analysis", Journal of Virology, 68 (3), (1994), pp. 1551-1563.

Horimoto, T., et al., "Enhanced growth of seed viruses for H5N1 influenza vaccines", Virology, 366(1), (Sep. 15, 2007), 23-27.

Huang, T.-S., et al., "Determination of Influenza Virus Proteins Required for Genome Replication", Journal of Virology, 64(11), (1990), 5669-5673.

Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.

Jackson, D., et al., "A reverse genetics approach for recovery of recombinant influenza B viruses entirely from cDNA.", J Virol., 76(22), (Nov. 2002), 11744-7.

Jang, S.-W., et al., "Deoxygedunin, a Natural Product with Potent Neurotrophic Activity in Mice", PLoS ONE 5(7): e11528, (2010), 1-15.

Jasenosky, Luke D, et al., "Ebola Virus VP40-Induced Particle Formation and Association with the Lipid Bilayer", Journal of Virology, 75 (110, (Jun. 2001), 5205-5214.

Kaplan, G., et al., "In vitro Synthesis of Infectious Poliovirus RNA", Proc. Natl. Acad. Sci. USA, 82, (1985), 8824-8428.

Kato, A., et al., "Initiation of Sendai Virus Multiplication From Transfected cDNA or RNA With Negative or Positive Sense", Genes to Cells, 1, (1996), 569-579.

Kawaoka, Y., "Mutant Cells With Altered Sialic Acid", U.S. Appl. No. 11/644,179, filed Dec. 22, 2006, 51 pgs.

Kimura, N., et al., "An In Vivo Study of the Replication Origin in the Influenza Virus Complementary RNA", The Journal of Biochemistry, 113(1), (1993), 88-92.

Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.

Kistner, Otfried, et al., "Cell culture (Vero) derived whole virus (H5N1) vaccine based on wild-type virus strain induces cross-protective immune responses", Vaccine, 25(32), (2007), 6028-6036.

Kobayashi, M., et al., "Reconstitution of Influenza Virus RNA Polymerase From Three Subunits Expressed Using Recombinant Baculovirus System", Virus Research, 22, (1992), 235-245.

Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.

Konarska, M. M., et al., "Structure of RNAs Replicated by the DNA-Dependent T7 RNA Polymerase", Cell, 63(2), (1990), 609-618.

Kovacova, A., et al., "Sequence similarities and evolutionary relationships of influenza virus A hemagglutinins.", Virus Genes, 24(1), (2002), 57-63.

Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.

Krystal, M., "Influenza B/Lee/40, hemagglutinin (seg 4), complete segment.", Database EM_VI E.B.I. Hinxton U.K., (Apr. 25, 1990).

Kunkel, T. A., "Rapid and Efficient Site-Specific Mutagenesis Without Phenotypic Selection", Proc. Natl. Acad. Sci. USA, 82, (1985), 488-492.

Lawson, N. D., "Recombinant Vesicular Stomatitis Viruses From DNA", Proc. Natl. Acad. Sci. USA, 92(10), (1995), 4477-4481.

Lee, M. S, et al., "Genetic and pathogenic characterization of H6NI avian influenza viruses isolated in Taiwan between 1972 and 2005", Avian Diseases, 50(4), (Dec. 2006), 561-571.

Levis, R., et al., "Deletion Mapping of Sindbis Virus DI RNAs Derived From cDNAs Defines the Sequences Essential for Replication and Packaging", Cell, 44, (1986), 137-145.

Li, et al., "Genesis of a highly pathogenic and potentially pandemic H5N1 influenza virus in eastern Asia" (2004), 209-213 pgs.

Li, K. S, et al., "Genesis of a highly pathogenic and potentially pandemic H5NI influenza virus in eastern Asia", Nature, 430(6996), (Jul. 8, 2004), 209-213.

Li, Y, et al., "Viral liposomes released from insect cells infected with recombinant baculovirus expressing the matrix protein of vesicular stomatitis virus", Journal of Virology, 67 (7), 1(1993), 4415-4420.

Lin, Y P, et al., "Adaptation of egg-grown and transfectant influenza viruses for growth in mammalian cells: selection of hemagglutinin mutants with elevated pH of membrane fusion", Virology, vol. 233, No. 2, (1997), 402-410.

Lugovtsev, V. Y., et al., "Genetic Composition and Mutational Pattern of Influenza B Viruses Adapted to Replication in Embryonated Eggs", GenBank: AAT69446.1, (2005), 1 pg.

Luo, M., "Inhibitors of Influenza Virus Neuraminidase", Abstract No. WO296, from a paper presented at the Annual Meeting of the

(56) References Cited

OTHER PUBLICATIONS

American Crystallographic Association, ihttp://www.hwi.buffalo.edu/ACA/ACA98/abstracts/text/WO296.html, (Observed Feb. 27, 2003), 1 pg.
Luytjes, W., "Amplification, Expression, and Packaging of a Foreign Gene by Influenza Virus", Cell, 59(6), (1989), 1107-1113.
Mark, A, et al., "Effect of Mutations and Deletions in a Bicistronic mRNA on the Synthesis of Influenza B Virus NB and NA Glycoproteins", Journal of Virology, vol. 77, No. 10, (May 2003), 6050-6054.
McKimm, J. L., et al., "Mutations in a Conserved Residue in the Influenza Virus (Neuraminidase Active Site Decreases Sensitivity to Neu5Ac2en-Derived Inhibitors", Journal of Virology, 72(3), (1998), 2456-2462.
Mebatsion, Teshome, et al., "Budding of Rabies Virus Particles in the Absence of the Spike Glycoprotein", Cell, 84(6), (1996), 941-951.
Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.
Mena, I., "Rescue of a Synthetic Choramphenicol Acetyltransferase RNA into influenza Virus-Like Particles obtained from recombinant plasmids", Journal of Virology, 70(8), (1996), 5016-5024.
Mena, I., et al., "Synthesis of Biologically Active Influenza Virus Core Proteins Using a Vaccinia Virus-T7 RNA Polymerase Expression System", Journal of General Virology, 75, (1994), 2109-2114.
Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.
Moyer, S. A., et al., "Assembly and Transcription of Synthetic Vesicular Stomatitis Virus Nucleocapsids", Journal of Virology, 65(5), (1991), 2170-2178.
Murakami, Shin, et al., "Growth Determinants for H5N1 Influenza Vaccine Seed Viruses in MDCK Cells", Journal of Virology, vol. 82, No. 21, (Nov. 2008), 10502-10509.
Naito, S., et al., "Function and Structure of RNA Polymerase From Vesicular Stomatitis Virus", The Journal of Biological Chemistry, 251(14), (1976), 4307-4314.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza A vaccine based on the extracellular domain of the M2 protein", Nature Medicine, 5 (10), (Oct. 1999), pp. 1157-1163.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "An Improved Reverse Genetics System for Influenza A Virus Generation and Its Implications for Vaccine Production", Proc. Natl. Acad. Sci. USA, 102(46), (2005), 16825-16829.
Neumann, G., et al,, "Emergence and pandemic potential of swine-origin HIN1 influenza virus", Nature (London), 459(7249), (Jun. 2009), 931-939.
Neumann, G., et al., "Reverse Genetics of Influenza Viruses—Applications in Research and Vaccine Design", Monographs in Virology, 27, (2008), 118-133.
Neumann, G., et al., "RNA Polymerase I-Mediated Expression of Influenza Viral RNA Molecules", Virology, 202(1), (1994), 477-479.
Neumann, Gabriele, et al., "Reverse Genetics Demonstrates that Proteolytic Processing of the Ebola Virus Glycoprotein Is Not Essential for Replication in Cell Culture", Journal of Virology, 76 (1) (Jan. 2002) 406-410.
Palese, P., "Negative-Strand RNA Viruses: Genetic Engineering and Applications", Proc. Natl. Acad. Sci. USA, 93(21), (1996), 11354-11358.
Park, Eun K., et al., "The M2 Ectodomain is important for its incorporation into influenza A virions", J. of Virology, vol. 72, No. 3, XP002196797, (Mar. 1998), 2449-2455.
Park, K. H., et al., "Rescue of a Foreign Gene by Sendai Virus", Proc. Natl. Acad. Sci. USA, 88, (1991), 5537-5541.
Pattnaik, A. K., et al,, "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.
Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.
Pekosz, A., "Commentary—Reverse Genetics of Negative-Strand RNA Viruses: Closing the Circle", Proc. Natl. Acad. Sci. USA, 96, (1999), 8804-8806.
Pekosz, A., et al., "Influenza C virus CM2 integral membrane glycoprotein is produced from a polypeptide precursor by cleavage of an internal signal sequence", PNAS, vol. 95, XP002196653,(Oct. 1998), 13233-13238.
Percy, N., et al., "Expression of a Foreign Protein by Influenza A Virus", Journal of Virology, 68(7), (1994), 4486-4492.
Piller, S C., et al., "Vpr protein of human immunodeficiency virus type 1 forms cation-selective channels in planar lipid bilayers", PNAS, 93, (1996), 111-1115.
Pinto, L. H., et al., "Influenza Virus M2 Protein Has Ion Channel Activity", Cell, 69, (May 1992), pp. 517-528.
Pleschka, S., et al., "A Plasmid-Based Reverse Genetics System for Influenza A Virus", Journal of Virology, 70(6), (1996), 4188-4192.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981).
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Roberts, A., et al., "Minireview—Recovery of Negative-Strand RNA Viruses From Plasmid DNAs: A Positive Approach Revitalizes a Negative Field", Virology, 247(1), (1998), 1-6.
Romanova, J., et al., "Live cold-adapted influenza A vaccine produced in Vero cell line", Virus Research, 103, (2004), 187-193.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Ruigrok, R W, et al., "Structural Characterization and Membrane Binding Properties of the Matrix Protein VP40 of Ebola Virus", Journal of Molecular Biology, 300(1), (2000), 103-112.
Sansom, M. S., et al., "Influenza virus M2 Protein: a molecular modelling study of the ion channel", Protein Engineering, 6 (1), (1993), pp. 65-74.
Schlesinger, S., "RNA Viruses as Vectors for the Expression of Heterologous Proteins", Molecular Biotechnology, 3(2), (1995), 155-165.
Schnell, M. J., "Infectious Rabies Viruses From Cloned cDNA", The EMBO Journal, 13(18), (1994), 4195-4203.
Schnell, Matthias J, et al., "Requirement for a non-specific glycoprotein cytoplasmic domain sequence to drive efficient budding of vesicular stomatitis virus", EMBO Journal, 17 (5), (1998), 1289-1296.
Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.

(56) References Cited

OTHER PUBLICATIONS

Sidhu, M. S., et al., "Rescue of Synthetic Measles Virus Minireplicons: Measles Genomic Termini Direct Efficient Expression and Propagation of a Reporter Gene", Virology, 208, (1995), 800-807.
Skehel, J. J., et al., "On the Mechanism of Inhibition of Influenza Virus Replication by Amantadine Hydrochloride", The Journal of General Virology, 38 (1), (1977), pp. 97-110.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Sugrue, R. J., et al., "Specific structural alteration of the influenza haemagglutinin by amantadine", The EMBO Journal, 9 (11), (1990), pp. 3469-3476.
Sugrue, R. J., et al.. "Structural Characteristics of the M2 Protein of Influenza A Viruses: Evidence That It Forms a Tetrameric Channel", Virology, 180, (1991), pp. 617-624.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.
Taylor, J., et al., "Newcastle Disease Virus Fusion Protein Expressed in a Fowlpox Virus Recombinant Confers Protection in Chickens", Journal of Virology, 64(4), (1990), 1441-1450.
Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.
Wagner, R., et al., "Interdependence of hemagglutinin glycosylation and neuraminidase as regulators of influenza virus growth: a study by reverse genetics", Journal of Virology, 74 (14), (Jul. 2000), 6316-6323.
Wang, C., et al., "Ion Channel Activity of Influenza A Virus M2 Protein: Characterization of the Amantadine Block", Journal of Virology, 67 (9), (Sep. 1993), pp. 5585-5594.
Ward, C. D., et al., "Direct Measurement of the Poliovirus RNA Polymerase Error Frequency In Vitro", Journal of Virology, 62(2), (1988), 558-562.
Watanabe, S., et al., "Influenza A Virus Lacking M2 Protein as a Live Attenuated Vaccine", Journal of Virology, 83(11), (2009), 5947-5950.
Watanabe, T., et al., "Influenza A Virus with Defective M2 Ion Channel Activity as a Live Vaccine", Virology, 299(2), (Aug. 1, 2002), 266-270.

Whelan, S. P. J., et al., "Efficient Recovery of Infectious Vesicular Stomatitis Virus Entirely from cDNA Clones", Proc. Natl. Acad. Sci. USA, 92, (1995), 8388-8392.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wilson, Julie A, et al., "Epitopes Involved in Antibody-Mediated Protection from Ebola Virus", Science, 287, (Mar. 2000), 1664-1666.
Wu, Rui, et al., "A live bivalent influenza vaccine based on a H9N2 virus strain", Vaccine, 128, (2010), 673-680.
Xu, X., et al., "Reassortment and evolution of current human influenza A and B viruses", Virus Research, 103, (2004), 55-60.
Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.
Yusoff, K., et al., "Nucleotide Sequence Analysis of the L Gene of Newcastle Disease Virus: Homologies With Sendai and Vesicular Stomatitits Viruses", Nucleic Acids Research, 15(10), (1987), 3961-3976.
Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.
Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.
Zebedee, S. L, et al., "Characterization of the Influenza Virus M2 Integral Membrane (Protein and Expression at the Infected-Cell Surface from Cloned cDNA", Journal of Virology, 56(2) (Nov. 1985), 502-511.
Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.
Zobel, A., et al., "RNA Polymerase I Catalysed Transcription of Insert Viral cDNA", Nucleic Acids Research, 21(16), (1993), 3607-3614.
U.S. Appl. No. 11/729,557, filed Mar. 29, 2007, High Titer Recombinant Influenza Viruses for Vaccines, now U.S. Pat. No. 9,254,318.
U.S. Appl. No. 14/332,121, filed Jul. 15, 2014, High Titer Recombinant Influenza Viruses With Enhanced Replication in MDCK or Vero Cells or Eggs.
U.S. Appl. No. 15/593,039, filed May 11, 2017, High Titer Recombinant Influenza Viruses With Enhanced Replication in MDCK or Vero Cells or Eggs.
U.S. Appl. No. 14/745,236, filed Jun. 19, 2015, Mutations That Confer Genetic Stability to Additional Genes in Influenza Viruses.

A/PR/8/34 (H1N1)

$10^{10}$ EID$_{50}$/ml
HA titer: 1:8,000

$10^{10}$ EID$_{50}$/ml
HA titer: 1:3,200

GROWTH OF REASSORTANT H5N1 VIRUSES POSSESSING PR8(UW) OR PR8(CAMBRIDGE) INTERNAL GENES IN CHICKEN EMBRYONATED EGGS

| | PA | PB1 | PB2 | HA | NP | NA | M | NS | LOG$_{10}$EID$_{50}$/ml |
|---|---|---|---|---|---|---|---|---|---|
| PR8(UW)/1194 | R | R | R | G | R | G | R | R | 9.07 ± 0.37 |
| PR8(UW)/1194–CamPA | B | R | R | G | R | G | R | R | 8.88 ± 0.25 |
| PR8(UW)/1194–CamPB1 | R | B | R | G | R | G | R | R | 9.08 ± 0.38 |
| PR8(UW)/1194–CamPB2 | R | R | B | G | R | G | R | R | 9.05 ± 0.40 |
| PR8(UW)/1194–CamNP | R | R | B | G | B | G | R | R | 9.00 ± 0.20 |
| PR8(UW)/1194–CamPB12 | R | B | B | G | R | G | R | R | 8.75 ± 0.25 |
| PR8(UW)/1194–CamP3 | B | B | B | G | R | G | R | R | 8.56 ± 0.13* |
| PR8(UW)/1194–CamP3NP | B | B | B | G | B | G | R | R | 8.19 ± 0.31* |
| NIBRG–14 | B | B | B | G | B | G | B | B | 8.32 ± 0.20* |

| R | B | G |
|---|---|---|
| PR8(UW) | PR8(CAMBRIDGE) | A/VIETNAM/1194/2004 |

FIG. 7

THE EFFECT OF THE M AND NS GENES ON THE GROWTH OF
VIRUSES IN CHICKEN EMBRYONATED EGGS

| |

GROWTH RATES IN MDCK CELL OF REASSORTANTS WITH DIFFERENT HA, NA, AND NS GENES

| | PA | PB1 | PB2 | HA | NP | NA | M | NS | $\times 10^8$ PFU/ml |
|---|---|---|---|---|---|---|---|---|---|
| PR8(UW)/1194 | R | R | R | G1 | R | G1 | R | R | 0.39 ± 0.21 |
| PR8(UW)/1203 | R | R | R | G2 | R | G2 | R | R | 0.40 ± 0.20 |
| PR8(UW)/1203/03FILL | R | R | R | G2 | R | Y | R | R | 1.26 ± 0.47* |
| PR8(UW)/1203/HK213 | R | R | R | G2 | R | BR | R | R | 1.10 ± 0.37* |
| PR8(UW)/1203/03FILL–CamNS | R | R | R | G2 | R | Y | R | B | 2.33 ± 0.27** |
| PR8(UW)/1203/HK213–CamNS | R | R | R | G2 | R | BR | R | B | 2.35 ± 0.21** |

33°C, 36 hpi, moi=0.01

R — PR8(UW)
G1 — A/VIETNAM/1194/2004
Y — VN1203FILL (1203 WITH LONGER STALK)
B — PR8(CAMBRIDGE)
G2 — A/VIETNAM/1203/2004 (1203)
BR — A/HONG KONG/213

FIG. 13

```
                              PB8(Cambridge)
PB2
AGCGAAAGCAGGTCAATTATATTCAATATGGAAAGAATAAAAGAACTAAGAAATCTAATGTCGCAGTCTCGCACCCGCGAGATA
CTCACAAAAACCACCGTGGACCATATGGCCATAATCAAGAAGTACACATCAGGAAGACAGGAGAAGAACCCAGCACTTAGGATG
AAATGGATGATGGCAATGAAATATCCAATTACAGCAGACAAGAGGATAACGGAAATGATTCCTGAGAGAAATGAGCAAGGACAA
ACTTTATGGAGTAAAATGAATGATGCCGGATCAGACCGAGTGATGGTATCACCTCTGGCTGTGACATGGTGGAATAGGAATGGA
CCAATGACAAATACAGTTCATTATCCAAAAATCTACAAAACTTATTTTGAAAGAGTCGAAAGGCTAAAGCATGGAACCTTTGGC
CCTGTCCATTTTAGAAACCAAGTCAAAATACGTCGGAGAGTTGACATAAATCCTGGTCATGCAGATCTCAGTGCCAAGGAGGCA
CAGGATGTAATCATGGAAGTTGTTTTCCCTAACGAAGTGGGAGCCAGGATACTAACATCGGAATCGCAACTAACGATAACCAAA
GAGAAGAAAGAAGAACTCCAGGATTGCAAAATTTCTCCTTTGATGGTTGCATACATGTTGGAGAGAGAACTGGTCCGCAAAACG
AGATTCCTCCCAGTGGCTGGTGGAACAAGCAGTGTGTACATTGAAGTGTTGCATTTGACTCAAGGAACATGCTGGGAACAGATG
TATACTCCAGGAGGGGAAGTGAAGAATGATGATGTTGATCAAAGCTTGATTATTGCTGCTAGGAACATAGTGAGAAGAGCTGCA
GTATCAGCAGACCCACTAGCATCTTTTATTGGAGATGTGCCACAGATTGGTGGAATTAGGATGGTAGACATCCTTAAG
CAGAACCCAACAGAAGACAAGCCGTGGATATATGCAAGGCTGCAATGGGACTGAGAATTAGCTCATCCTTCAGTTTTGGTGGA
TTCACATTTAAGAGAACAAGCGGATCATCAGTCAAGAGAGGAAGAGGTGCTTACGGGCAATCTTCAAACATTGAAGATAAGA
GTGCATGAGGGATCTGAAGAGTTCACAATGGTTGGGAGAAGAGCAACAGCCATACTCAGAAAAGCAACCAGGAGATTGATTCAG
CTGATAGTGAGTGGGAGAGCAACAGTCGATTGCCGAAGCAATAATTGTGGCCATGGTATTTTCACAAGAGGATTGTATGATA
AAAGCAGTTAGAGGTGATCTGAATTTCGTCAATAGGGCGAATCAGCGACTGAATCCTATGCATCAACTTTTAAGACATTTTCAG
AAGGATGCGAAAGTGCTTTTTCAAAATTGGGGAGTTGAACCTATCGACAATGTGATGGGAATGATTGGGATATTGCCCGACATG
ACTCCAAGCATCGAGATGTCAATGAGAGGAGTGAGAATCAGCAAAATGGGTGTAGATGAGTACTCCAGCACGGAGAGGGTAGTG
GTGAGCATTGACCGGTTCTTGAGAGTCAGGGACCAACGAGGAAATGTACTACTGTCTCCCGAGGAGGTCAGTGAAACACAGGGA
ACAGAGAAACTGACAATAACTTACTCATCGTCAATGATGTGGGAGATTAATTGGTCCTGAATCAGTGTTGGTCAATACCTATCAA
TGGATCATCAGAAACTGGGAAACTGTTAAAATTCAGTGGTCCCAGAACCCTACAATGCTATACAATAAAATGGAATTTGAACCA
TTTCAGTCTTTAGTACCTAAGGCCATTAGAGGCCAATACACTGGGTTTGTAAGAACTCTGTTCCAACAAATGAGGGATGTGCTT
GGGACATTTGATACCGCACAGATAATAAAACTTCTTCCCTTCGCAGCCGCTCCACCAAAGCAAAGTAGAATGCAGTTCTCCTCA
TTTACTGTGAATGTGAGGGGATCAGGAATGAGAATACTTGTAAGGGGCAATTCTCCTGTATTCAACTACAACAAGGCCACGAAG
AGACTCACAGTTCTCGGAAAGGATGCTGGCACTTTAACCGAAGACCCAGATGAAGGCACAGCTGGAGTGGAGTCCGCTGTTCTG
AGGGGATTCCTCATTCTGGGCAAAGAAGACAGGAGATATGGGCCAGCATTAAGCATCAATGAACTGAGCAACCTTGCGAAAGGA
GAGAAGGCTAATGTGCTAATTGGGCAAGGAGACGTGGTGTTGGTAATGAAACGAAAACGGGACTCTAGCATACTTACTGACAGC
CAGACAGCGACCAAAAGAATTCGGATGGCCATCAATTAGTGTCGAATAGTTTAAAAACGACCTTGTTTCTACT
                                                            SEQ ID NO. 33

PB1
AGCGAAAGCAGGCAAACCATTTGAATGGATGTCAATCCGACCTTACTTTTCTTAAAAGTGCCAGCACAAAATGCTATAAGCACA
ACTTTCCCTTATACCGGAGACCCTCCTTACAGCCATGGGACAGGAACAGGATACACCATGGATACTGTCAACAGGACACATCAG
TACTCAGAAAAGGGAAGATGGACAACAAACACCGAAACTGGAGCACCGCAACTCAACCCGATTGATGGGCCACTGCCAGAAGAC
AATGAACCAAGTGGTTATGCCCAAACAGATTGTGTATTGGAAGCAATGGCTTTCCTTGAGGAATCCCATCCTGGTATTTTTGAA
AACTCGTGTATTGAAACGATGGAGGTTGTTCAGCAAACACGAGTAGACAAGCTGACACAAGGCCGACAGACCTATGACTGGACT
TTAAATAGAAACCAGCCTGCTGCAACAGCATTGGCCAACACAATAGAAGTGTTCAGATCAAATGGCCTCACGGCCAATGAGTCA
GGAAGGCTCATAGACTTCCTTAAGGATGTAATGGAGTCAATGAAAAAAGAAGAAATGGGGATCACAACTCATTTTCAGAGAAAG
AGACGGGTGAGAGACAATATGACTAAGAAAATGATAACACAGAGAACAATAGGTAAAAGGAAACAGAGATTGAACAAAAGGGGT
TATCTAATTAGAGCATTGACCCTGAACACAATGACCAAAGATGCTGAGAGGGGAAGCTAAAACAGGAGAGCAATTGCAACCCA
GGGATGCAAATAAGGGGGTTTGTATACTTTGTTGAGACACTGGCAAGGAGTATATGTGAGAAACTTGAACAATCAGGGTTGCCA
GTTGGAGGCAATGAGAAGAAAGCAAAGTTGGCAAATGTTGTAAGGAAGATGATGACCAATTCTCAGGACACCGAACTTTCTTTC
ACCATCACTGGAGATAACACCAAATGGAACGAAAATCAGAATCCTCGGATGTTTTTGGCCATGATCACATATATGACCAGAAAT
CAGCCCGAATGGTTCAGAAATGTTCTAAGTATTGCTCCAATAATGTTCTCAAACAAAATGGCGGGACTGGGAAAAGGGTATATG
TTTGAGAGCAAGAGTATGAAACTTAGAACTCAAATACCTGCAGAAATGCTAGCAAGCATTGATTTGAAATATTTCAATGATTCA
ACAAGAAAGAAGATTGAAAAAATCCGACCGCTCTTAATAGAGGGGACTGCATCATTGAGCCCTGGAATGATGATGGGCATGTTC
AATATGTTAAGCACTGTATTAGGCGTCTCCATCCTGAATCTTGGACAAAAGAGATACACCAAGACTACTTACTGGTGGGATGGT
CTTCAATCCTCTGACGATTTTGCTCTGATTGTGAATGCACCCAATCATGAAGGGATTCAAGCCGGAGTCGACAGGTTTTATCGA
ACCTGTAAGCTACTTGGAATCAATATGAGCAAGAAAAAGTCTTACATAAACAGAACAGGTACATTTGAATTCACAAGTTTTTTC
TATCGTTATGGGTTTGTTGCCAATTTCAGCATGGAGCTTCCCAGTTTTGGGGTGTCTGGGATCAACGAGTCAGCGGACATGAGT
ATTGGAGTTACTGTCATCAAAAACAATATGATAAACAATGATCTTGGTCCAGCAACAGCTCAAATGGCCCTTCAGTTGTTCATC
AAAGATTACAGGTACACGTACCGATGCCATAGAGGTGACACACAAATACAAACCCGAAGATCATTTGAAATAAAGAAACTGTGG
GAGCAAACCCGTTCAAAGGCTGGACTGCTGGTCTCCGACGGAGGCCCAAATTTATACAACATTAGAAATCTCCACATTCCTGAA
GTCTGCCTAAAATGGGAATTGATGGATGAGGATTACCAGGGGCGTTTATGCAACCCACTGAACCCATTTGTCAGCCATAAAGAA
ATTGAATCAATGAACAATGCAGTGATGATGCCAGCACATGGTCCAGCAAAAAACATGGAGTATGATGCTGTTGCAACAACACAC
TCCTGGATCCCCAAAAGAAATCGATCCATCTTGAATACAAGTCAAAGAGGAGTACTTGAAGATGAACAAATGTACCAAAGGTGC
TGCAATTTATTTGAAAAATTCTTCCCCAGCAGTTCATACAGAAGACCAGTCGGGATATCCAGTATGGTGGAGGCTATGGTTTCC
AGAGCCCGAATTGATGCACGGATTGATTTCGAATCTGGAAGGATAAAGAAAGAAGAGTTCACTGAGATCATGAAGATCTGTTCC
ACCATTGAAGAGCTCAGACGGCAAAAATAGTGAATTTAGCTTGTCCTTGTCATGAAAAAATGCCTTGTTTCTACT
                                                            SEQ ID NO. 34
```

*FIG. 15A*

PR8 (cambridge)

PA

AGCGAAAGCAGGTACTGATTCAAAATGGAAGATTTTGTGCGACAATGCTTCAATCCGATGATTGTCGAGCTTGCGGAAAAAACA
ATGAAAGAGTATGGGGAGGACCTGAAAATCGAAACAAACAAATTTGCAGCAATATGCACTCACTTGGAAGTATGCTTCATGTAT
TCAGATTTCCACTTCATCAATGAGCAAGGCGAGTCAATAATCGTAGAACTTGGTGATCCTAATGCACTTTTGAAGCACAGATTT
GAAATAATCGAGGGAAGAGATCGCACAATGGCCTGGACAGTAGTAAACAGTATTTGCAACACTACAGGGGCTGAGAAACCAAAG
TTTCTACCAGATTTGTATGATTACAAGGAAAATAGATTCATCGAAATTGGAGTAACAAGGAGAGAAGTTCACATATACTATCTG
GAAAAGGCCAATAAAATTAAATCTGAGAAAACACACATCCACATTTTCTCGTTCACTGGGGAAGAAATGGCCACAAGGGCCGAC
TACACTCTCGATGAAGAAAGCAGGGCTAGGATCAAAACCAGGCTATTCACCATAAGACAAGAAATGGCCAGCAGAGGCCTCTGG
GATTCCTTTCGTCAGTCCGAGGAGGAGAAGAGACAATTGAAGAAAGGTTTGAAATCACAGGAACAATGCGCAAGCTTGCCGAC
CAAAGTCTCCCGCCGAACTTCTCCAGCCTTGAAAATTTTTAGAGCCTATGTGGATGGATTCGAACCGAACGGCTACATTGAGGGC
AAGCTGTCTCAAATGTCCAAAGAAGTAAATGCTAGAATTGAACCTTTTTTGAAAACAACACCACGACCACTTAGACTTCCGAAT
GGGCCTCCCTGTTCTCAGCGGTCCAAATTCCTGCTGATGGATGCCTTAAAATTAAGCATTGAGGACCCAAGTCATGAAGGAGAG
GGAATACCGCTATATGATGCAATCAATCAAACATCATGAGAACATTCTTTTGGATGGAAGGAACCCAATGTTGTTAAACCACACGAAAAG
GGAATAAATCCAAATTATCTTCTGTCATGGAAGCAAGTACTGGCAGAACTGCAGGACATTGAGAATGAGGAGAAAATTCCAAAG
ACTAAAAATATGAAAAAAACAAGTCAGCTAAAGTGGGCACTTGGTGAGAACATGGCACCAGAAAAGGTAGACTTTGACGACTGT
AAAGATGTAGGTGATTTGAAGCAATATGATAGTGATGAACCAGAATTGAGGTCGCTTGCAAGTTGGATTCAGAATGAGTTCAAC
AAGGCATGCGAACTGACAGATTCAAGCTGGATAGAGCTTGATGAGATTGGAGAAGATGTGGCTCCAATTGAACACATTGCAAGC
ATGAGAGGAATTATTTCACATCAGAGGTGTCTCACTGCAGAGCCACAGAATACATAATGAAGGGGGTGTACATCAATACTGCC
TTACTTAATGCATCTTGTGCAGCAATGGATGATTTCCAATTAATTCCAATGATAAGCAAGTGTAGAACTAAGGAGGGAAGGCGA
AAGACCAACTTGTATGGTTTCATCATAAAAGGAAGATCCCACTTAAGGAATGACACCGACGTGGTAAACTTTGTGAGCATGGAG
TTTTCTCTCACTGACCCAAGACTTGAACCACACAAATGGGAGAAGTACTGTGTTCTTGAGATAGGAGATATGCTTCTAAGAAGT
GCCATAGGCCAGGTTTCAAGGCCCATGTTCTTGTATGTGAGGACAAATGGAACCTCAAAAATTAAAATGAAATGGGGAATGGAG
ATGAGGCGTTGTCTCCTCCAGTCACTTCAACAAATTGAGAGTATGATTGAAGCTGAGTCCTCTGTCAAAGAGAAAGACATGACC
AAAGAGTTCTTTGAGAACAAATCAGAAACATGGCCCATTGGAGAGTCTCCCAAAGGAGTGGAGGAAAGTTCCATTGGGAAGGTC
TGCAGGACTTTATTAGCAAAGTCCGTATTTAACAGCTTGTATGCATCTCCACAACTAGAAGGATTTTCAGCTGAATCAAGAAAA
CTGCTTCTTATCGTTCAGGCTCTTAGGGACAATCTGGAACCTGGGACCTTTGATCTTGGGGGGCTATATGAAGCAATTGAGGAG
TGCCTAATTAATGATCCCTGGGTTTTGCTTAATGCTTCTTGGTTCAACTCCTTCCTTACACATGCATTGAGTTAGTTGTGGCAG
TGCTACTATTTGCTATCCATACTGTCCAAAAAAGTACCTTGTTTCTACT

SEQ ID NO. 35

NP

AGCAAAAGCAGGGTAGATAATCACTCACTGAGTGACATCAAAATCATGGCGTCCCAAGGCACCAAACGGTCTTACGAACAGATG
GAGACTGATGGAGAACGCCAGAATGCCACTGAAATCAGAGCATCCGTCGGAAAAATGATTGGTGGAATTGGACGATTCTACATC
CAAATGTGCACAGAACTTAAACTCAGTGATTATGAGGGACGGTTGATCCAAAACAGCTTAACAATAGAGAGAATGGTGCTCTCT
GCTTTTGACGAAAGGAGAAATAAATACCTTGAAGAACATCCCAGTGCGGGGAAAGATCCTAAGAAAACTGGAGGACCTATATAC
AGAAGAGTAAACGGAAAGTGGATGAGAGAACTCATCCTTTATGACAAAGAAGAAATAAGGCGAATCTGCGCCAAGCTAATAAT
GGTGACGATGCAACGGCTGGTCTGACTCACATGATGTACTGGCATTCCAATTTGAATGATGCAACTTATCAGAGGACAAGGGCT
CTTGTTCGCACCGGAATGGATCCCAGGATGTGCTCTCTGATGCAAGGTTCAACTCTCCCTAGGAGGCCGACGGTCT
GCAGTCAAAGGAGTTGGAACAATGGTGATGGAATTGGTCAGGATGATCAAACGTGGGATCAATGATCGGAACTTCTGGAGGGGT
GAGAATGGACGAAAAACAAGAATTGCTTATGAAAGAATGTGCAACATTCTCAAAGGGAAATTTCAAACTGCTGCACAAAAGCA
ATGATGGATCAAGTGACAGAGCCGGAACCCAGGGAGTGCTGAGTTCAAGATCTCACTTTTCTAGCACGGTCTGCACTCATA
TTGAGAGGGTCGGTTGCTCACAAGTCCTGCCTGCCTGCCTGTGTGATGGACCTGCCGTAGCCAGTGGGTACGACTTTGAAAGA
GAGGGATACTCTCTAGTCGGAATAGACCCTTTCAGACTGCTTCAAAACAGCCAAGTGTACAGCCTAATCAGACCAAATGAGAAT
CCAGCACACAAGAGTCAACTGGTGTGGATGGCATGCCATTCTGCCGCATTTGAAGATCTAAGAGTATTGAGCTTCATCAAAGGG
ACGAAGGTGCTCCAAGAGGGAAGCTTTCCACTAGAGGAGTTCAAATTGCTTCCAATGAAAATATGGAGACTATGGAATCAAGT
ACACTTGAACTGAGAACAGGTACTGGGCCATAAGGACCAGAAGTGGAGGAAACAATCAACAGAGGGCATCTGCGGGCCAA
ATCAGCATACAACCTACGTTCTCAGTACGAGAAATCTCCCTTTTGACAGAACAACCGTTATGGCAGCATTCACTGGGAATACA
GAGGGGAGAACATCTGACATGAGGACCGAAATCATAAGGATGATGGAAAGTGCAAGACCAGAAGATGTGTCTTTCCAGGGGCGG
GGAGTCTTCGAGCTCTCGGACGAAAAGGCAGCGAGCCCGATCGTGCCTTCCTTTGACATGAGTAATGAAGGATCTTATTTCTTC
GGAGACAATGCAGAGGAGTACGACAATTAAAGAAAAATACCCTTGTTTCTACT

SEQ ID NO. 36

M

AGCAAAAGCAGGTAGATATTGAAAGATGAGTCTTCTAACCGAGGTCGAAACGTACGTTCTCTCTATCATCCCGTCAGGCCCCCT
CAAAGCCGAGATCGCACAGAGACTTGAAGATGTCTTTGCAGGGAAGAACACCGATCTTGAGGTTCTCATGGAATGGCTAAAGAC
AAGACCAATCCTGTCACCTCTGACTAAGGGGATTTTAGGATTTGTGTTCACGCTCACCGTGCCCAGTGAGCGAGGACTGCAGCG
TAGACGCTTTGTCCAAAATGCCCTTAATGGGAACGGGGATCCAAATAACATGGACAGAGCAGTTAAACTGTATAGGAAGCTCAA
GAGGGAGATAACATTCCATGGGGCCAAAGAAATCTCACTCAGTTATTCTGCTGGTGCACTTGCCAGTTGTATGGGCCTCATATA
CAACAGGATGGGGGCTGTGACCACTGAAGTGGCATTTGGCCTGGTATGTGCAACCTGTGAACAGATTGCTGACTCCCAGCATCG

FIG. 15B

PR8(Cambridge)
GTCTCATAGGCAAATGGTGACAACAACCAACCCACTAATCAGACATGAGAACAGAATGGTTTTAGCCAGCACTACAGCTAAGGC
TATGGAGCAAATGGCTGGATCGAGTGAGCAAGCAGCAGAGGCCATGGAGGTTGCTAGTCAGGCTAGGCAAATGGTGCAAGCGAT
GAGAACCATTGGGACTCATCCTAGCTCCAGTGCTGGTCTGAAAAATGATCTTCTTGAAAATTTGCAGGCCTATCAGAAACGAAT
GGGGGTGCAGATGCAACGGTTCAAGTGATCCTCTCGCTATTGCCGCAAATATCATTGGGATCTTGCACTTGATATTGTGGATTC
TTGATCGTCTTTTTTTTCAAATGCATTTACCGTCGCTTTAAATACGGACTGAAAGGAGGGCCTTCTACGGAAGGAGTGCCAAAGT
CTATGAGGGAAGAATATCGAAAGGAACAGCAGAGTGCTGTGGATGCTGACGATGGTCATTTTGTCAGCATAGAGCTGGAGTAAA
AAACTACCTTGTTTCTACT

SEQ ID NO. 37

NS
AGCAAAAGCAGGGTGACAAAGACATAATGGATCCAAACACTGTGTCAAGCTTTCAGGTAGATTGCTTTCTTTGGCATGTCCGCA
AACGAGTTGCAGACCAAGAACTAGGTGATGCCCCATTCCTTGATCGGCTTCGCCGAGATCAGAAATCCCTAAGAGGAAGGGGCA
GCACTCTTGGTCTGGACATCGAGACAGCCACACGTGCTGGAAAGCAGATAGTGGAGCGGATTCTGAAAGAAGAATCCGATGAGG
CACTTAAAATGACCATGGCCTCTGTACCTGCGTCGCGTTACCTAACCGACATGACTCTTGAGGAAATGTCAAGGGAATGGTCCA
TGCTCATACCCAAGCAGAAAGTGGCAGGCCCTCTTTGTATCAGAATGGACCAGGCGATCATGGATAAAAACATCATACTGAAAG
CGAACTTCAGTGTGATTTTTGACCGGCTGGAGACTCTAATATTGCTAAGGGCTTTCACCGAAGAGGGAGCAATTGTTGGCGAAA
TTTCACCATTGCCTTCTCTTCCAGGACATACTGCTGAGGATGTCAAAAATGCAGTTGGAGTCCTCATCGGAGGACTTGAATGGA
ATGATAACACAGTTCGAGTCTCTGAAACTCTACAGAGATTCGCTTGGAGAAGCAGTAATGAGAATGGGAGACCTCCACTCACTC
CAAAACAGAAACGAGAAATGGCGGGAACAATTAGGTCAGAAGTTTGAAGAAATAAGATGGTTGATTGAAGAAGTGAGACACAAA
CTGAAGGTAACAGAGAATAGTTTTGAGCAAATAACATTTATGCAAGCCTTACATCTATTGCTTGAAGTGGAGCAAGAGATAAGA
ACTTTCTCATTTCAGCTTATTTAATAATAAAAAACACCCTTGTTTCTACT

SEQ ID NO. 38

*FIG. 15C*

HIGH TITER RECOMBINANT INFLUENZA VIRUSES FOR VACCINES

CROSS-REFERENCE TO RELATED APPLICATIONS

This application is a continuation of U.S. application Ser. No. 11/729,557, filed Mar. 29, 2007, which claims the benefit of the filing date of U.S. Application Ser. No. 60/787,766, filed Mar. 31, 2006, the disclosures of which are incorporated by reference herein.

GOVERNMENT SUPPORT

This invention was made with government support under AI044386 awarded by the National Institutes of Health. The Government has certain rights in the invention.

BACKGROUND

Negative-sense RNA viruses are classified into seven families (Rhabdoviridae, Paramnyxoviridae, Filoviridae, Bornaviridae, Orthomyxoviridae, Bunyaviridae, and Arenaviridae) which include common human pathogens, such as respiratory syncytial virus, influenza virus, measles virus, and Ebola virus, as well as animal viruses with major economic impact on the poultry and cattle industries (e.g., Newcastle disease virus and Rinderpest virus). The first four families are characterized by nonsegmented genomes, while the latter three have genomes comprised of six-to-eight, three, or two negative-sense RNA segments, respectively. The common feature of negative-sense RNA viruses is the negative polarity of their RNA genome; i.e., the viral RNA (vRNA) is complementary to mRNA and therefore is not infectious by itself. In order to initiate viral transcription and replication, the vRNA has to be transcribed into a plus-sense mRNA or cRNA, respectively, by the viral polymerase complex and the nucleoprotein; for influenza A viruses, the viral polymerase complex is comprised of the three polymerase proteins PB2, PB1, and PA. During viral replication, cRNA serves as a template for the synthesis of new vRNA molecules. For all negative-stranded RNA viruses, non-coding regions at both the 5' and 3' termini of the vRNA and cRNA are critical for transcription and replication of the viral genome. Unlike cellular or viral mRNA transcripts, both cRNA and vRNA are neither capped at the 5' end nor polyadenylated at the very 3' end.

The basic functions of many viral proteins have been elucidated biochemically and/or in the context of viral infection. However, reverse genetics systems have dramatically increased our knowledge of negative-stranded segmented and non-segmented RNA viruses with respect to their viral replication and pathogenicity, as well as to the development of live attenuated virus vaccines. Reverse genetics, as the term is used in molecular virology, is defined as the generation of virus possessing a genome derived from cloned cDNAs (for a review, see Neumann et al., 2002).

In order to initiate viral replication of negative-stranded RNA viruses, vRNA(s) or cRNA(s) must be coexpressed with the polymerase complex and the nucleoprotein. Rabies virus was the first non-segmented negative-sense RNA virus which was generated entirely from cloned cDNA: Schnell et al. (1994) generated recombinant rabies virus by cotransfection of a cDNA construct encoding the full-length cRNA and protein expression constructs for the L, P, and N proteins, all under control of the T7 RNA polymerase promoter. Infection with recombinant vaccinia virus, which provided T7 RNA polymerase, resulted in the generation of infectious rabies virus. In this T7 polymerase system, the primary transcription of the full length cRNA under control of the T7 RNA polymerase resulted in a non-capped cRNA transcript. However, three guanidine nucleotides, which form the optimal initiation sequence for T7 RNA polymerase, were attached to the 5' end. In order to create an authentic 3' end of the cRNA transcript which is essential for a productive infective cycle, the hepatitis delta ribozyme (HDVRz) sequence was used for exact autocatalytic cleavage at the 3' end of the cRNA transcript.

Since the initial report by Schnell et al. (1994), reverse genetics systems using similar techniques led to the generation of many non-segmented negative strand RNA viruses (Conzelmann, 1996; Conzelmann, 1998; Conzelmann et al., 1996; Marriott et al., 1999; Munoz et al., 2000; Nagai, 1999; Neumann et al., 2002; Roberts et al., 1998; Rose, 1996). Refinements of the original rescue procedure included the expression of T7 RNA polymerase from stably transfected cell lines (Radecke et al., 1996) or from protein expression plasmids (Lawson et al., 1995), or heat shock procedures to increase rescue efficiencies (Parks et al., 1999). Based on the T7 polymerase system, Bridgen and Elliott (1996) created Bunyamwera virus (family Bunyaviridae) from cloned cDNAs and demonstrated the feasibility of artificially generating a segmented negative-sense RNA virus by the T7 polymerase system.

In 1999, a plasmid-based reverse genetics technique was generated based on the cellular RNA polymerase I for the generation of segmented influenza A virus entirely from cloned cDNAs (Fodor et al., 1999; Neumann and Kawaoka, 1999). RNA polymerase I, a nucleolar enzyme, synthesizes ribosomal RNA which, like influenza virus RNA, does not contain 5' cap or 3' polyA structures. The RNA polymerase I transcription of a construct containing an influenza viral cDNA, flanked by RNA polymerase I promoter and terminator sequences, resulted in influenza vRNA synthesis (Fodor et al., 1999; Neumann and Kawaoka, 1999; Neumann and Kawaoka, 2001; Pekosz et al., 1999). The system was highly efficient, producing more than $10^8$ infectious virus particles per ml of supernatant of plasmid-transfected cells 48 hours post-transfection.

What is needed is a method to prepare high titer orthomyxoviruses such as influenza A virus, entirely from cloned cDNAs.

SUMMARY OF THE INVENTION

The invention provides a composition comprising a plurality of influenza virus vectors of the invention, e.g., those useful to prepare reassortant viruses including 7:1 reassortants, 6:1:1 reassortants, 5:1:2 reassortants, and 5:1:1:1 reassortants. In one embodiment of the invention, the composition includes vectors for vRNA production selected from a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a operably linked to an influenza virus NS cDNA linked to a transcription termination sequence. The composition also includes vectors for viral protein production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. Preferably, the vectors encoding viral proteins further comprise a transcription termination sequence.

In one embodiment, the cDNAs for PB1, PB2, PA, NP, M, and NS, and optionally NA, have sequences for PB1, PB2, PA, NP, M, and NS, and optionally NA, from an influenza virus that replicates to high titers in embryonated eggs, and the cDNA for HA has sequences from a different strain of influenza virus (from a heterologous influenza virus isolate with the same or a different HA subtype, i.e., a heterologous HA). For HA from pathogenic H5N1 viruses which do not grow to high titers in embryonated eggs, the cDNA for at least NA has sequences from a N1 influenza virus that replicates to high titers in embryonated eggs.

In one embodiment, the cDNAs for PB1, PB2, PA, NP, M, and NS include a nucleic acid molecule corresponding to a sequence (polynucleotide) encoding at least one of the proteins of a high titer, e.g., titers greater than $10^8$ $EID_{50}$/mL, e.g., $10^9$ $EID_{50}$/mL, $10^{10}$ $EID_{50}$/mL, or more, influenza virus. Reassortants within the scope of the invention that have high titers in embryonated eggs have titers of at least about $10^9$ $EID_{50}$/mL for 5:1:1:1 reassorants (with NS K55), 5:1:2 reassortants (with NS K55) and 6:1:1 reassortants (with NS K55) and at least $4 \times 10^8$ PFU/mL for 5:1:1:1 reassortants (with NS K55E) or 5:1:2 reassortants (with NS K55E). Reassortants within the scope of the invention that have high titers in MDCK cells have titers of at least $0.75 \times 10^8$ PFU/mL, e.g., at least $2.0 \times 10^8$ PFU/mL, for 5:1:1:1 or 6:1:1.

In one embodiment, the invention includes a composition comprising a plurality of influenza virus vectors for a 5:1:2 or a 6:1:1 reassortant. The composition includes a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence. The cDNAs for PB1, PB2, PA, NP, and M have sequences that are from one or more influenza viruses that replicate to high titers in embryonated eggs, wherein the cDNA for NS is from the one or more influenza viruses that replicate to high titers in embryonated eggs, and the cDNA for NA is from the one or more influenza viruses that replicate to high titers in embryonated eggs or has sequences for a heterologous NA. The cDNA for HA has sequences for a heterologous HA, which is heterologous to at least the viral gene segments for PB1, PB2, PA, NP, and M. In one embodiment, the cDNA for NS has a Glu at position 55. The composition also includes a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, and a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus M2, or a vector comprising a promoter operably linked to a DNA segment encoding influenza virus NS2. In one embodiment, the cDNAs for PB1, PB2, PA, NP, M, and NS include a nucleic acid molecule corresponding to a sequence (polynucleotide) encoding at least one of the proteins of a high titer, e.g., titers greater than $10^8$ $EID_{50}$/mL, e.g., $10^9$ $EID_{50}$/mL, $10^{10}$ $EID_{50}$/mL, or more, influenza virus.

In one embodiment, a composition comprising a plurality of influenza virus vectors for a 5:1:1:1 or 6:1:1 reassortant. The composition includes comprising a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence. The cDNAs for PB1, PB2, PA, NP, and M have sequences from one or more influenza viruses that replicate to high titers in MDCK cells, wherein the cDNA for NS is from the one or more influenza viruses that replicate to high titers in MDCK cells, wherein the cDNA for NA may have sequences for a heterologous NA, and wherein the cDNA for HA has sequences for a heterologous HA. The composition also includes a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, and a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus M2, or a vector comprising a promoter operably linked to a DNA segment encoding influenza virus NS2. In one embodiment, the cDNAs for PB1, PB2, PA, NP, M, and NS include a nucleic acid molecule corresponding to a sequence (polynucleotide) encoding at least one of the proteins of a high titer, e.g., titers greater than $10^8$ EID$_{50}$/mL, e.g., $10^9$ EID$_{50}$/mL, $10^{10}$ EID$_{50}$/mL, or more, influenza virus.

As described herein, recombinant (6:2 reassortant) viruses grow less well in eggs than does the wild-type PR8 strain, even though they possess the same PR8 "internal" genes (i.e., those other than the HA and NA). Since vigorous growth in eggs is an essential property of vaccine seed viruses used in the production of inactivated vaccines, H5N1 vaccine candidates were generated that grow as well as the PR8 donor strain in eggs. It was found that HA-NA balance and PB1 function are important growth determinants. With this knowledge, a series of H5N1 viruses was produced with altered HA-NA combinations, with the PR8 background, to assess their growth in eggs against more conventional 6:2 reassortants, including the WHO-recommended NIBRG-14 virus. A 7:1 reassortant virus and one of the 6:2 reassortants showed enhanced growth in eggs. Thus, for vaccine viruses that generally produce low titers in eggs, replacement of at least the NA of the vaccine virus with the NA of an influenza virus that grows well in eggs, or replacement of all but the HA and NA, or all but the HA, of the vaccine virus, with the other viral gene segments from an influenza virus that grows to high titers in eggs, can result in significantly higher viral titers. The titers of the reassortant viruses of the invention may be 2-fold, 3-fold, or greater, e.g., 7-fold or greater, than the corresponding nonreassortant vaccine virus. As also described herein, the internal genes responsible for the high growth rate of reassortants in eggs having genes from two different PR8 virus isolates was determined. The highest viral titers were those where the majority of internal genes were from PR8HG (PR8(UW)). In particular, 5:1:2 reassortants (PR8(UW) PB1, PB2, PA, NP and M; PR8(Cam) NS; and H5N1 HA and NA) and 6:1:1 reassortants (PR8(UW) NA, PB1, PB2, PA, NP and M; PR8(Cam) NS; and H5 HA) had high titers in eggs.

As also described herein, the viral genes responsible for a high growth rate in MDCK cells, cells likely to be approved as a source of vaccine virus, was assessed. The highest growth rate in MDCK cells was found with PB2 from PR8(UW), NS from PR8(Cam) or NS K55E from PR8(UW), and a NA with a long stalk, e.g., a stalk greater than 20 mino acids but less than about 100 amino acids, e.g., greater than about 40 and up to about 80 amino acids in length. Thus 5:1:1:1 and 6:1:1 reassortants with PR8(UW) PA, PB1, PB2, NP and M, and NS K55E from PR8(UW) or PR8(Cam), NA from PR8(UW) or a heterologous NA source, and a heterologous HA, grew to the highest titers in MDCK cells.

In one embodiment, the nucleic acid molecule corresponds to a sequence encoding PB1, PB2, PA, NP, M, and NS, and optionally NA, having substantially the same activity as a corresponding polypeptide encoded by one of SEQ ID NOs:1-6 or 8. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid molecule corresponds to a sequence encoding a polypeptide which is substantially the same as, e.g., having at least 80%, e.g., 90%, 92%, 95%, 97% or 99%, contiguous amino acid sequence identity to, a polypeptide encoded by one of SEQ ID NOs:1-6 or 8. In one embodiment, the isolated and/or purified nucleic acid molecule comprises a nucleotide sequence which is substantially the same as, e.g., having at least 50%, e.g., 60%, 70%, 80% or 90% or more contiguous nucleic acid sequence identity to, one of SEQ ID NOs:1-6, 8, or 33 to 38 and, in one embodiment, also encodes a polypeptide having at least 80%, e.g., 90%, 92%, 95%, 97% or 99%, contiguous amino acid sequence identity to a polypeptide encoded by one of SEQ ID NOs:1-6, 8, or 33 to 38. In one embodiment, the isolated and/or purified nucleic acid molecule encodes a polypeptide with one or more, for instance, 2, 5, 10, 15, 20 or more, conservative amino acids substitutions, e.g., conservative substitutions of up to 10% or 20% of the residues, relative to a polypeptide encoded by one of SEQ ID NOs:1-6 or 8. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the isolated and/or purified nucleic acid molecule encodes a polypeptide with one or more, for instance, 2, 3 or 4, nonconservative amino acid substitutions, relative to a polypeptide encoded by one of SEQ ID NOs:1-6 or 33-38. For instance, a K55E NS and a S360Y PB2 substitution are nonconservative substitutions.

In another embodiment, the nucleic acid molecule having PB1, PB2, PA, NP, M, and NS, and optionally NA, sequences, or the complement thereof, hybridizes to one of SEQ ID NOs:1-6, 8, or 33 to 38, the complement thereof, under low stringency, moderate stringency or stringent conditions. For example, the following conditions may be employed: 7% sodium dodecyl sulfate (SDS), 0.5 M NaPO$_4$, 1 mM EDTA at 50° C. with washing in 2×SSC, 0.1% SDS at 50° C. (low stringency), more desirably in 7% sodium dodecyl sulfate (SDS), 0.5 M NaPO$_4$, 1 mM EDTA at 50° C. with washing in 1×SSC, 0.1% SDS at 50° C. (moderate stringency), more desirably still in 7% sodium dodecyl sulfate (SDS), 0.5 M NaPO$_4$, 1 mM EDTA at 50° C. with washing in 0.5×SSC, 0.1% SDS at 50° C. (stringent), preferably in 7% sodium dodecyl sulfate (SDS), 0.5 M NaPO$_4$, 1 mM EDTA at 50° C. with washing in 0.1×SSC, 0.1% SDS at 50° C. (more stringent), more preferably in 7% sodium dodecyl sulfate (SDS), 0.5 M NaPO$_4$, 1 mM EDTA at 50° C. with washing in 0.1×SSC, 0.1% SDS at 65° C. (very stringent). In one embodiment, the nucleic acid molecule encodes a polypeptide which is substantially the same as, e.g., having at least 50%, e.g., 60%, 70%, 80% or 90% or more contiguous nucleic acid sequence identity to, one of SEQ ID NOs:1-6, or 33 to 38, and preferably has substantially the same activity as a corresponding full-length polypeptide encoded by one of SEQ ID NOs:1-6, 8 or 33 to 28. Those nucleic acid molecules, or nucleic acid molecules from other N1 strains that grow well in eggs, may be employed with nucleic acid for any HA, e.g., H5.

Thus, nucleic acid molecule may be employed to express influenza proteins, to prepare chimeric genes, e.g., with other viral genes including other influenza virus genes, and/or to prepare recombinant virus. Thus, the invention also provides isolated polypeptides, recombinant virus, and host cells contacted with the nucleic acid molecules or recombinant virus of the invention.

The invention also provides a plurality of the following isolated and/or purified vectors: a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, a vector comprising a promoter operably linked to an influenza virus NS cDNA linked to a transcription termination sequence, wherein at least one vector comprises sequences corresponding to those encoding PB1, PB2, PA, NP, M, NS, and optionally NA, or a portion thereof, having substantially the same activity as a corresponding polypeptide encoded by one of SEQ ID NOs:1-6 or 8, e.g., a sequence encoding a polypeptide with at least 80% amino acid identity to a polypeptide encoded by one of SEQ ID NOs:1-6, 8 or 33 to 38. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

The invention includes the use of isolated and purified vectors or plasmids, which express or encode influenza virus proteins, or express or encode influenza vRNA, both native and recombinant vRNA. Preferably, the vectors comprise influenza cDNA, e.g., influenza A (e.g., any influenza A gene including any of the 15 HA or 9 NA subtypes), B or C DNA (see Chapters 45 and 46 of Fields *Virology* (Fields et al. (eds.), Lippincott-Raven Publ., Philadelphia, Pa. (1996), which are specifically incorporated by reference herein), although it is envisioned that the gene(s) of any organism may be employed in the vectors or methods of the invention. The cDNA may be in the sense or antisense orientation relative to the promoter. Thus, a vector of the invention may encode an influenza virus protein (sense) or vRNA (antisense). Any suitable promoter or transcription termination sequence may be employed to express a protein or peptide, e.g., a viral protein or peptide, a protein or peptide of a nonviral pathogen, or a therapeutic protein or peptide.

A composition of the invention may also comprise a gene or open reading frame of interest, e.g., a foreign gene encoding an immunogenic peptide or protein useful as a vaccine. Thus, another embodiment of the invention comprises a composition of the invention as described above in which one of the vectors is replaced with, or the composition further comprises, a vector comprising a promoter linked to 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof, linked to a transcription termination sequence. Preferably, the desired nucleic acid sequence such as a cDNA is in an antisense orientation. The introduction of such a composition to a host cell permissive for influenza virus replication results in recombinant virus comprising vRNA corresponding to sequences of the vector. The promoter in such a vector for vRNA production may be a RNA polymerase I promoter, a RNA polymerase II promoter, a RNA polymerase III promoter, a T7 promoter, and a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. In one embodiment, the vector comprising the desired nucleic acid sequence comprises a cDNA of interest. The cDNA of interest, whether in a vector for vRNA or protein production, may encode an immunogenic epitope, such as an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes.

A plurality of the vectors of the invention may be physically linked or each vector may be present on an individual plasmid or other, e.g., linear, nucleic acid delivery vehicle.

The promoter or transcription termination sequence in a vRNA or virus protein expression vector may be the same or different relative to the promoter or any other vector. Preferably, the vector or plasmid which expresses influenza vRNA comprises a promoter suitable for expression in at least one particular host cell, e.g., avian or mammalian host cells such as canine, feline, equine, bovine, ovine, or primate cells including human cells, or preferably, for expression in more than one host.

In one embodiment, one or more vectors for vRNA production comprise a promoter including, but not limited to, a RNA polymerase I promoter, e.g., a human RNA polymerase I promoter, a RNA polymerase II promoter, a RNA polymerase III promoter, a T7 promoter, or a T3 promoter. Preferred transcription termination sequences for the vRNA vectors include, but are not limited to, a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2 and preferably more, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

The invention also provides a method to prepare influenza virus. The method comprises contacting a cell with a plurality of the vectors of the invention, e.g., sequentially or simultaneously, for example, employing a composition of the invention, in an amount effective to yield infectious influenza virus. The invention also includes isolating virus from a cell contacted with the composition. Thus, the invention further provides isolated virus, as well as a host cell contacted with the composition or virus of the invention. In another embodiment, the invention includes contacting the cell with one or more vectors, either vRNA or protein production vectors, prior to other vectors, either vRNA or protein production vectors.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The invention also provides a method to immunize an individual against a pathogen, e.g., a bacteria, virus, or parasite, or a malignant tumor. The method comprises administering to the individual an amount of at least one isolated virus of the invention, optionally in combination with an adjuvant, effective to immunize the individual. The virus comprises vRNA comprising a polypeptide encoded by the pathogen or a tumor-specific polypeptide.

Also provided is a method to augment or increase the expression of an endogenous protein in a mammal having an indication or disease characterized by a decreased amount or a lack of the endogenous protein. The method comprises administering to the mammal an amount of an isolated virus of the invention effective to augment or increase the amount of the endogenous protein in the mammal. Preferably, the mammal is a human.

BRIEF DESCRIPTION OF THE DRAWINGS

FIGS. 1A and 1B. Titer of various influenza viruses.

FIG. 3. Growth of H5N1/PR8 reassortant viruses in chicken embryonated eggs. The titers of the reassortant viruses containing avirulent-form VN1203 HA and either homologous NA (VN1203) or heterologous NAs (VN1203fill, VN1203fill.N2, HK213, or PR8) with a PR8 background were compared by plaque titration with MDCK cells. The titer of wild-type (egg-adapted) PR8 also is included for comparison. The data are reported as mean titers and standard deviations for 3 eggs inoculated with each virus.

Figure 6:
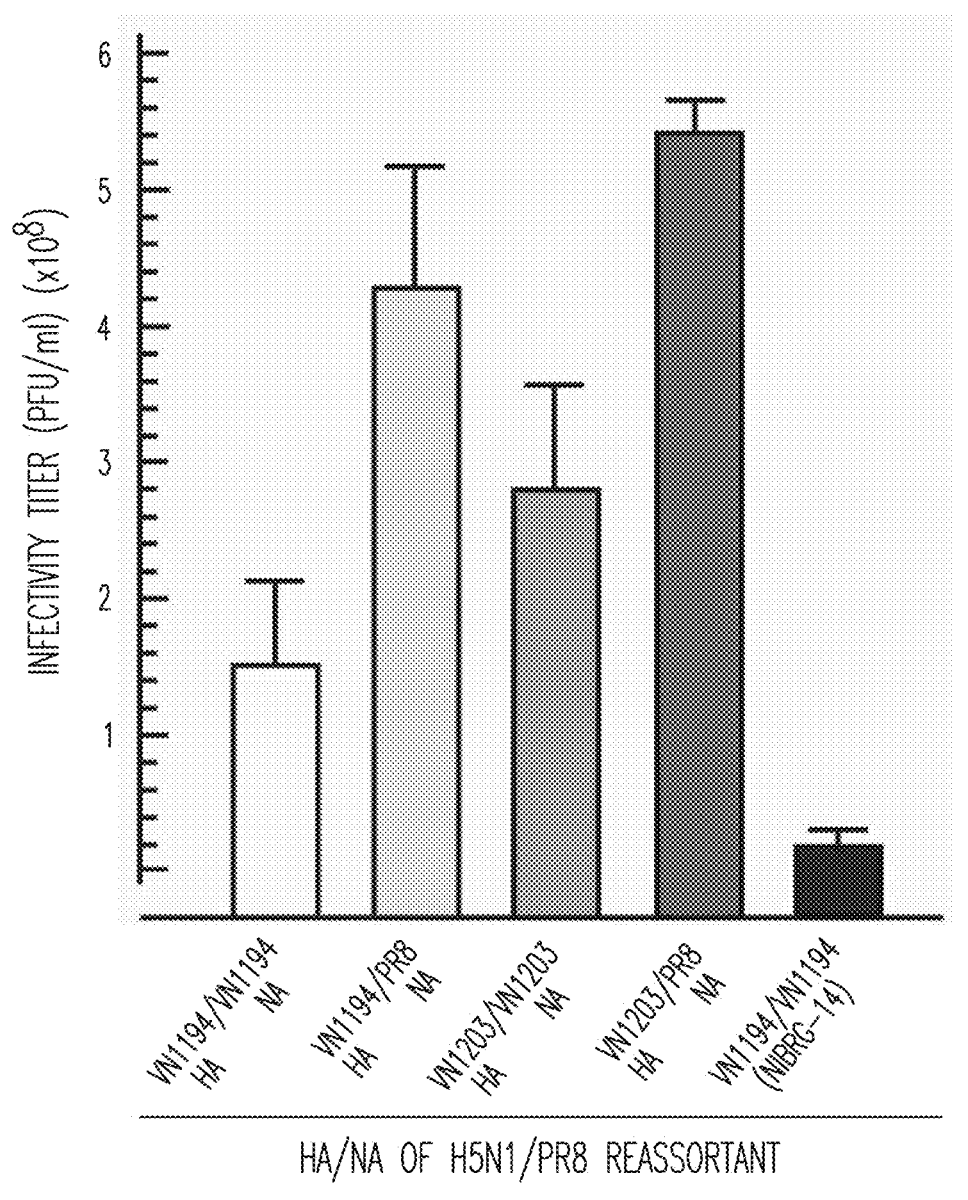

FIG. 6. Growth comparison of $H5N_1$/PR8 reassortant viruses in chicken embryonated eggs. Viral titers of the 6:2 and 7:1 reassortant viruses, including the WHO-recommended NIBRG-14 strain (a VN1194/PR8 6:2 reassortant virus) were compared by plaque titration with MDCK cells. Mean titers and standard deviations of 3 eggs inoculated with each virus are shown. Thus, replacing just the NA of H5N1 viruses with the NA of PR8 may improve titers in eggs.

FIG. 7. Growth of reassortant H5N1 viruses possessing PR8(UW) or PR8(Cambridge) internal genes in chicken embryonated eggs. Asterisks indicate a significant (p<0.05, Student t-test) reduction in infectivity compared to PR8 (UW)/1194.

FIG. 8. The effect of the M and NS genes on the growth of viruses in chicken embryonated eggs. The asterisk indicates a significant (p<0.05, Student t-test) increase in infectivity compared to PR8(UW)/1194.

FIG. 10. Identification of a gene segment responsible for the enhanced growth of PR8(UW)/1194 relative to NIBRG-14 in MDCK cells.

FIG. 11. Identification of the amino acid in PB2 responsible for the high growth rate of the vaccine seed virus in MDCK cells.

FIG. 12. Growth rates in MDCK cells of reassortants with different HA, NA, and NS genes. The asterisk indicates significantly better virus growth compared to that of PR8 (UW)/1194. Double asterisks indicate significantly better growth rates compared to viruses expressing PR8(UW) NS.

FIG. 13. Growth in MDCK cells of the H5N1 vaccine seed virus containing a heterologous NS segment.

FIG. 15A-15C. Nucleotide sequence for PR8(Cambridge) genes (SEQ ID NOs:33-38).

DETAILED DESCRIPTION OF THE INVENTION

Definitions

Figure 2:
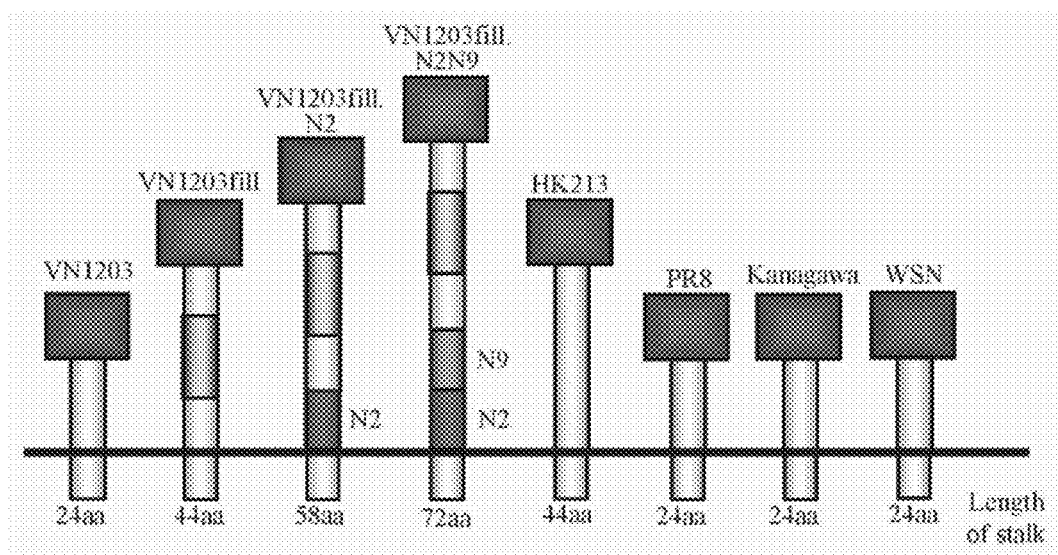
FIG. 2. Schematic diagram of the N1 NAs used to generate H5N1/PR8 reassortant viruses by reverse genetics. VN1203fill contains a 20 amino acid (aa) insertion derived from the N1 of the H5N1 precursor strain, GsGd96. VN1203fill.N2 contains, in addition to 20 as from GsGd96 NA, a 14-aa insertion from N2 NA, resulting in a 34-aa insertion into the stalk of VN1203 NA. VN1202fill.N2N9 contains, in addition to 20 aa from GsGd96 NA and 14 as from N2 NA, a 14-aa insertion from N9 NA, resulting in a 48-aa insertion into the stalk of VN1203. The predicted total length of the stalk region of each NA is given beneath each molecule.

As used herein, the terms "isolated and/or purified" refer to in vitro preparation, isolation and/or purification of a vector, plasmid or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or gene segment is from an influenza virus source that is different than a majority of the other influenza viral genes or gene segments in a reassortant influenza virus.

Influenza Virus Replication

Influenza A viruses possess a genome of eight single-stranded negative-sense viral RNAs (vRNAs) that encode a total of ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein. Similarly, influenza C virus does not have a M2 protein.

Cell Lines and Influenza Viruses that can be Used in the Present Invention

According to the present invention, any cell which supports efficient replication of influenza virus can be employed in the invention, including mutant cells which express reduced or decreased levels of one or more sialic acids which are receptors for influenza virus. Viruses obtained by the methods can be made into a reassortant virus.

Preferably, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity is preferably tested in cells that are at the same passage level as those used for vaccine production. The virus is preferably purified by a process that has been shown to give consistent results, before being inactivated or attenuated for vaccine production (see, e.g., World Health Organization, 1982).

It is preferred to establish a complete characterization of the cell lines to be used, so that appropriate tests for purity of the final product can be included. Data that can be used for the characterization of a cell to be used in the present invention includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. Preferably, the passage level, or population doubling, of the host cell used is as low as possible.

It is preferred that the virus produced in the cell is highly purified prior to vaccine or gene therapy formulation. Generally, the purification procedures will result in the extensive removal of cellular DNA, other cellular components, and adventitious agents. Procedures that extensively degrade or denature DNA can also be used. See, e.g., Mizrahi, 1990.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, then purified by a method such as that described by Grand and Skehel (1972).

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines.

Inactivated influenza virus vaccines of the invention are provided by inactivating replicated virus of the invention using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens are preferred.

Live Attenuated Virus Vaccines.

Live, attenuated influenza virus vaccines, can also be used for preventing or treating influenza virus infection, according to known method steps. Attenuation is preferably achieved in a single step by transfer of attenuated genes from an attenuated donor virus to a replicated isolate or reassorted virus according to known methods (see, e.g., Murphy, 1993). Since resistance to influenza A virus is mediated by the development of an immune response to the HA and NA glycoproteins, the genes coding for these surface antigens must come from the reassorted viruses or high growth clinical isolates. The attenuated genes are derived from the attenuated parent. In this approach, genes that confer attenuation preferably do not code for the HA and NA glycoproteins. Otherwise, these genes could not be transferred to reassortants bearing the surface antigens of the clinical virus isolate.

Many donor viruses have been evaluated for their ability to reproducibly attenuate influenza viruses. As a non-limiting example, the A/Ann Arbor(AA)/6/60 (H2N2) cold adapted (ca) donor virus can be used for attenuated vaccine production (see, e.g., Edwards, 1994; Murphy, 1993). Additionally, live, attenuated reassortant virus vaccines can be generated by mating the ca donor virus with a virulent replicated virus of the invention. Reassortant progeny are then selected at 25° C., (restrictive for replication of virulent virus), in the presence of an H2N2 antiserum, which inhibits replication of the viruses bearing the surface antigens of the attenuated A/AA/6/60 (H2N2) ca donor virus.

A large series of H1N1 and H3N2 reassortants have been evaluated in humans and found to be satisfactorily: (a) infectious, (b) attenuated for seronegative children and immunologically primed adults, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible adults and children.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene (Subbarao et al., 1993). Thus, new donor viruses can also be generated bearing attenuating mutations introduced by site-directed mutagenesis, and such new donor viruses can be used in the reduction of live attenuated reassortants H1N1 and H3N2 vaccine candidates in a manner analogous to that described above for the A/AA/6/60 ca donor virus. Similarly, other known and suitable attenuated donor strains can be reassorted with influenza virus of the invention to obtain attenuated vaccines suitable for use in the vaccination of mammals (Enami et al., 1990; Muster et al., 1991; Subbarao et al., 1993).

It is preferred that such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking infectivity to the degree that the vaccine causes minimal change of inducing a serious pathogenic condition in the vaccinated mammal.

The virus can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., 1988; Kilbourne, 1969; Aymard-Henry et al., 1985; Robertson et al., 1992.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987; *Avery's Drug Treatment,* 1987; Osol, 1980; Katzung, 1992. The composition of the invention is generally presented in the form of individual doses (unit doses).

Conventional vaccines generally contain about 0.1 to 200 µg, preferably 10 to 15 µg, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, H2N2 and H3N2 subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow et al., 1992; Avery's, 1987; Osol, 1980; and Katzung, 1992.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-50 strains or any range or value therein. Influenza A or B virus strains having a modern antigenic composition are preferred. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir. See, e.g., Katzung (1992), and the references cited therein on pages 798-800 and 680-681, respectively.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines, are provided before any symptom of a pathogen infection becomes manifest. The prophylactic administration of the composition serves to prevent or attenuate any subsequent infection. When provided prophylactically, the gene therapy compositions of the invention, are provided before any symptom of a disease becomes manifest. The prophylactic administration of the composition serves to prevent or attenuate one or more symptoms associated with the disease.

When provided therapeutically, an attenuated or inactivated viral vaccine is provided upon the detection of a symptom of actual infection. The therapeutic administration of the compound(s) serves to attenuate any actual infection. See, e.g., Berkow et al., 1992; Avery, 1987; and Katzung, 1992. When provided therapeutically, a gene therapy composition is provided upon the detection of a symptom or indication of the disease. The therapeutic administration of the compound(s) serves to attenuate a symptom or indication of that disease.

Thus, an attenuated or inactivated vaccine composition of the present invention may thus be provided either before the onset of infection (so as to prevent or attenuate an anticipated infection) or after the initiation of an actual infection. Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease. As used herein, a gene therapy composition is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described. For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow et al., 1992; Avery, 1987; and Katzung, 1992.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. See, e.g., Berkow et al., 1992; Avery's, 1987; and Katzung, 1992.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 µg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 µg or any range or value therein, or the amount recommended by the U.S. Public Heath Service (PHS), which is usually 15 µg, per component for older children □3 years of age, and 7.5 µg per component for older children <3 years of age. The quantity of NA can also be standardized, however, this glycoprotein can be labile during the processor purification and storage (Kendal et al., 1980). Each 0.5-ml dose of vaccine preferably contains approximately 1-50 billion virus particles, and preferably 10 billion particles.

The invention will be further described by the following nonlimiting examples.

Example 1

To develop a reverse genetics system for influenza A/Puerto Rico/8/34, viral RNA was extracted from the allantoic fluid of A/Puerto Rico/8/34 (H1N1), Madison high grower variant (PR8HG), using RNeasy Mini kit (Qiagen) according to the manufacturer's protocol. cDNA was synthesized using MMLV-RTase (Promega) and Uni12 primer. The cDNAs were amplified overnight by PCR using the following:
Primer Sets

```
PB1:
Ba PB1-1 and PB1-1735R (front fragment) and
PB1-903 and Ba-PB1-2341R (rear fragment)
Ba-PB 1-1
                                  (SEQ ID NO: 9)
CACACACGGTCTCCGGGAGCGAAAGCAGGCA 173PB1-1735R
                                  (SEQ ID NO: 28)
GGGTTTGTATTTGTGTGTCACC 233PB1-903
                                  (SEQ ID NO: 10)
CCAGGACACTGAAATTTCTTTCAC Ba-PB1-2341R
                                  (SEQ ID NO: 11)
CACACAGGTCTCCTATTAGTAGAAACAAGGCATTT PB2:
Ba PB2-1 and B2 1260R (front fragment) and
WSN PB2 seq-2 and Ba-PB2-2341R (rear
fragment)
Ba-PB2-1
                                  (SEQ ID NO: 12)
CACACAGGTCTCCGGGAGCGAAAGCAGGTC B2 1260R
                                  (SEQ ID NO: 13)
CACACACGTCTCCATCATACAATCCTCTTG WSN PB2 seq-2
                                  (SEQ ID NO: 14)
CTCCTCTGATGGTGGCATAC Ba-PB2-2341R
                                  (SEQ ID NO: 15)
CACACAGGTCTCCTATTAGTAGAAACAAGGTCGTTT PA:
Bm-PA-1
                                  (SEQ ID NO: 16)
CACACACGTCTCCGGGAGCGAAAGCAGGTAC Bm-PA-2233R
                                  (SEQ ID NO: 17)
CACACACGTCTCCTATTAGTAGAAACAAGGTACTT HA:
Bm-HA-1:
                                  (SEQ ID NO: 18)
CACACACGTCTCCGGGAGCAAAAGCAGGGG Bm-NS-890R:
                                  (SEQ ID NO: 19)
CACACACGTCTCCTATTAGTAGAAACAAGGGTGTTTT NP:
Bm-NP-1
                                  (SEQ ID NO: 20)
CACACACGTCTCCGGGAGCAAAAGCAGGGTA Bm-NP-1565R
                                  (SEQ ID NO: 21)
CACACACGTCTCCTATTAGTAGAAACAAGGGTATTTTT NA:
Ba-NA-1:
                                  (SEQ ID NO: 22)
CACACAGGTCTCCGGGAGCAAAAGCAGGAGT Ba-NA-1413R:
                                  (SEQ ID NO: 23)
CACACAGGTCTGGTATTAGTAGAAACAAGGAGTTTTTT
```

M:
Bm-M-1
(SEQ ID NO: 24)
CACACACGTCTCCGGGAGCAAAAGCAGGTAG

Bm-M-1027R
(SEQ ID NO: 25)
CACACACGTCTCCTATTAGTAGAAACAAGGTAGTTTTT

NS:
Bm-NS-1
(SEQ ID NO: 26)
CACACACGTCTCCGGGAGCAAAAGCAGGGTG

Bm-NS-890R
(SEQ ID NO: 27)
CACACACGTCTCCTATTAGTAGAAACAAGGGTGTTTT
DNA polymerase: pfu Native DNA
polymerase (Stratagene)

The PCR products were separated by gel electrophoresis and extracted from the agarose gel using a gel extraction kit (Qiagen). The extracted genes were ligated into pT7Blue blunt vector (Novagen) using a Takara ligation kit ver. II (Takara). After 5 hours, the ligated genes were transformed into JM109 (PB2, M, and NS genes) or DH5alpha (PA, PB1, and NP). Six colonies for each gene were cultured in TB for 8 hours. The plasmids were extracted from the bacteria culture, and four clones per gene were sequenced.

The PA, NP, M, and NS genes in pT7Blue were excised by Bsm BI enzyme (New England Biolabs). The PB1 gene was excised by Bsa I (New England Biolabs). The excised genes were ligated overnight with pPolIR vector which contains the human RNA polymerase I promoter and the mouse RNA polymerase I terminator which had been digested with Bsm BI. The front fragment of the PB2 gene in pT7Blue was excised by Bsr GI (New England Biolabs) and Bam HI (Roche), and the rear fragment was excised by Bsr GI (New England Biolabs) and Spe I (Roche). The excised fragments were mixed and digested by Bsa I. After 6 hours, the digested genes were purified using a PCR purification kit (Qiagen) and ligated overnight between the Bsm BI sites of the pPolIR vector.

The ligated PB1, PA, NP, M, and NS-pPolIR genes were used to transform JM109 (M and NS genes) or DH5alpha (PB1, PA and NP genes) overnight. The colonies of transformed bacteria were cultured in LB overnight. The ligated PB2-pPoIR was used to transform JM109 overnight.

The plasmids were extracted from the bacterial cultures and gene inserts were confirmed by enzyme digestion. The colonies of bacteria transformed by PB2-PolIR were cultured in LB for 8 hours. The plasmids were then extracted and the gene insertion was confirmed by enzyme digestion. All pPolI constructs were sequenced to ensure that they did not contain unwanted mutations.

The pPolIR constructs for PR8HG were transfected into 293T human embryonic kidney cells with A/WSN/33 (WSN)-HA and NA, A/Hong Kong/483/97(HK)-HAavir and NA, or A/Kawasaki/01(Kawasaki)-HA and NA PolI constructs and four protein-expression constructs for the polymerase proteins and NP of A/WSN/33. The supernatants from transfected 293T cells were serially diluted (undiluted to $10^{-7}$) and infected into the allantoic cavities of 9-day-old embryonated chicken eggs. The allantoic fluids of the infected eggs were harvested and their virus titers tested by HA assay (Table 1).

TABLE 1

| Virus possessing PR8 genes together with the following HA and NA genes | HA titer (HAU/ml) of allantoic fluid from eggs inoculated with 293T supernatants diluted at: undiluted | $10^{-1}$ | $10^{-2}$ | $10^{-3}$ | $10^{-4}$ | $10^{-5}$ | $10^{-6}$ | $10^{-7}$ |
|---|---|---|---|---|---|---|---|---|
| WSN-HA NA | <1 | <1 | 200 | <1 | <1 | <1 | <1 | <1 |
| HK-HAavir NA | 100 | <1 | <1 | <1 | <1 | <1 | <1 | <1 |
| Kawasaki-HA NA | <1 | <1 | <1 | <1 | <1 | <1 | <1 | <1 |

HA-positive samples (virus with WSN-HA NA at $10^{-2}$ and virus with HK-HAavir NA at undiluted) were diluted serially from $10^{-2}$ to $10^{-8}$ and 100 ul of each dilution was infected into embryonated chicken eggs. The allantoic fluids of the infected eggs were harvested and their virus titers tested by HA assay (Table 2). The 50% egg infectious dose ($EID_{50}$) of A/Puerto Rico/8/34 (H1N1) prepared from plasmids was $10^{10.33}$/ml, and the HA titer was 1:3200.

A recombinant virus having the HA and NA genes from A/Hong Kong/213/2003 (H5N1) and the remainder of the type A influenza virus genes from PR8HG was prepared. The titer of the recombinant virus was $10^{10.67}$ $EID_{50}$/ml, and the HA titer was 1:1600

TABLE 2

| Virus possessing PR8 genes together with the following HA and NA genes | HA titer (HAU/ml) in each dilition 10-2 | 10-3 | 10-4 | 10-5 | 10-6 | 10-7 | 10-8 |
|---|---|---|---|---|---|---|---|
| WSN-HA NA | 160 | 40 | 40 | 320 | 40 | 640 | <1 |
| HK-HAavir NA | 400 | 800 | 400 | 400 | 400 | 800 | <1 |

Sequences of PR8 Genes:

```
PA
                                        (SEQ ID NO: 1)
AGCGAAAGCA GGTACTGATC CAAAATGGAA GATTTTGTGC

GACAATGCTT CAATCCGATG ATTGTCGAGC TTGCGGAAAA

AACAATGAAA GAGTATGGGG AGGACCTGAA AATCGAAACA

AACAAATTTG CAGCAATATG CACTCACTTG GAAGTATGCT

TCATGTATTC AGATTTTCAC TTCATCAATG AGCAAGGCGA

GTCAATAATC GTAGAACTTG GTGATCCAAA TGCACTTTTG

AAGCACAGAT TTGAAATAAT CGAGGGAAGA GATCGCACAA

TGGCCTGGAC AGTAGTAAAC AGTATTTGCA ACACTACAGG

GGCTGAGAAA CCAAAGTTTC TACCAGATTT GTATGATTAC

AAGGAGAATA GATTCATCGA AATTGGAGTA ACAAGGAGAG

AAGTTCACAT ATACTATCTG GAAAAGGCCA ATAAAATTAA

ATCTGAGAAA ACACACATCC ACATTTTCTC GTTCACTGGG

GAAGAAATGG CCACAAAGGC AGACTACACT CTCGATGAAG

AAAGCAGGGC TAGGATCAAA ACCAGACTAT TCACCATAAG
```

-continued

```
ACAAGAAATG GCCAGCAGAG GCCTCTGGGA TTCCTTTCGT
CAGTCCGAGA GAGGAGAAGA GACAATTGAA GAAAGGTTTG
AAATCACAGG AACAATGCGC AAGCTTGCCG ACCAAAGTCT
CCCGCCGAAC TTCTCCAGCC TTGAAAATTT TAGAGCCTAT
GTGGATGGAT TCGAACCGAA CGGCTACATT GAGGGCAAGC
TGTCTCAAAT GTCCAAAGAA GTAAATGCTA GAATTGAACC
TTTTTTGAAA CAACACCAC GACCACTTAG ACTTCCGAAT
GGGCCTCCCT GTTCTCAGCG GTCCAAATTC CTGCTGATGG
ATGCCTTAAA ATTAAGCATT GAGGACCCAA GTCATGAAGG
AGAGGGAATA CCGCTATATG ATGCAATCAA ATGCATGAGA
ACATTCTTTG GATGGAAGGA ACCCAATGTT GTTAAACCAC
ACGAAAAGGG AATAAATCCA AATTATCTTC TGTCATGAAA
GCAAGTACTG GCAGAACTGC AGGACATTGA GAATGAGGAG
AAAATTCCAA AGACTAAAAA TATGAAGAAA CAAGTCAGC
TAAAGTGGGC ACTTGGTGAG AACATGGCAC CAGAAAAGGT
AGACTTTGAC GACTGTAAAG ATGTAGGTGA TTTGAAGCAA
TATGATAGTG ATGAACCAGA ATTGAGGTCG CTTGCAAGTT
GGATTCAGAA TGAGTTTAAC AAGGCATGCG AACTGACAGA
TTCAAGCTGG ATAGAGCTCG ATGAGATTGG AGAAGATGTG
GCTCCAATTG AACACATTGC AAGCATGAGA AGGAATTATT
TCACATCAGA GGTGTCTCAC TGCAGAGCCA CAGAATACAT
AATGAAGGGA GTGTACATCA ATACTGCCTT GCTTAATGCA
TCTTGTGCAG CAATGGATGA TTTCCAATTA ATTCCAATGA
TAAGCAAGTG TAGAACTAAG GAGGGAAGGC GAAAGACCAA
CTTGTATGGT TTCATCAAA AGGAAGATC CCACTTAAGG
AATGACACCG ACGTGGTAAA CTTTGTGAGC ATGGAGTTTT
CTCTCACTGA CCCAAGACTT GAACCACATA AATGGGAGAA
GTACTGTGTT CTTGAGATAG GAGATATGCT TATAAGAAGT
GCCATAGGCC AGGTTTCAAG GCCCATGTTC TTGTATGTGA
GAACAAATGG AACCTCAAAA ATTAAATGA AATGGGGAAT
GGAGATGAGG CGTTGCCTCC TCCAGTCACT TCAACAAATT
GAGAGTATGA TTGAAGCTGA GTCCTCTGTC AAAGAGAAAG
ACATGACCAA AGAGTTCTTT GAGAACAAAT CAGAAACATG
GCCCATTGGA GAGTCCCCCA AAGGAGTGGA GGAAAGTTCC
ATTGGGAAGG TCTGCAGGAC TTTATTAGCA AAGTCGGTAT
TCAACAGCTT GTATGCATCT CCACAACTAG AAGGATTTTC
AGCTGAATCA AGAAAACTGC TTCTTATCGT TCAGGCTCTT
AGGGACAACC TGGAACCTGG GACCTTTGAT CTTGGGGGGC
TATATGAAGC AATTGAGGAG TGCCTGATTA ATGATCCCTG
GGTTTTGCTT AATGCTTCTT GGTTCAACTC CTTCCTTACA
CATGCATTGA GTTAGTTGTG GCAGTGCTAC TATTTGCTAT
CCATACTGTC CAAAAAGTA CCTTGTTTCT ACT

PB1
                              (SEQ ID NO: 2)
AGCGAAAGCA GGCAAACCAT TTGAATGGAT GTCAATCCGA
CCTTACTTTT CTTAAAGTGC CAGCACAAA ATGCTATAAG
CACAACTTTC CCTTATACTG GAGACCCTCC TTACAGCCAT
GGGACAGGAA CAGGATACAC CATGGATACT GTCAACAGGA
CACATCAGTA CTCAGAAAAG GGAAGATGGA CAACAAACAC
CGAAACTGGA GCACCGCAAC TCAACCCGAT TGATGGGCCA
CTGCCAGAAG ACAATGAACC AAGTGGTTAT GCCCAAACAG
ATTGTGTATT GGAGGCGATG GCTTTCCTTG AGGAATCCCA
TCCTGGTATT TTTGAAAACT CGTGTATTGA ACGATGGAG
GTTGTTCAGC AAACACGAGT AGACAAGCTG ACACAAGGCC
GACAGACCTA TGACTGGACT CTAAATAGAA ACCAACCTGC
TGCAACAGCA TTGGCCAACA CAATAGAAGT GTTCAGATCA
AATGGCCTCA CGGCCAATGA GTCTGGAAGG CTCATAGACT
TCCTTAAGGA TGTAATGGAG TCAATGAACA AAGAAGAAAT
GGGGATCACA ACTCATTTTC AGAGAAAGAG ACGGGTGAGA
GACAATATGA CTAAGAAAAT GATAACACAG AGAACAATGG
GTAAAAGAA GCAGAGATTG AACAAAAGGA GTTATCTAAT
TAGAGCATTG ACCCTGAACA CAATGACCAA AGATGCTGAG
AGAGGGAAGC TAAAACGGAG AGCAATTGCA ACCCCAGGGA
TGCAAATAAG GGGGTTTGTA TACTTTGTTG AGACACTGGC
AAGGAGTATA TGTGAGAAAC TTGAACAATC AGGGTTGCCA
GTTGGAGGCA ATGAGAAGAA AGCAAAGTTG GCAAATGTTG
TAAGGAAGAT GATGACCAAT TCTCAGGACA CCGAACTTTC
TTTCACCATC ACTGGAGATA ACACCAAATG AACGAAAAT
CAGAATCCTC GGATGTTTTT GGCCATGATC ACATATATGA
CCAGAAATCA GCCCGAATGG TTCAGAAATG TTCTAAGTAT
TGCTCCAATA ATGTTCTCAA ACAAAATGGC GAGACTGGGA
AAAGGGTATA TGTTTGAGAG CAAGAGTATG AAACTTAGAA
CTCAAATACC TGCAGAAATG CTAGCAAGCA TCGATTTGAA
ATATTTCAAT GATTCAACAA GAAAGAAGAT TGAAAAAATC
CGACCGCTCT TAATAGAGGG GACTGCATCA TTGAGCCCTG
GAATGATGAT GGGCATGTTC AATATGTTAA GCACTGTATT
AGGCGTCTCC ATCCTGAATC TTGGACAAAA GAGATACACC
AAGACTACTT ACTGGTGGGA TGGTCTTCAA TCCTCTGACG
ATTTTGCTCT GATTGTGAAT GCACCCAATC ATGAAGGGAT
TCAAGCCGGA GTCGACAGGT TTTATCGAAC CTGTAAGCTA
CTTGGAATCA ATATGAGCAA GAAAAAGTCT TACATAAACA
GAACAGGTAC ATTTGAATTC ACAAGTTTTT TCTATCGTTA
```

-continued

TGGGTTTGTT GCCAATTTCA GCATGGAGCT TCCCAGTTTT
GGGGTGTCTG GGATCAACGA GTCAGCGGAC ATGAGTATTG
GAGTTACTGT CATCAAAAAC AATATGATAA ACAATGATCT
TGGTCCAGCA ACAGCTCAAA TGGCCCTTCA GTTGTTCATC
AAAGATTACA GGTACACGTA CCGATGCCAT ATAGGTGACA
CACAAATACA AACCCGAAGA TCATTTGAAA TAAAGAAACT
GTGGGAGCAA ACCCGTTCCA AAGCTGGACT GCTGGTCTCC
GACGGAGGCC CAAATTTATA CAACATTAGA AATCTCCACA
TTCCTGAAGT CTGCCTAAAA TGGGAATTGA TGGATGAGGA
TTACCAGGGG CGTTTATGCA ACCCACTGAA CCCATTTGTC
AGCCATAAAG AAATTGAATC AATGAACAAT GCAGTGATGA
TGCCAGCACA TGGTCCAGCC AAAAACATGG AGTATGATGC
TGTTGCAACA ACACACTCCT GGATCCCCAA AGAAATCGA
TCCATCTTGA ATACAAGTCA AGAGGAGTA CTTGAGGATG
AACAAATGTA CCAAAGGTGC TGCAATTTAT TTGAAAAATT
CTTCCCCAGC AGTTCATACA GAAGACCAGT CGGGATATCC
AGTATGGTGG AGGCTATGGT TTCCAGAGCC CGAATTGATG
CACGGATTGA TTTCGAATCT GGAAGGATAA AGAAAGAAGA
GTTCACTGAG ATCATGAAGA TCTGTTCCAC CATTGAAGAG
CTCAGACGGC AAAAATAGTG AATTTAGCTT GTCCTTCATG
AAAAAATGCC TTGTTTCTAC T

PB2
(SEQ ID NO: 3)
AGCGAAAGCA GGTCAATTAT ATTCAATATG GAAAGAATAA
AAGAACTACG AAATCTAATG TCGCAGTCTC GCACCCGCGA
GATACTCACA AAAACCACCG TGGACCATAT GGCCATAATC
AAGAAGTACA CATCAGGAAG ACAGGAGAAG AACCCAGCAC
TTAGGATGAA ATGGATGATG GCAATGAAAT ATCCAATTAC
AGCAGACAAG AGGATAACGG AAATGATTCC TGAGAGAAAT
GAGCAAGGAC AAACTTTATG GAGTAAAATG AATGATGCCG
GATCAGACCG AGTGATGGTA TCACCTCTGG CTGTGACATG
GTGGAATAGG AATGGACCAA TAACAAATAC AGTTCATTAT
CCAAAAATCT ACAAAACTTA TTTTGAAAGA GTCGAAAGGC
TAAAGCATGG AACCTTTGGC CCTGTCCATT TTAGAAACCA
AGTCAAAATA CGTCGGAGAG TTGACATAAA TCCTGGTCAT
GCAGATCTCA GTGCCAAGGA GGCACAGGT GTAATCATGG
AAGTTGTTTT CCCTAACGAA GTGGGAGCCA GGATACTAAC
ATCGGAATCG CAACTAACGA TAACCAAAGA GAAGAAAGAA
GAACTCCAGG ATTGCAAAAT TTCTCCTTTG ATGGTTGCAT
ACATGTTGGA GAGAACTGG TGTCGCAAAA CGAGATTCCT
CCCAGTGGCT GGTGGAACAA GCAGTGTGTA CATTGAAGTG
TTGCATTTGA CTCAAGGAAC ATGCTGGGAA CAGATGTATA

-continued

CTCCAGGAGG GGAAGTGAGG AATGATGATG TTGATCAAAG
CTTGATTATT GCTGCTAGGA ACATAGTGAG AAGAGCTGCA
GTATCAGCAG ATCCACTAGC ATCTTTATTG GAGATGTGCC
ACAGCACACA GATTGGTGGA ATTAGGATGG TAGACATCCT
TAGGCAGAAC CCAACAGAAG AGCAAGCCGT GGATATATGC
AAGGCTGCAA TGGGACTGAG AATTAGCTCA TCCTTCAGTT
TTGGTGGATT CACATTTAAG AGAACAAGCG GATCATCAGT
CAAGAGAGAG GAAGAGGTGC TTACGGGCAA TCTTCAAACA
TTGAAGATAA GAGTGCATGA GGGATATGAA GAGTTCACAA
TGGTTGGGAG AAGAGCAACA GCCATACTCA GAAAAGCAAC
CAGGAGATTG ATTCAGCTGA TAGTGAGTGG GAGAGACGAA
CAGTCGATTG CCGAAGCAAT AATTGTGGCC ATGGTATTTT
CACAAGAGGA TTGTATGATA AAAGCAGTCA GAGGTGATCT
GAATTTCGTC AATAGGGCGA ATCAACGATT GAATCCTATG
CATCAACTTT TAAGACATTT TCAGAAGGAT GCGAAAGTGC
TTTTTCAAAA TTGGGGAGTT GAACCTATCG ACAATGTGAT
GGGAATGATT GGGATATTGC CCGACATGAC TCCAAGCATC
GAGATGTCAA TGAGAGGAGT GAGAATCAGC AAAATGGGTG
TAGATGAGTA CTCCAGCACG GAGAGGGTAG TGGTGAGCAT
TGACCGTTTT TTGAGAATCC GGGACCAACG AGGAAATGTA
CTACTGTCTC CCGAGGAGGT CAGTGAAACA CAGGGAACAG
AGAAACTGAC AATAACTTAC TCATCGTCAA TGATGTGGGA
GATTAATGGT CCTGAATCAG TGTTGGTCAA TACCTATCAA
TGGATCATCA GAAACTGGGA AACTGTTAAA ATTCAGTGGT
CCCAGAACCC TACAATGCTA TACAATAAAA TGGAATTTGA
ACCATTTCAG TCTTTAGTAC CTAAGGCCAT TAGAGGCCAA
TACAGTGGGT TTGTAAGAAC TCTGTTCCAA CAAATGAGGG
ATGTGCTTGG GACATTTGAT ACCGCACAGA TAATAAAACT
TCTTCCCTTC GCAGCCGCTC CACCAAAGCA AAGTAGAATG
CAGTTCTCCT CATTTACTGT GAATGTGAGG GGATCAGGAA
TGAGAATACT TGTAAGGGGC AATTCTCCTG TATTCAACTA
TAACAAGGCC ACGAAGAGAC TCACAGTTCT CGGAAAGGAT
GCTGGCACTT TAACTGAAGA CCCAGATGAA GGCACAGCTG
GAGTGGAGTC CGCTGTTCTG AGGGGATTCC TCATTCTGGG
CAAAGAAGAC AAGAGATATG GGCCAGCACT AAGCATCAAT
GAACTGAGCA ACCTTGCGAA AGGAGAGAAG GCTAATGTGC
TAATTGGGCA AGGAGACGTG GTGTTGGTAA TGAAACGGAA
ACGGGACTCT AGCATACTTA CTGACAGCCA GACAGCGACC
AAAAGAATTC GGATGGCCTA CAATTAGTGT CGAATAGTTT
AAAAACGACC TTGTTTCTAC T

NP (SEQ ID NO: 4)
AGCAAAAGCA GGGTAGATAA TCACTCACTG AGTGACATCA

AAATCATGGC GTCTCAAGGC ACCAAACGAT CTTACGAACA

GATGGAGACT GATGGAGAAC GCCAGAATGC CACTGAAATC

AGAGCATCCG TCGGAAAAAT GATTGGTGGA ATTGGACGAT

TCTACATCCA AATGTGCACC GAACTCAAAC TCAGTGATTA

TGAGGGACGG TTGATCCAAA ACAGCTTAAC AATAGAGAGA

ATGGTGCTCT CTGCTTTTGA CGAAAGGAGA AATAAATACC

TTGAAGAACA TCCCAGTGCG GGGAAAGATC CTAAGAAAAC

TGGAGGACCT ATATACAGGA GAGTAAACGG AAAGTGGATG

AGAGAACTCA TCCTTTATGA CAAAGAAGAA ATAAGGCGAA

TCTGGCGCCA AGCTAATAAT GGTGACGATG CAACGGCTGG

TCTGACTCAC ATGATGATCT GGCATTCCAA TTTGAATGAT

GCAACTTATC AGAGGACAAG AGCTCTTGTT CGCACCGGAA

TGGATCCCAG GATGTGCTCT CTGATGCAAG GTTCAACTCT

CCCTAGGAGG TCTGGAGCCG CAGGTGCTGC AGTCAAAGGA

GTTGGAACAA TGGTGATGGA ATTGGTCAGA ATGATCAAAC

GTGGGATCAA TGATCGGAAC TTCTGGAGGG GTGAGAATGG

ACGAAAAACA AGAATTGCTT ATGAAAGAAT GTGCAACATT

CTCAAAGGGA AATTTCAAAC TGCTGCACAA AAAGCAATGA

TGGATCAAGT GAGAGAGAGC CGGAACCCAG GAATGCTGA

GTTCGAAGAT CTCACTTTTC TAGCACGGTC TGCACTCATA

TTGAGAGGGT CGGTTGCTCA CAAGTCCTGC CTGCCTGCCT

GTGTGTATGG ACCTGCCGTA GCCAGTGGGT ACGACTTTGA

AAGGGAGGGA TACTCTCTAG TCGGAATAGA CCCTTTCAGA

CTGCTTCAAA ACAGCCAAGT GTACAGCCTA ATCAGACCAA

ATGAGAATCC AGCACACAAG AGTCAACTGG TGTGGATGGC

ATGCCATTCT GCCGCATTTG AAGATCAAG AGTATTAAGC

TTCATCAAAG GGACGAAGGT GCTCCCAAGA GGGAAGCTTT

CCACTAGAGG AGTTCAAATT GCTTCCAATG AAAATATGGA

GACTATGGAA TCAAGTACAC TTGAACTGAG AAGCAGGTAC

TGGGCCATAA GGACCAGAAG TGGAGGAAAC ACCAATCAAC

AGAGGGCATC TGCGGGCCAA ATCAGCATAC AACCTACGTT

CTCAGTACAG AGAAATCTCC CTTTTGACAG AACAACCATT

ATGGCAGCAT TCAATGGGAA TACAGAGGGG AGAACATCTG

ACATGAGGAC CGAAATCATA AGGATGATGG AAAGTGCAAG

ACCAGAAGAT GTGTCTTTCC AGGGGCGGGA AGTCTTCGAG

CTCTCGGACG AAAAGGCAGC GAGCCCGATC GTGCCTTCCT

TTGACATGAG TAATGAAGGA TCTTATTTCT TCGGAGACAA

TGCAGAGGAG TACGACAATT AAAGAAAAAT ACCCTTGTTT

CTACT

M (SEQ ID NO: 5)
AGCAAAAGCA GGTAGATATT GAAAGATGAG TCTTCTAACC

GAGGTCGAAA CGTACGTACT CTCTATCATC CCGTCAGGCC

CCCTCAAAGC CGAGATCGCA CAGAGACTTG AAGATGTCTT

TGCAGGGAAG AACACCGATC TTGAGGTTCT CATGGAATGG

CTAAAGACAA GACCAATCCT GTCACCTCTG ACTAAGGGGA

TTTTAGGATT TGTGTTCACG CTCACCGTGC CCAGTGAGCG

AGGACTGCAG CGTAGACGCT TTGTCCAAAA TGCCCTTAAT

GGGAACGGGG ATCCAAATAA CATGGACAAA GCAGTTAAAC

TGTATAGGAA GCTCAAGAGG GAGATAACAT TCCATGGGGC

CAAAGAAATC TCACTCAGTT ATTCTGCTGG TGCACTTGCC

AGTTGTATGG GCCTCATATA CAACAGGATG GGGGCTGTGA

CCACTGAAGT GGCATTTGGC CTGGTATGTG CAACCTGTGA

ACAGATTGCT GACTCCCAGC ATCGGTCTCA TAGGCAAATG

GTGACAACAA CCAATCCACT AATCAGACAT GAGAACAGAA

TGGTTTTAGC CAGCACTACA GCTAAGGCTA TGGAGCAAAT

GGCTGGATCG AGTGAGCAAG CAGCAGAGGC CATGGAGGTT

GCTAGTCAGG CTAGACAAAT GGTGCAAGCG ATGAGAACCA

TTGGGACTCA TCCTAGCTCC AGTGCTGGTC TGAAAAATGA

TCTTCTTGAA ATTTGCAGG CCTATCAGAA CGAATGGGG

GTGCAGATGC AACGGTTCAA GTGATCCTCT CACTATTGCC

GCAAATATCA TTGGGATCTT GCACTTGACA TTGTGGATTC

TTGATCGTCT TTTTTTCAAA TGCATTTACC GTCGCTTTAA

ATACGGACTG AAAGGAGGGC CTTCTACGGA AGGAGTGCCA

AAGTCTATGA GGGAAGAATA TCGAAAGGAA CAGCAGAGTG

CTGTGGATGC TGACGATGGT CATTTTGTCA GCATAGAGCT

GGAGTAAAAA ACTACCTTGT TTCTACT

NS (SEQ ID NO: 6)
AGCAAAAGCA GGGTGACAAA AACATAATGG ATCCAAACAC

TGTGTCAAGC TTTCAGGTAG ATTGCTTTCT TTGGCATGTC

CGCAAACGAG TTGCAGACCA AGAACTAGGC GATGCCCCAT

TCCTTGATCG GCTTCGCCGA GATCAGAAAT CCCTAAGAGG

AAGGGGCAGT ACTCTCGGTC TGGACATCAA GACAGCCACA

CGTGCTGGAA AGCAGATAGT GGAGCGGATT CTGAAAGAAG

AATCCGATGA GGCACTTAAA ATGACCATGG CCTCTGTACC

TGCGTCGCGT TACCTAACTG ACATGACTCT TGAGGAAATG

TCAAGGGACT GGTCCATGCT CATACCCAAG CAGAAAGTGG

CAGGCCCTCT TTGTATCAGA ATGGACCAGG CGATCATGGA

TAAGAACATC ATACTGAAAG CGAACTTCAG TGTGATTTTT

GACCGGCTGG AGACTCTAAT ATTGCTAAGG GCTTTCACCG

HA (SEQ ID NO: 7)

AAGAGGGAGC AATTGTTGGC GAAATTTCAC CATTGCCTTC

TCTTCCAGGA CATACTGCTG AGGATGTCAA AAATGCAGTT

GGAGTCCTCA TCGGAGGACT TGAATGGAAT GATAACACAG

TTCGAGTCTC TGAAACTCTA CAGAGATTCG CTTGGAGAAG

CAGTAATGAG AATGGGAGAC CTCCACTCAC TCCAAACAG

AAACGAGAAA TGGCGGGAAC AATTAGGTCA GAAGTTTGAA

GAAATAAGAT GGTTGATTGA AGAAGTGAGA CACAAACTGA

AGATAACAGA GAATAGTTTT GAGCAAATAA CATTTATGCA

AGCCTTACAT CTATTGCTTG AAGTGGAGCA AGAGATAAGA

ACTTTCTCGT TTCAGCTTAT TTAGTACTAA AAACACCCT

TGTTTCTACT

NA (SEQ ID NO: 8)

AGCAAAAGCA GGGGAAAATA AAAACAACC AAAATGAAGGCAAA

CCTACTGGTC CTGTTATGTG CACTTGCAGC TGCAGATGCAGAC

ACAATATGTA TAGGCTACCA TGCGAACAAT TCAACCGACACTG

TTGACACAGT ACTCGAGAAG AATGTGACAG TGACACACTCTGT

TAACCTGCTC GAAGACAGCC ACAACGGAAA ACTATGTAGATTA

AAAGGAATAG CCCCACTACA ATTGGGGAAA TGTAACATCGCCG

GATGGCTCTT GGGAAACCCA GAATGCGACC CACTGCTTCCAGT

GAGATCATGG TCCTACATTG TAGAAACACC AAACTCTGAGAAT

GGAATATGTT ATCCAGGAGA TTTCATCGAC TATGAGGAGCTGA

GGGAGCAATT GAGCTCAGTG TCATCATTCG AAAGATTCGAAAT

ATTTCCCAAA GAAAGCTCAT GGCCCAACCA CAACACAAACGGA

GTAACGGCAG CATGCTCCCA TGAGGGGAAA AGCAGTTTTTACA

GAAATTTGCT ATGGCTGACG GAGAAGGAGG GCTCATACCCAAA

GCTGAAAATT CTTATGTGAA CAAAAAAGGG AAAGAAGTCCTT

GTACTGTGGG GTATTCATCA CCCGCCTAAC AGTAAGGAACAAC

AGAATCTCTA TCAGAATGAA AATGCTTATG TCTCTGTAGTGAC

TTCAAATTAT AACAGGAGAT TTACCCCGGA AATAGCAGAAAGA

CCCAAAGTAA GAGATCAAGC TGGGAGGATG AACTATTACTGGA

CCTTGCTAAA ACCCGGAGAC ACAATAATAT TTGAGGCAAATGG

AAATCTAATA GCACCAATGT ATGCTTTCGC ACTGAGTAGAGGC

TTTGGGTCCG GCATCATCAC CTCAAACGCA TCAATGCATGAGT

GTAACACGAA GTGTCAAACA CCCCTGGGAG CTATAAACAGCAG

TCTCCCTTAC CAGAATATAC ACCCAGTCAC AATAGGAGAGTGC

CCAAAATACG TCAGGAGTGC CAAATTGAGG ATGGTTACAGGAC

TAAGGAACAT TCCGTCCATT CAATCCAGAG GTCTATTTGGAGC

CATTGCCGGT TTTATTGAAG GGGGATGGAC TGGAATGATAGAT

GGATGGTATG GTTATCATCA TCAGAATGAA CAGGGATCAGGCT

ATGCAGCGGA TCAAAAAAGC ACACAAAATG CCATTAACGGGAT

TACAAACAAG GTGAACACTG TTATCGAGAA AATGAACATTCAA

TTCACAGCTG TGGGTAAAGA ATTCAACAAA TTAGAAAAAGGA

TGGAAAATTT AAATAAAAAG TTGATGATGG ATTTCTGGACAT

TTGGACATAT AATGCAGAAT TGTTAGTTCT ACTGGAAAATGAA

AGGACTCTGG ATTTCCATGA CTCAAATGTG AAGAATCTGTATG

AGAAAGTAAA AAGCCAATTA AAGAATAATG CCAAAGAAATCGG

AAATGGATGT TTTGAGTTCT ACCACAAGTG TGACAATGAATGC

ATGGAAAGTG TAAGAAATGG GACTTATGAT TATCCCAAATATT

CAGAAGAGTC AAAGTTGAAC AGGGAAAAGG TAGATGGAGTGAA

ATTGGAATCA ATGGGGATCT ATCAGATTCT GGCGATCTACTCA

ACTGTCGCCA GTTCACTGGT GCTTTTGGTC TCCCTGGGGGCAA

TCAGTTTCTG GATGTGTTCT AATGGATCTT TGCAGTGCAGAAT

ATGCATCTGA GATTAGAATT TCAGAGATATG AGGAAAAACACC

CTTGTTTCTACT

NA (SEQ ID NO: 8)

AGCAAAAGCA GGGGTTTAAA ATGAATCCAA ATCAGAAAATAAT

AACCATTGGA TCAATCTGTC TGGTAGTCGG ACTAATTAGCCTA

ATATTGCAAA TAGGGAATAT AATCTCAATA TGGATTAGCCATT

CAATTCAAAC TGGAAGTCAA AACCATACTG GAATATGCAACCA

AAACATCATT ACCTATAAAA ATAGCACCTG GGTAAAGGACACA

ACTTCAGTGA TATTAACCGG CAATTCATCT CTTTGTCCCATCC

GTGGGTGGGC TATATACAGC AAAGACAATA GCATAAGAATTGG

TTCCAAAGGA GACGTTTTTG TCATAAGAGA GCCCTTTATTCA

TGTTCTCACT TGGAATGCAG GACCTTTTTT CTGACCCAAGGTG

CCTTACTGAA TGACAAGCAT TCAAGTGGGA CTGTTAAGGACAG

AAGCCCTTAT AGGGCCTTAA TGAGCTGCCC TGTCGGTGAAGCT

CCGTCCCCGT ACAATTCAAG ATTTGAATCG GTTGCTTGGTCAG

CAAGTGCATG TCATGATGGC ATGGGCTGGC TAACAATCGGAAT

TTCAGGTCCA GATAATGGAG CAGTGGCTGT ATTAAAATACAAC

GGCATAATAA CTGAAACCAT AAAAAGTTGG AGGAAGAAATAT

TGAGGACACA AGAGTCTGAA TGTGCCTGTG TAAATGGTTCATG

TTTTACTATA ATGACTGATG GCCCGAGTGA TGGGCTGGCCTCG

TACAAAATTT TCAAGATCGA AAAGGGGAAG GTTACTAAATCAA

TAGAGTTGAA TGCACCTAAT TCTCACTATG AGGAATGTTCCTG

TTACCCTGAT ACCGGCAAAG TGATGTGTGT GCAGAGACAAT

TGGCATGGTT CGAACCGGCC ATGGGTGTCT TTCGATCAAAACC

TGGATTATCA AATAGGATAC ATCTGCAGTG GGGTTTTCGGTGA

CAACCCGCGT CCCGAAGATG AACAGGCAGC TGTGGTCCAGTG

TATGTTGATG GAGCAAACGG AGTAAAGGGA TTTTCATATAGGT

ATGGTAATGG TGTTTGGATA GGAAGGACCA AAAGTCACAGTTC

CAGACATGGG TTTGAGATGA TTTGGGATCC TAATGGATGGACA

-continued
```
GAGACTGATAGTAAGTTCTCTGTGAGGCAAGATGTTGTGGCAA

TGACTGATTGGTCAGGGTATAGCGGAAGTTTCGTTCAACATCC

TGAGCTGACAGGGCTAGACTGTATGAGGCCGTGCTTCTGGGTT

GAATTAATCAGGGGACGACCTAAAGAAAAAACAATCTGGACTA

GTGCGAGCAGCATTTCTTTTTGTGGCGTGAATAGTGATACTGT

AGATTGGTCTTGGCCAGACGGTGCTGAGTTGCCATTCAGCATT

GACAAGTAGTCTGTTCAAAAAACTCCTTGTTTCTACT
```

Example 2

Influenza virus A/Hong Kong/213/2003 (H5N1, HK213) replicates systemically in chickens, causing lethal infection. Furthermore, this virus is lethal to chicken embryos. Thus, although its surface proteins are highly related to the currently circulating pathogenic avian influenza viruses, HK213 cannot be used as a vaccine strain as attempts to grow it in embryonated chicken eggs result in the production of poor-quality allantoic fluid. Additionally, the use of this highly virulent virus in the production of vaccines is unsafe for vaccine workers. To test the feasibility of using A/PR/8/34 as a master vaccine strain, the cleavage site of the hemagglutinin (HA) gene of HK213 (containing multiple basic amino acids) was mutated from a virulent to an avirulent phenotype (from RERRRKKR (SEQ ID NO:29) to -TETR (SEQ ID NO:30)). A virus containing the mutated HA gene produced non-lethal, localized infection in chickens. Additionally, the mutated virus was non-lethal to chicken embryos. Thus, growth of the mutated virus in embronated eggs yielded high-quality allantoic fluid, and in this attenuated form, the virus is safe for vaccine producers.

A recombinant virus containing the neuraminidase (NA) and mutated HA genes from HK213, and all the remaining genes from high-titer A/PR/8/34 (H1N1, HG-PR8) virus (Example 1), which grows 10 times better than other A/PR/8/34 PR8 strains in eggs ($10^{10}$ $EID_{50}$/ml; HA titer: 1:8,000), was generated in embryonated chicken eggs. This recombinant virus, which expresses surface proteins related to the currently circulating pathogenic avian influenza virus, grew to high titers in embryonated chicken eggs (FIGS. 1A and 1B). Thus, replacement of the HA and NA genes of HG-PR8 with those of a currently circulating strain of influenza virus resulted in a vaccine strain that can be safely produced, and demonstrates the use of PR8-HG as a master vaccine strain.

Example 3

In Hong Kong in 1997, a highly pathogenic H5N1 avian influenza virus was transmitted directly from birds to humans, causing 18 confirmed infections and 6 deaths (Subbarao et al., 1998; Claas et al., 1998). In 2004-6, the geographic distribution of H5N1 viruses expanded in Asia, spreading to several adjacent European countries and to Africa. Altogether, 96 people infected with the virus have died in Vietnam, Thailand, Cambodia, Indonesia, China, Turkey, and Iraq (Li et al., 2004; WHO). These fatal outbreaks and the continued threat of a pandemic have led to the development of H5N1 virus vaccines for use in humans. However, because pathogenic H5N1 viruses grow poorly in embryonated chicken eggs and pose serious biosafety concerns for vaccine producers, reverse genetics has been used to generate vaccine candidates (Subbarao et al., 2003; Webby et al., 2004; Stephanson et al., 2004; Wood & Robertson, 2004).

Recombinant (6:2 reassortant) viruses that possess modified avirulent-type hemagglutinin (HA) and neuraminidase (NA) genes, both derived from a pathogenic H5N1 strain, with all remaining genes from a donor virus that grows well in eggs, are among the candidates to be produced by this method. The World Health Organization (WHO) recommends A/Puerto Rico/8/34 (H1N1; PR8) as a donor virus, because of its safety in humans and vigorous growth in eggs (Wood & Robertson, 2004; Webby & Webster, 2003). Recently, it was shown that such recombinant viruses grow less well in eggs than does the wild-type PR8 strain, even though they possess the same PR8 "internal" genes (i.e., those other than the HA and NA) (Horimoto et al., 2006).

Since vigorous growth in eggs is an essential property of vaccine seed viruses used in the production of inactivated vaccines, as described below, H5N1 vaccine candidates were generated that grow as well as the PR8 donor strain in eggs. First, the molecular basis for the high growth of PR8 in eggs was determined by defining the genes responsible for this property using reassortment analysis between PR8 and a WSN strain that grows poorly in eggs. It was found that HA-NA balance and PB1 function are important growth determinants. With this knowledge, a series of H5N1 viruses was produced with altered HA-NA combinations, with the PR8 background, to assess their growth in eggs against more conventional 6:2 reassortants, including the WHO-recommended NIBRG-14 virus.

Methods

Cells and Viruses 293T human embryonic kidney cells were maintained in Dulbecco's modified Eagle's minimal essential medium (DMEM) with 10% fetal calf serum and antibiotics. Madin-Darby canine kidney (MDCK) cells were grown in MEM with 5% newborn calf serum and antibiotics. African green monkey Vero WCB cells, which had been established after biosafety tests for use in human vaccine production (Sugawara et al., 2002), were maintained in serum-free VP-SFM medium (GIBCO-BRL) with antibiotics. Cells were maintained at 37° C. in 5% $CO_2$. The A/Vietnam/1194/2004 and A/Vietnam/1203/2004 (H5N; VN1194 and VN1203) strains, isolated from humans, were propagated in 10-day-old embryonated chicken eggs for 2 days at 37° C., after which time the allantoic fluids containing virus were harvested and used for further experiments. All experiments with these viruses were carried out in a Biosafety Level 3 containment laboratory. The WHO-recommended vaccine seed virus, NIBRG-14 (VN1194/PR8 6:2 reassortant virus), was kindly gifted by Drs. John Wood and Jim Robertson at the National Institute for Biological Standards and Control, UK.

Construction of Plasmids and Reverse Genetics

To generate reassortants of influenza A viruses, a plasmid-based reverse genetics (Neumann et al., 1999) was used. Viral RNA from VN1194 or VN1203 was extracted from allantoic fluid by using a commercial kit (ISOGEN LS, Nippon Gene) and was converted to cDNA by using reverse transcriptase (SuperScript III; GIBCO-BRL) and primers containing the consensus sequences of the 3' ends of the RNA segments for the H5 viruses. The full-length cDNAs were then PCR-amplified with ProofStart polymerase (QIAGEN) and H5 subtype-specific primer pairs, and cloned into a plasmid under control of the human polymerase I promoter and the mouse RNA polymerase I terminator (PolI plasmids), generating a PolI-VN1194/HA or a PolI-VN1203/HA construct containing the VN1194 or VN1203 HA gene, respectively. By inverse PCR using back-to-back primer pairs, followed by ligation, the HA cleavage site sequence of the wild-type VN1194 or VN1203 (RERRRKKR; SEQ ID NO:29) virus was altered to create the avirulent-type sequence (RETR; SEQ ID NO:31) as described in Horimoto et al. (2006), the disclosure of which is incorporated by reference herein. A PolI-VN1203NA containing the VN1203 NA gene was constructed by the RT-PCR procedure (described above) with N1-specific primers. A series of pPolI NA mutant plasmids were prepared by inverse PCR. Using the PolI-VN1203NA as a template, pPolI-NAfill was constructed, which encodes a mutant NA containing a 20-amino acid (aa) (CNQSIITYENNTWVNQTYVN; SEQ ID NO:32) insertion derived from A/goose/Guangdong/1/96 (H5N1; GsGd96) NA into the NA stalk between 48-Pro and 49-Ile. pPolI-NAfill.N2 and -NAfill.N2N9, in which N2 (12 aa) or N2+N9 (12+12 aa) sequences derived from the stalk region of each NA subtype were inserted into the NA stalk between 42-Asn and 43-Gin, were constructed as described in Castrucci et al. (1993). All of these constructs were sequenced to ensure the absence of unwanted mutations.

A previously produced series of PolI constructs, derived from A/WSN/33 (H5N1; WSN) and PR8 strains was used, for reverse genetics (Horimoto et al., 2006; Neumann et al., 1999). Additionally, PolI constructs containing NA genes derived from A/Hong Kong/213/03 (H5N1; HK213), and A/Kanagawa/173/2001 (H1N1; Kanagawa) were used in this study (Horimoto et al., 2006; Kobasa et al., 2004; Peiris et al., 2004).

Plasmids expressing WSN or PR8 NP, PA, PB1, or PB2 under control of the chicken β-actin promoter were used for all reverse genetics experiments (Horimoto et al., 2006; Neumann et al., 1999). Briefly, PolI plasmids and protein expression plasmids were mixed with a transfection reagent, Trans-IT 293T (Panvera), incubated at room temperature for 15 min, and then added to 293T cells. Transfected cells were incubated in Opti-MEM I (GIBCO-BRL) for 48 hours. For reverse genetics in Vero WCB cells, an electroporator (Amaxa) was used to transfect the plasmid mixtures according to the manufacturer's instructions. Sixteen hours after transfection, freshly prepared Vero WCB cells were added onto the transfected cells and TPCK-trypsin (1 µg/ml) was added to the culture 6 hours later. Transfected cells were incubated in serum-free VP-SFM for a total of 4 days. Supernatants containing infectious viruses were harvested, biologically cloned by limiting dilution in embryonated eggs, and used in further experiments.

Properties of Viral Replication in Eggs

Virus was inoculated into the allantoic cavity of 10-day-old embryonated chicken eggs, and incubated at 37° C. for 48 hours. Virus in the allantoic fluids was then titrated by HA assay using either 0.5%/chicken erythrocytes or 0.8% guinea pig erythrocytes or in eggs to determine the median egg infectious dose ($EID_{50}$)/ml of virus. For some viruses, plaque titration was conducted with MDCK cells and TPCK-trypsin (1 µg/ml). The growth kinetics of some viruses was assessed in eggs after inoculating $10^4$ $EID_{50}$ of virus.

Virus Elution Assay from Chicken Erythrocytes

Fifty µl of twofold dilutions of virus containing the HA titers of 1:1024 were incubated with 50 Id of 0.5% chicken erythrocytes in a microtiter plate at 4° C. for 1 hour. The plate was then stored at 37° C., and the reduction of HA titers was recorded periodically. Phosphate-buffered saline with 6.8 mM $CaCl_2$ was used as a diluent.

Results

Molecular Basis for the High Growth Property of PR8 in Chicken Eggs

Although PR8 is recommended by WHO for use as a donor virus to generate reverse genetics-based H5 influenza vaccine, the molecular basis of its high growth property is not fully understood. The M gene was said to be responsible for the vigorous growth of PR8 in eggs (Subbarao et al., 2003), but this claim is apparently not found in the published original data (Kilbourne et al., 1969). Thus, a reassortment analysis was conducted using a WSN strain that grows poorly in eggs. Table 3 shows the compatibility between the HAs and NAs of PR8 versus the WSN strain in terms of viral growth in embryonated chicken eggs. All reassortant test viruses grew better than the wild-type WSN, but less well than the egg-adapted PR8, demonstrating that both surface glycoproteins and internal proteins are responsible for the high growth property of PR8.

TABLE 3

Compatibility between the HAs and NAs of PR8 versus WSN strains, assessed by viral growth in chicken embryonated eggs

| Gene constellation of reassortant | | | HA titer[b] | |
|---|---|---|---|---|
| HA | NA | 6 others[a] | Chicken RBC | Guinea pig RBC |
| WSN | WSN | WSN | 16/8 | 32/8 |
| PR8 | WSN | WSN | 64/32 | 64/32 |
| WSN | PR8 | WSN | 16/16 | 32/16 |
| PR8 | PR8 | WSN | 128/128 | 128/128 |
| WSN | WSN | PR8 | 64/64 | 64/64 |
| PR8 | WSN | PR8 | 64/128 | 64/128 |
| WSN | PR8 | PR8 | 512/512 | 512/512 |
| PR8 | PR8 | PR8 | 2048/2048 | 2048/2048 |

[a]Genes encoding the internal proteins PB1, PB2, PA, NP, M, and NS.
[b]Growth of each reassortant virus in chicken eggs, assessed in HA assays with 0.5% chicken RBC and 0.8% guinea pig RBC. HA titers from two independent experiments are shown.

Since the growth of a reassortant virus containing both of the PR8 glycoproteins and all six internal proteins derived from WSN was drastically reduced in eggs, as compared with that of PR8 (Tables 3 and 4), a series of reassortant viruses was produced to define the internal proteins responsible for this property. A single-gene reassortant virus containing the WSN PB1 and all remaining genes from PR8 grew poorly, at a level similar to that of a reassortant containing all of the WSN genes encoding internal proteins, whereas a reassortant containing the PR8 PB1 and WSN genes encoding all remaining internal proteins replicated to a high titer (Table 4). Thus, the PR8 PB1 likely possesses the optimal polymerase activity for viral genome replication in eggs, in contrast to a previous report implicating the M segment in this role (Subbarao et al., 2003).

TABLE 4

Compatibility among genes encoding internal proteins of PR8 and WSN viruses, assessed by viral growth in chicken embryonated eggs Gene constellation of reassortant [a]

| HA | NA | PB2 | PB1 | PA | NP | M | NS | HA titer [b] |
|---|---|---|---|---|---|---|---|---|
| PR8 | PR8 | PR8 | PR8 | PR8 | PR8 | PR8 | PR8 | 2048/2048/1024 |
| PR8 | PR8 | PR8 | PR8 | PR8 | PR8 | PR8 | WSN | 1024/1024/1024 |
| PR8 | PR8 | PR8 | PR8 | PR8 | PR8 | WSN | PR8 | 2048/1024/1024 |
| PR8 | PR8 | PR8 | PR8 | PR8 | PR8 | WSN | WSN | 1024/1024/512 |
| PR8 | PR8 | PR8 | PR8 | PR8 | WSN | PR8 | PR8 | 1024/1024/512 |
| PR8 | PR8 | PR8 | PR8 | WSN | PR8 | PR8 | PR8 | 1024/512/256 |
| PR8 | PR8 | PR8 | WSN | PR8 | PR8 | PR8 | PR8 | 128/64/64 |
| PR8 | PR8 | WSN | PR8 | PR8 | PR8 | PR8 | PR8 | 1024/1024/1024 |
| PR8 | PR8 | WSN | WSN | WSN | WSN | PR8 | PR8 | 64/64/32 |
| PR8 | PR8 | WSN | WSN | WSN | WSN | WSN | WSN | 128/64/64 |
| PR8 | PR8 | WSN | PR8 | WSN | WSN | WSN | WSN | 1024/512/512 |

[a] Both the HA and NA genes were derived from PR8 in all reassortant viruses, while some of the genes encoding internal proteins were from the WSN strain.
[b] Growth rate of each reassortant virus in chicken eggs was assessed with HA assays in 0.5% chicken RBC. HA titers, obtained in three independent experiments, are shown.

Generation of H5N1 Vaccine Seed Candidates with Enhanced Growth Ability in Chicken Eggs In an earlier study, the growth of WSN in eggs was shown to be enhanced by lengthening the NA stalk to increase NA function: the longer the stalk, the better the replication of the virus (Castrucci et al., 1993). This finding prompted the production of a series of H5N1 viruses comprising mutated or heterologous N1s with the PR8 background and compare their growth in eggs. The A/Vietnam/1203/2004 (H5N1; VN1203) NA contains a 20-amino acid (20-aa) deletion in its stalk region (hence, 24 aa in the stalk). Therefore, a mutant NA, VN1203fill, was constructed containing a 44-aa stalk like the H5N1 precursor virus A/goose/Guangdong/1/96 (H5N1) (Xu et al., 1999), as well as other NA mutants, VN1202fill.N2 and VN1203fill.N2N9 that contained longer stalks, 58- and 72-aa, respectively (FIG. 2). The heterologous N1 from A/Hong Kong/213/03 (H5N1; HK213) containing 44-aa in the stalk was also examined. The NAs from H1N1 strains such as PR8, A/Kanagawa/173/2001 (H1N1; Kanagawa), and WSN, all of which possess 24-aa in the stalk, were also tested. Using these NA constructs, a total of eight reassortant viruses was generated, seven 6:2 and one 7:1 with the modified avirulent-type VN1203 HA and PR8 background (Table 5). Another series of reassortant viruses was constructed with the modified avirulent-type A/Vietnam/1194/2004 (H5N1; VN1194) HA. By comparison with constructs containing the parental VN1203 NA, only the 7:1 reassortant virus and a 6:2 reassortant containing a combination of the modified VN1194 HA and VN1203fill NA, showed enhanced growth in eggs.

Figure 3:
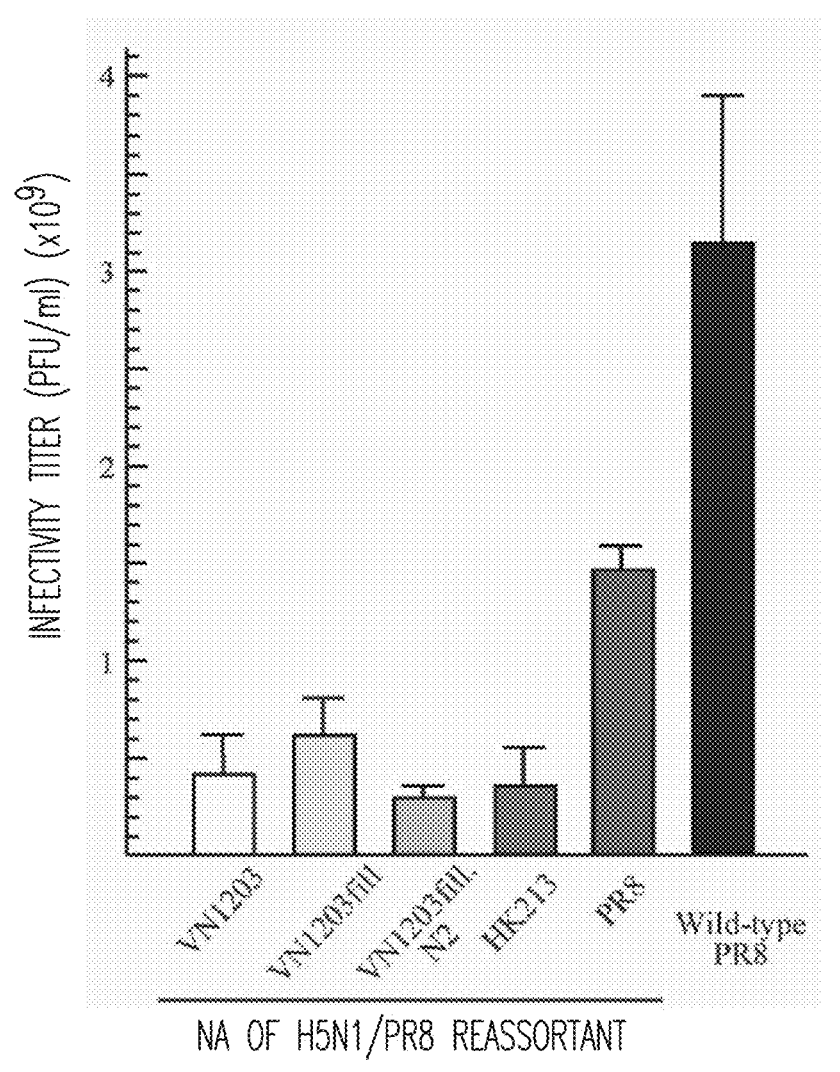
Figure 4:
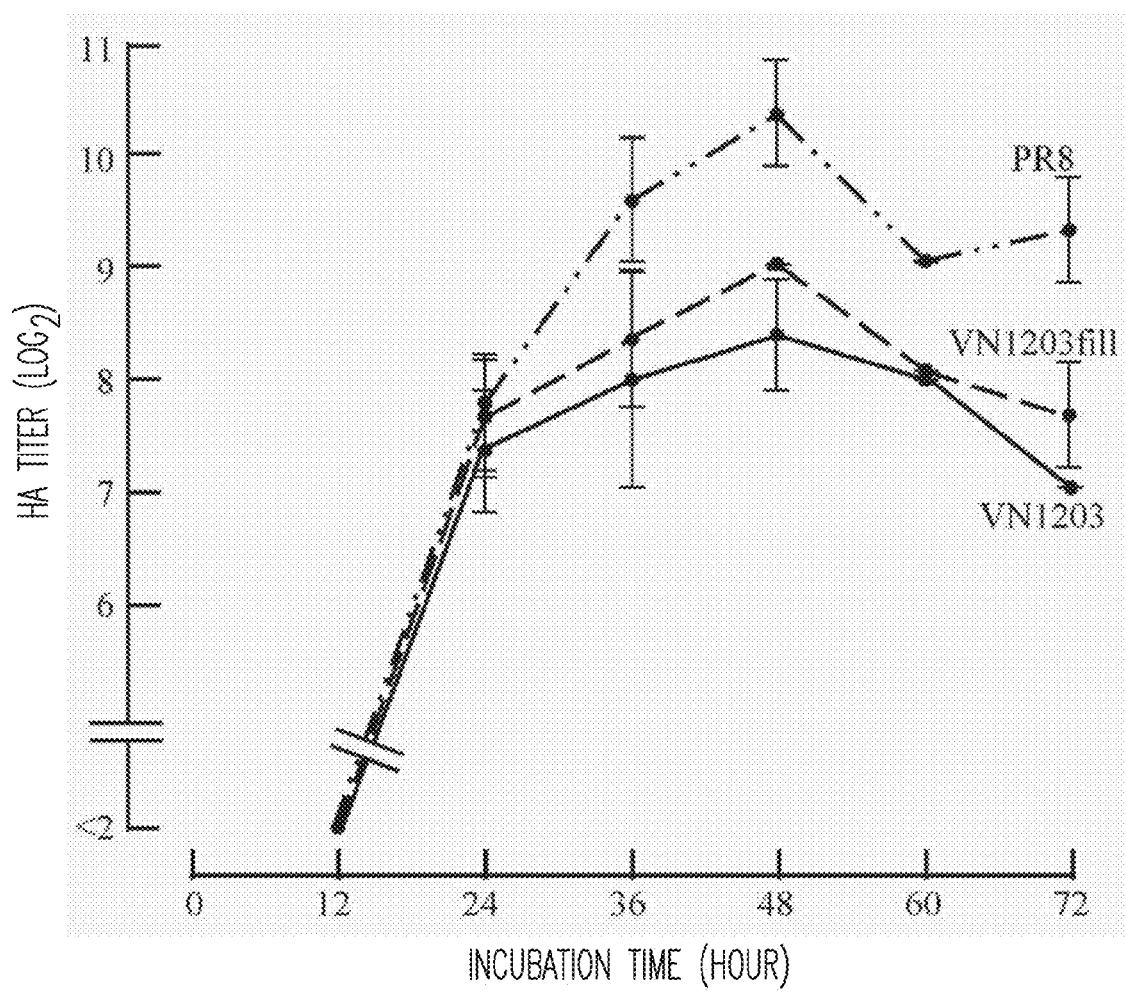
FIG. 4. Growth kinetics of H5N1 reassortant viruses in chicken embryonated eggs. We inoculated eggs with the same amounts ($10^4$ $EID_{50}$) of viruses containing PR8 NA (PR8), VN1203 NA (VN1203), or VN1203fill NA (VN1203fill). Mean HA titers and standard deviations for 3 eggs inoculated with each virus were determined at the indicated time points.

Further testing of selected reassortant viruses by a plaque assay of the stock viruses demonstrated a greater than 3-fold higher titer (p=0.003, Student t-test) for the reassortant virus containing PR8 NA compared with the virus containing parental VN1203 NA, although it did not grow as well as egg-adapted PR8 (FIG. 3). Assessment of the growth kinetics of reassortant viruses with the PR8, VN1203fill or VN1203 NA in eggs revealed a superior growth rate for the virus with PR8 NA (7:1 reassortant) (FIG. 4).

Figure 5:
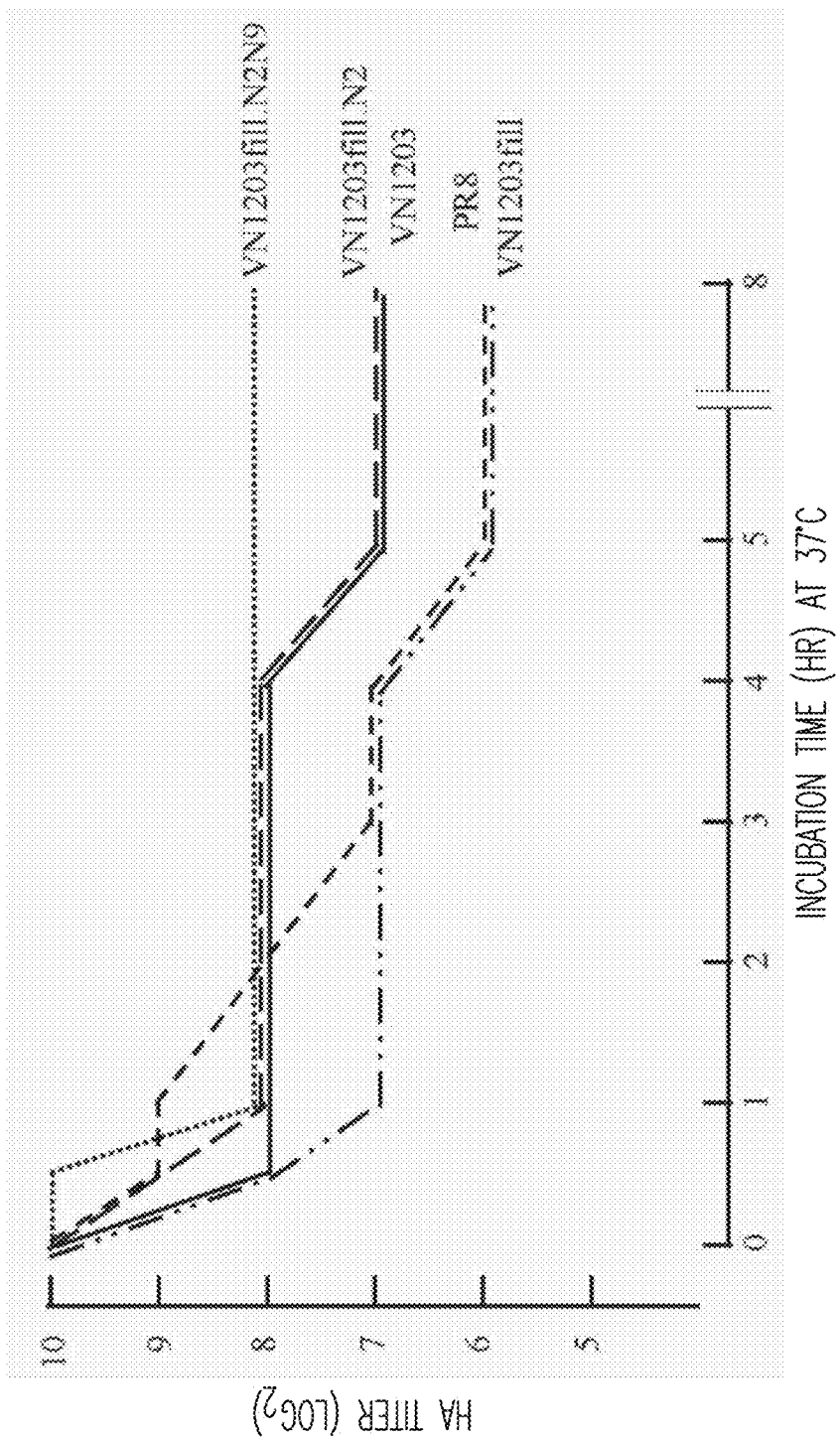
FIG. 5. Virus elution from chicken erythrocytes. Twofold dilutions of each virus (HA titers of 1:1024) containing VN1203 NA with a different stalk length, or PR8 NA, were incubated with chicken erythrocytes in a microtiter plate at 4° C. for 1 hour. The plate was then stored at 37° C. and reductions in the HA titer were recorded for 8 hours.

To determine the molecular basis of the high growth property observed in the 7:1 reassortant virus, the NA function of reassortant viruses was tested by an assay evaluating virus elution from chicken erythrocytes (FIG. 5). Reassortant viruses containing PR8 or VN1203fill NA were eluted from erythrocytes more rapidly than those with the parental VN1203 NA, indicating greater NA activity for PR8 or VN1203fill.NA. These results support the idea that high NA function enhances viral growth in eggs (Castrucci et al., 1993).

Growth Comparison of H5N1 Vaccine Seed Candidates Produced in this Study with the WHO-Recommended Vaccine Seed Virus, NIBRG-14, in Eggs To validate the potential of candidate seed viruses in the production of H5N1 vaccines, their infectivity titers were compared with that of the WHO-provided NIBRG-14 virus under the same experimental conditions. The 7:1 reassortant viruses containing either VN1194 or VN1203-derived HAs and all the other genes from our PR8 strain showed significantly higher titers (p<0.05, Student t-test) than the NIBRG-14 virus in eggs, as assessed by $EID_{50}$ (Table 6) and plaque

TABLE 5

Viral titers of H5N1/PR8 reassortant viruses in chicken embryonated eggs [a]

HA titer/Infectivity titer ($log_2/log_{10}EID_{50}/ml$)

| HA [b] | Experiment [c] | NA derived from [d] | | | | |
|---|---|---|---|---|---|---|
| | | VN1203 | VN1203fill | VN1203fill.N2 | VN1203fill.N2N9 | HK213 |
| VN1203 | 1 | 9.2 ± 0.4/8.9 ± 0.3 [f] | 9.6 ± 0.5/8.8 ± 0.6 | 9.2 ± 0.5/8.9 ± 0.4 | 9.0 ± 0.0/8.8 ± 0.5 | 9.6 ± 0.5/8.8 ± 0.1 |
| | 2 | 9.0 ± 1.0/9.4 ± 0 2 | 9.0 ± 0.0/9.7 ± 0.2 | 8.3 ± 0.6/8.6 ± 0.2 | 8.0 ± 0.0/ND | 8.7 ± 0.6/8.5 ± 0.3 |
| VN1194 | 1 | 8.7 ± 0.6/8.7 ± 0.2 | 9.3 ± 0.6/9.3 ± 0.2 | 9.3 ± 0.6/9.2 ± 0.2 | 9.0 ± 0.0/8.6 ± 0.2 | ND/ND |

| | HA [b] | Experiment [c] | NA derived from [d] | | | Wild-type |
|---|---|---|---|---|---|---|
| | | | PR8 | Kanagawa | WSN | PR8 [e] |
| | VN1203 | 1 | 9.6 ± 0.5/9.5 ± 0.4 | 9.8 ± 0.4/9.4 ± 0.2 | <1.0/ND | 10.7 ± 0.6/10.3 ± 0.4 |
| | | 2 | 9.7 ± 0.6/10.1 ± 0.2 | ND/ND | ND/ND | 11.0 ± 0.0/10.3 ± 0.4 |
| | VN1194 | 1 | 9.3 ± 0.6/9.5 ± 0.3 | 9.0 ± 0.0/8.8 ± 0.9 | <1.0/5.2 ± 0.2 | 10.7 ± 0.6/10.1 ± 0.2 |

[a] Eggs (10-day-old) were inoculated with virus ($10^4$ $EID_{50}$), and incubated for 48 hours at 37° C.; viral titers in allantoic fluids were determined.

[b] Two H5 HA genes (VN1203 and VN1194) were used to generate reassortant viruses with a PR8 background. The HA cleavage sites of both VN1203 and VN1194 were modified to that of the avirulent-type H5 HA.

[c] Two independent experiments, each using 3 to 5 eggs, were performed for VN1203 constructs, while a single experiment was done for VN1194.

[d] A total of eight NA genes were used to generate reassortant viruses; three insertion mutant NAs (VN1203fill, VN1203fill.N2, and VN1203fill.N2N9) were prepared to assess the influence of NA stalk length on virus growth in eggs by comparison to parental VN1203 NA; the other NAs were derived from an H5N1 human isolate (HK213) or H1N1 viruses (PR8, Kanagawa, and WSN). Thus, all reassortant viruses except one containing PR8 NA (7:1 reassortant) are 6:2 reassortant viruses with a PR8 background,

[e] Growth of wild-type PR8 was also assessed as a control for each experiment.

[f] Growth of each reassortant virus in eggs was assessed by either HA or infectivity assay, and reported as mean ± s.d. of HA titer ($log_2$)/mean ± s.d. of infectivity titer ($log_{10}EID_{50}$/ml). Significantly enhanced HA and infectivity titers (p < 0.05, t-test), by comparison to those of standard viruses containing VN1203 HA and VN1203 NA or VN1194 HA and VN1203 NA, are shown in boldface type.

ND, not determined.

titration (FIG. 6). Interestingly, even the 6:2 reassortant virus containing both its HA and NA from the VN1194 virus grew significantly better (about 7-fold, p=0.047) than NIBRG-14 (also a VN1194/PR8 6:2 reassortant virus) by plaque titration (FIG. 5). This difference in the growth of two 6:2 reassortant viruses possessing identical VN1194 HAs and NAs indicates that the PR8 strain used in this study would be superior to the one used to generate NIBRG-14 for supporting high viral growth during vaccine production in eggs.

TABLE 6

Growth comparison of H5N1/PR8 reassortant viruses generated in this study with the WHO-recommended vaccine seed virus (NIBRG-14)[a]

| | Infectivity titer ($log_{10}EID_{50}/ml$) | | | | |
|---|---|---|---|---|---|
| | Reassortants made in this study[b] | | | | NIBRG-14 |
| Hours Postinfection | VN1194/ VN1194 | VN1194/ PR8 | VN1203/ VN1203 | VN1203/ PR8 | VN1194/ VN1194 |
| 48 | 8.7 ± 0.4 | 9.4 ± 0.2 | 9.1 ± 0.2 | 9.5 ± 0.3 | 8.2 ± 0.3 |
| 60 | 8.3 ± 0.5 | 8.9 ± 0.5 | 8.6 ± 0.4 | 9.2 ± 0.3 | 7.4 ± 0.2 |

[a]Growth of reassortant viruses was assessed by inoculating eggs (n = 3) with each virus, harvesting allantoic fluid at the indicated times, and determining the $EID_{50}$. The data are shown as mean ± s.d. of infectivity titers ($log_{10}EID_{50}/ml$). Significantly enhanced infectivity titers (p < 0.05, t-test), by comparison with those of NIBRG-14, are shown in boldface type.
[b]Categorized by the derivation of the HA/NA. The HA cleavage site of both VN1203 and VN1194 were modified to that of the avirulent-type H5 HA.

Discussion

Recombinant viruses possessing modified avirulent-type HA and NA genes, both derived from an H5N1 human isolate, and all remaining genes from the PR8 strain (6:2 reassortant) have been produced and used as seed viruses for inactivated influenza vaccines now being tested in human clinical trials (Wood & Robertson, 2004). Seed strains used in this way must grow well in embryonated eggs. Although egg-adapted PR8 meets this requirement, some 6:2 reassortant viruses, despite containing six internal genes from PR8, do not grow well in eggs (Tables 3 and 5). Here it is demonstrated that the growth of egg-adapted PR8 in chicken eggs is affected by the functional balance of the HA and NA surface glycoproteins.

It is likely that low yields of some 6:2 reassortant viruses with a PR8 background and surface glycoproteins from highly pathogenic avian viruses may result not only from an HA-NA functional imbalance for growth in eggs but also from genetic (and/or functional) incompatibility between the avian surface glycoprotein genes and the internal genes from PR8. Here it is shown that among the internal genes of PR8, PB1 is very important for its high growth in eggs. This information suggests another strategy for reverse genetics-based H5N1 vaccine production: that is, the PB8 PB1 gene alone may be sufficient to generate vigorously growing reassortants for vaccine seed viruses. Thus, by using genes that encode non-PB1 internal proteins from strains other than PR8, one might avoid genetic incompatibility between avian and PR8 viruses. Studies to dissect the molecular basis for the high growth property of PR8 PB1 in eggs would be of considerable interest. One could, for example, analyze the structural and functional differences between the PB1s or PB1-F2s of PR8 and WSN (which differ by 18 and 10 amino acids, respectively: Chen et al., 2004).

The 7:1 reassortant viruses produced in this study replicated significantly better (more than 20-fold by plaque titration) than the WHO-recommended 6:2 reassortant virus NIBRG-14. Even the 6:2 reassortant that was identical to the NIBRG-14 except for the PR8 strain of origin replicated 7-fold better than the recommended virus. These findings suggest that the PR8 strain used in this study may be a superior donor virus for the production of reverse genetics-based pandemic vaccines.

One could argue that the 7:1 reassortant viruses would induce a loss of protective immune response due to antigenic differences in the NA proteins (even though both PR8 and the highly pathogenic viruses contain N1 NAs) (Murphy et al., 1972; Kilbourne et al., 1968; Chen et al., 2000). However, since the HA is the major protective antigen in inactivated vaccines, the higher growth property conferred by the PR8 NA would likely offset the limited antigenic mismatch in this minor protective antigen. In the event of a pandemic caused by a highly pathogenic avian influenza virus, chicken eggs will be in short supply. It is proposed that under such conditions, 7:1 reassortant-based vaccine seed viruses possessing an enhanced growth property in eggs would offer an attractive option for the generation of reverse genetics-based H5 vaccine viruses.

Example 4

To identify the genes responsible for the high growth rate of an H5N1 vaccine seed virus in chicken embryonated eggs, the growth of reassortant H5N1 viruses possessing PR8(UW) or PR8(Cambridge) internal genes in chicken embryonated eggs was assessed (FIG. 7). The HA and NA genes of all of the reassortant viruses were derived from A/Vietnam/1194/2002. All other genes were derived from either PR8(UW) or PR8(Cambridge), which also provided the non-HA and -NA genes of the NIBRG-14 vaccine strain. Higher titers were obtained when the majority of internal genes were from PR8(UW).

The effect of the M and NS genes on the growth of viruses in chicken embryonated eggs is shown in FIG. 8. For PR8(UW)/1194-CamM and PR8(UW)/1194-CamNS, the M and NS gene segments, respectively, were derived from PR8(Cambridge), while the other internal segments came from PR8(UW). The HA and NA segments were derived from A/Vietnam/1194/2004. Highest titers were with the M gene segment of PR8(UW) and the NS gene of PR8 (Cambridge).

The results in FIGS. 7-8 show that the polymerase subunit (PA, PB1, and PB2) and NP genes of PR8(UW) enhanced the growth of an H5N1 vaccine seed virus in chicken embryonated eggs. Also, the NS gene of PR8(Cambridge) enhanced the growth of an H5N1 vaccine seed virus in chicken embryonated eggs.

Figure 9:
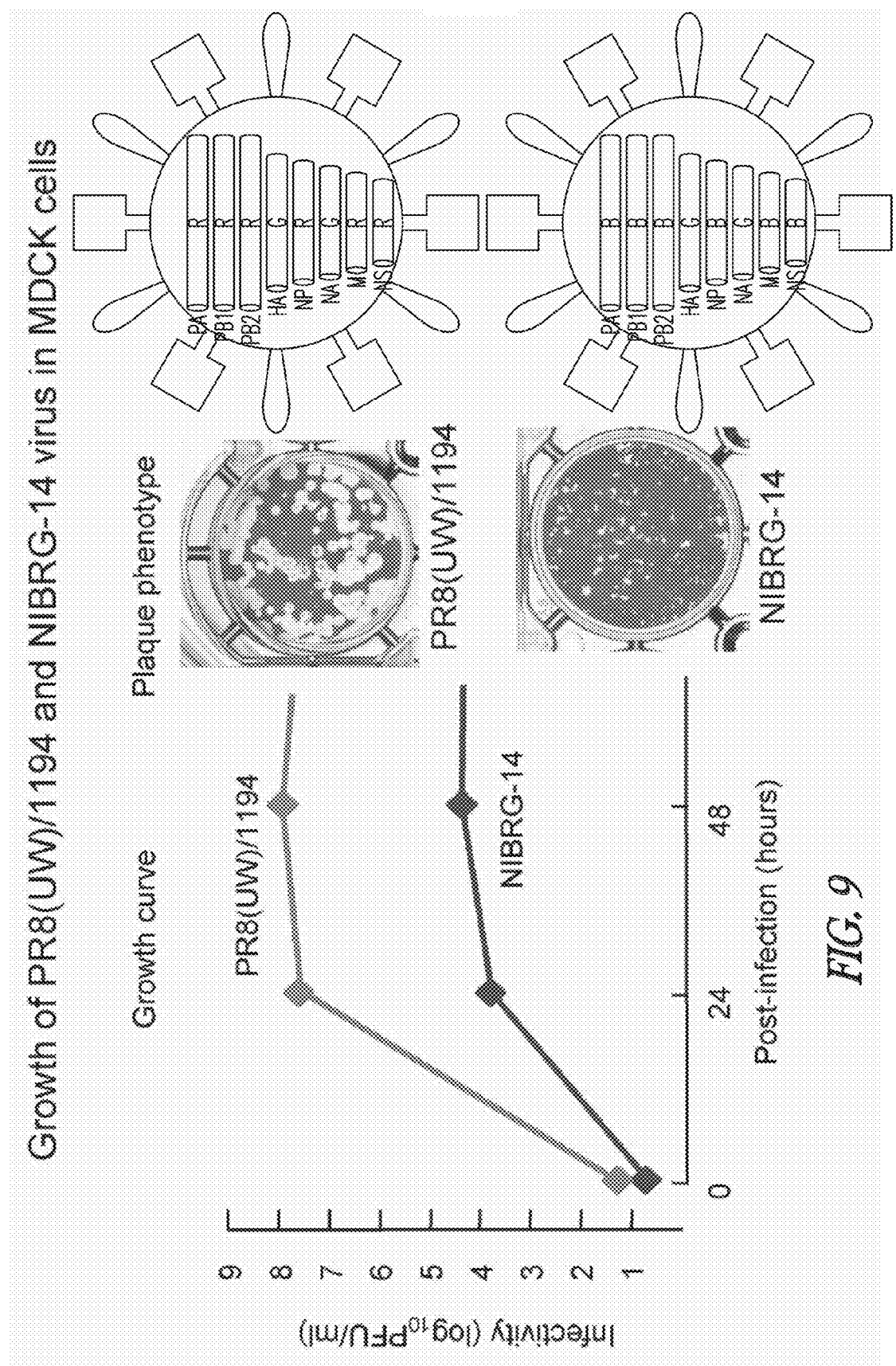
FIG. 9. Growth of PR8(UW)/1194 and NBRG-14 virus in MDCK cells.
Figure 10:
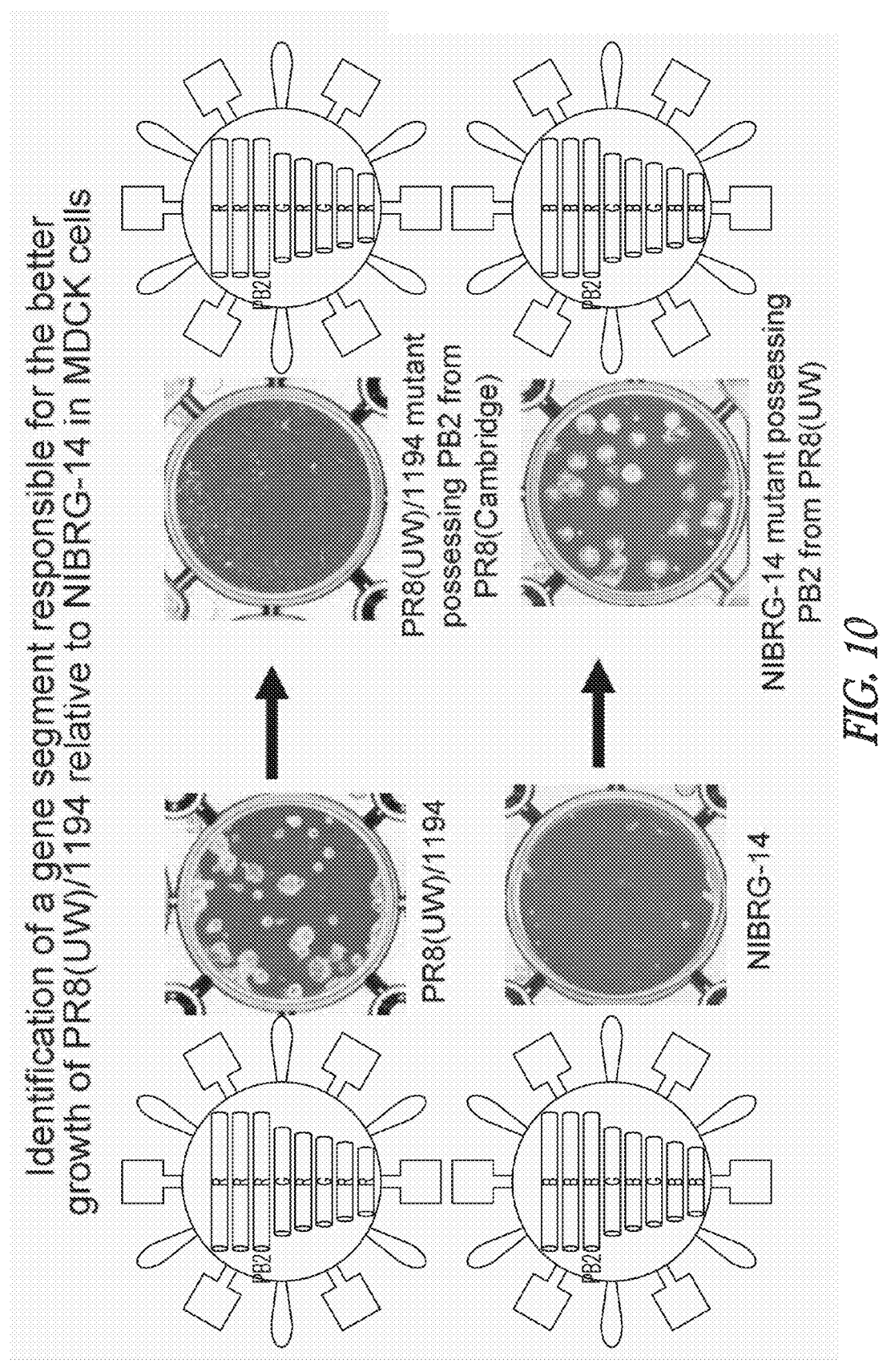
Figure 11:
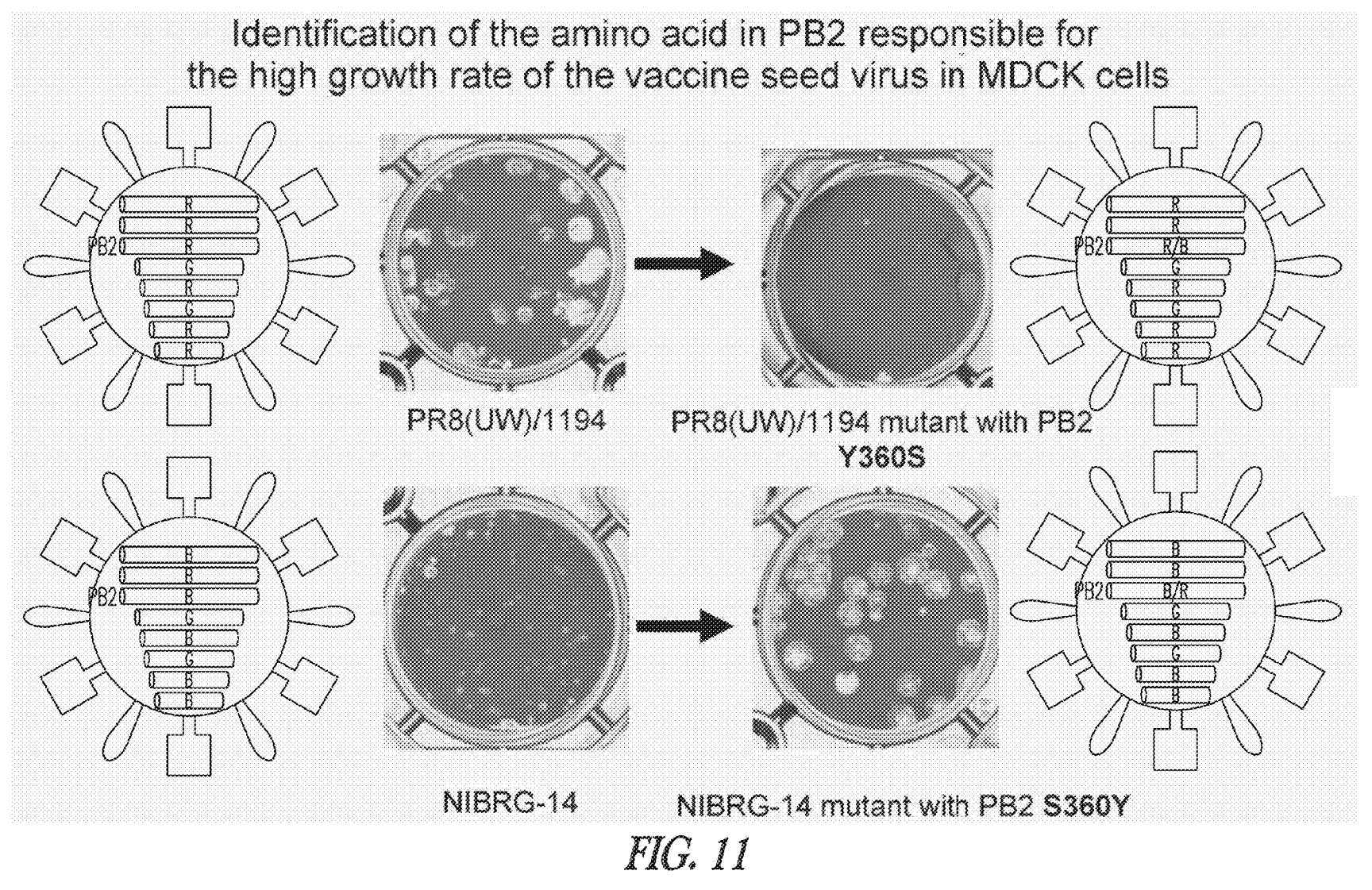

To identify the gene and amino acid(s) responsible for the high growth rate of the H5N1 vaccine seed virus in MDCK cells, the growth of PR8(UW)/1194 and NIBRG-14 virus in MDCK cells was assessed. The data in FIG. 9 show that the growth of PR8(UW)/1194 was significantly better than that of NIBRG-14 in MDCK cells. Moreover, the PB2 segment of PR8(UW) enhanced the growth of the vaccine seed virus in MDCK cells (FIG. 10). The tyrosine residue at position 360 in PB2 of PR8(UW) is likely responsible for the high growth rate of the vaccine seed virus in MDCK cells (FIG. 11).

To identify a combination of genes responsible for the high growth of an H5N1 vaccine seed virus in MDCK cells, the growth rates in MDCK cells of reassortants with different HA, NA, and NS genes was determined. NS from PR8(Cambridge) and NA with a long stalk (e.g., from A/Hong Kong/213/2003 or VN1203Fill) enhanced virus growth in MDCK cells (FIG. 12).

Figure 13:
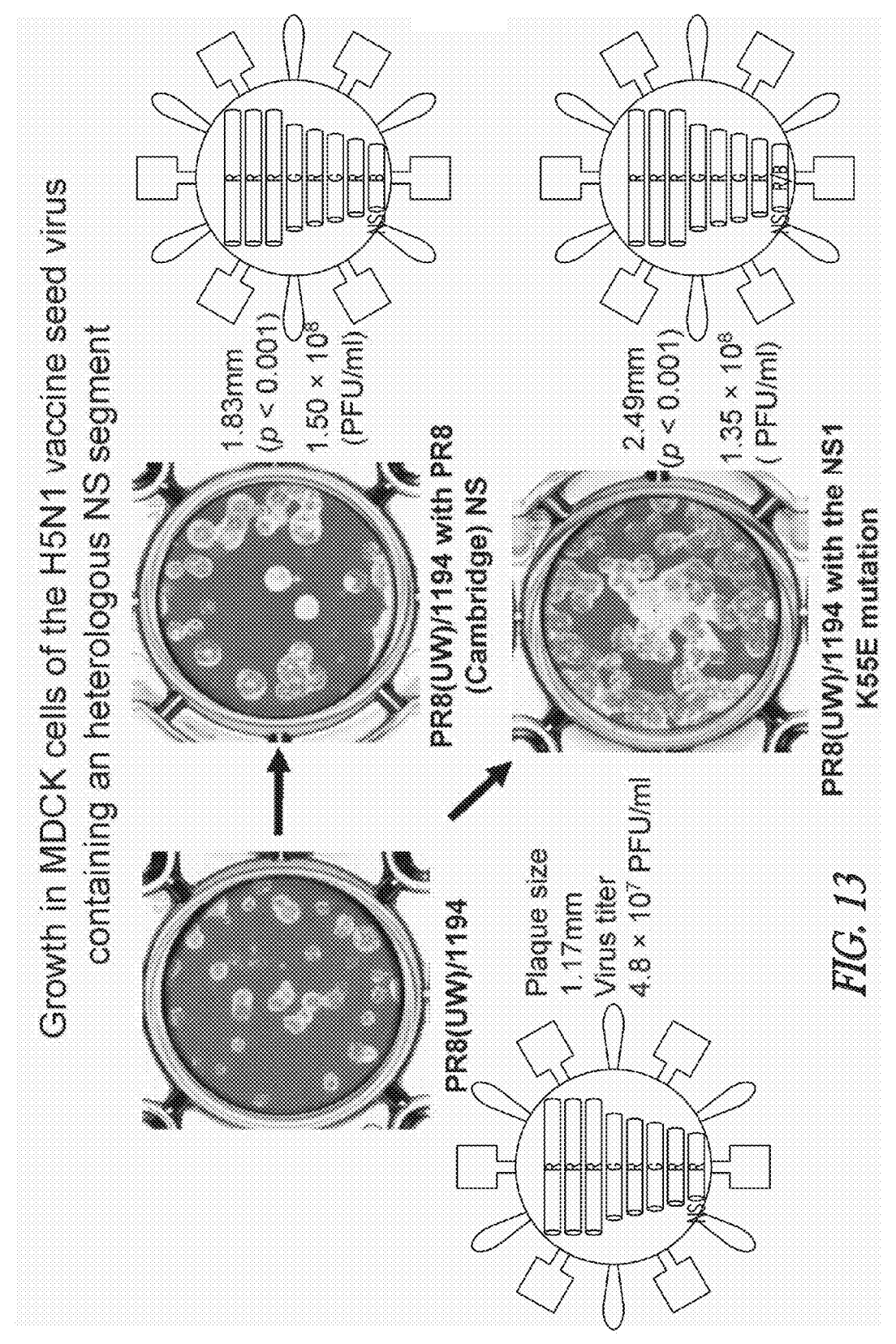

To determine which amino acids in NS are responsible for the high growth rate of the H5N1 vaccine seed virus in MDCK cells, the growth in MDCK cells of the H5N1 vaccine seed virus containing a heterologous NS segment was measured. An amino acid substitution from K [PR8 (UW)NS] to E [PR8(Cambridge)] at position 55 of NS1 enhanced the growth of the H5N1 vaccine seed viruses in MDCK cells (FIG. 13).

Figure 14:
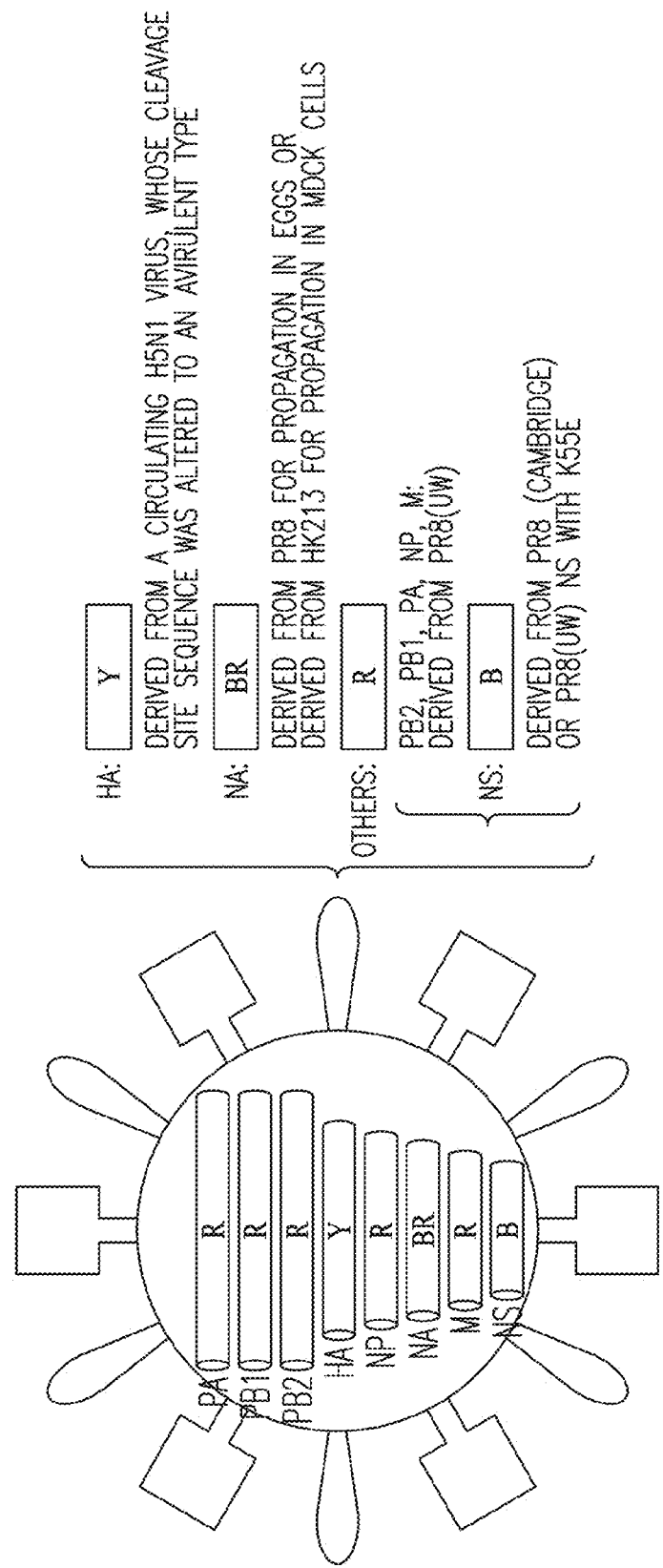
FIG. 14. Schematic of the genotype of an H5N1 vaccine seed virus with high growth capacity in chicken embryonated eggs or MDCK cells.

FIG. 14 summarizes the genotype of an H5N1 seed virus with high growth capacity in chicken embryonated eggs or MDCK cells.

REFERENCES

Avery's Drug Treatment: Principles and Practice of Clinical Pharmacology and Therapeutics, 3rd edition, ADIS Press, Ltd., Williams and Wilkins, Baltimore, Md. (1987).
Aymard-Henry et al., Virology: A Practical Approach, Oxford IRL Press, Oxford, 119-150 (1985).
Bachmeyer, Intervirology, 5:260 (1975).
Berkow et al., eds., The Merck Manual, 16th edition, Merck & Co., Rahway, N.J. (1992).
Bridgen et al., Proc. Natl. Acad. Sci. U.S.A 93:15400 (1996).
Castrucci & Kawaoka, J. Virol., 67:759 (1993).
Castrucci et al., J. Virol., 69:2725 (1995).
Chen et al., Emerg. Infect. Dis., 10:630 (2004).
Chen et al., Vaccine, 18:3214 (2000).
Claas et al., Lancet, 351:472 (1998).
Conzelmann et al., J. Gen. Virol., 77:381 (1996).
Conzelmann et al., Trends Microbiol., 4:386 (1996).
Conzelmann. Annu. Rev. Genet., 32:123 (1998).
Cozelmann et al., J. Virol., 68:713 (1994).
Edwards, J. Infect. Dis., 169: 68 (1994).
Enami et al., Proc. Natl. Acad. Sci. U.S.A., 87:3802 (1990).
Enami et al., Virology, 185:291 (1991).
Fodor et al., J. Virol., 73:9679 (1999).
Grand and Skehel, Nature, New Biology, 238:145 (1972).
Hatta et al., Science, 293:1840 (2001).
Horimoto et al., J. Virol., 68:3120 (1994).
Horimoto et al., Vaccine, 24:3669 (2006).
Keitel et al., in Textbook of Influenza, eds. Nickolson, K. G., Webster, R. G., and Hay, A. (Blackwell, Oxford), pp. 373-390 (1998).
Kendal et al., Infect. Immunity, 29:966 (1980).
Kilbourne et al., J. Virol., 2:281 (1968).
Kilbourne, Bull. M2 World Health Org., 41: 653 (1969).
Kilbourne, Bull. World Health Org., 41:643 (1969).
Kobasa et al., Naure, 431:703 (2004).
Kovesdi et al., J. Curr. Opin. Biotechnol., 8:583 (1997).
Laver & Webster, Virology, 69:511 (1976).
Lawson et al., Proc. Natl. Acad. Sci. U.S.A 92:4477 (1995).
Li et al., Nature 430:209 (2004).
Marriott et al., Adv. Virus Res., 53:321 (1999).
Mizrahi, (ed.), Viral Vaccines, Wiley-Liss, New York, 39-67 (1990).
Munoz et al., Antiviral Res., 46:91 (2000).
Murphy et al., New Engl. J. Med., 286:1329 (1972).
Murphy, Infect. Dis. Clin. Pract., 2: 174 (1993).
Muster et al., Proc. Natl. Acad. Sci. USA, 88: 5177 (1991).
Nagai et al., Microbiol. Immunol., 43:613 (1999).
Nagai, Rev. Med. Virol. 2:83 (1999).
Neumann et al., Adv. Virus Res., 53:265 (1999).
Neumann et al., J. Gen. Virol., 83:2635 (2002).
Neumann et al., J. Virol., 71:9690 (1997).
Neumann et al., Proc. Natl. Acad. Sci. USA, 96:9345 (1999).
Neumann et al., Virology, 287:243 (2001).
Ogra et al., J. Infect. Dis., 134: 499 (1977).
Osol (ed.), Remington's Pharmaceutical Sciences, Mack Publishing Co., Easton, Pa. 1324-1341 (1980).
Parks et al., J. Virol., 73:3560 (1999).
Peiris et al., Lancet, 363:617 (2004).
Pekosz et al., Proc. Natl. Acad. Sci. U. S. A, 96:8804 (1999).
Radecke et al., EMBO J., 14:5773 (1995).
Roberts et al., Virology. 247:1 (1998).
Robertson et al., Biologicals. 20:213 (1992).
Robertson et al., Giornale di Igiene e Medicina Preventiva, 29:4 (1988).
Rose, Proc. Natl. Acad. Sci. U. S. A, 93:14998 (1996).
Schnell et al., EMBO J. 13:4195 (1994).
Stephenson et al., Lancet Inf. Dis., 4:499 (2004).
Subbarao et al., J. Virol., 67:7223 (1993).
Subbarao et al., Science, 279:393 (1998).
Subbarao et al., Virology, 305:192 (2003).
Sugawara et al., Biologicals, 30:303 (2002).
Webby & Webster et al., Science, 302:1519 (2003).
Webby et al., Lancet, 363:1099 (2004).
Wood & Robertson, Nat. Rev. Microbiol., 2:842 (2004).
World Health Organization TSR No. 673 (1982).
World Health Organization. Confirmed human cases of avian influenza A (H5N1). http://www.who.int/csr/disease/avian_influenza/country/en/index.html
Xu et al., Virology. 261:15 (1999).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A composition comprising a plurality of influenza virus vectors, comprising a) i) a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the cDNAs for PB1, PB2, PA, NP, NA, and M have sequences that encode a polypeptide having at least 99% contiguous amino acid sequence identity to a corresponding polypeptide encoded by SEQ ID NOs:1-5 and a polypeptide having at least 90% contiguous amino acid sequence identity to a corresponding polypeptide encoded by SEQ ID NO:8, a cDNA for NS that has a Glu residue at position 55 corresponding to position 55 in a NS1 polypeptide encoded by SEQ ID NO:38 and encodes a polypeptide having at least 97% contiguous amino acid sequence identity to a corresponding polypeptide encoded by SEQ ID NO:6, and wherein the cDNA for HA has sequences from a different influenza virus strain than a strain having gene segments with sequences corresponding to the cDNAs for PB1, PB2, PA, NP, M, NS, and NA having SEQ ID Nos. 1-6 and 8; or ii) a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the cDNAs for PB1, PB2, PA, NP, and M have sequences that encode a polypeptide having at least 99% contiguous amino acid sequence identity to a corresponding polypeptide encoded by SEQ ID NOs:1-5, a cDNA for NS that has a Glu residue at position 55 corresponding to position 55 in a NS1 polypeptide encoded by SEQ ID NO:38 and encodes a polypeptide having at least 97% contiguous amino acid sequence identity to a corresponding polypeptide encoded by SEQ ID NO:6, wherein the cDNA for NA is from the one or more influenza viruses that replicate to high titers in embryonated eggs or has sequences for a heterologous NA, and wherein the cDNA for HA has sequences for a heterologous HA;

or iii) a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the cDNAs for PB1, PB2, PA, NP, and M have sequences that encode a polypeptide having at least 99% contiguous amino acid sequence identity to a corresponding polypeptide encoded by SEQ ID NOs:1-5, wherein the PB2 has a tyrosine at position 360, a cDNA for NS that has a Glu residue at position 55 corresponding to position 55 in a NS1 polypeptide encoded by SEQ ID NO:38 and encodes a polypeptide having at least 97% contiguous amino acid sequence identity to a corresponding polypeptide encoded by SEQ ID NO:6, wherein the cDNA for NA has sequences for a heterologous NA, and wherein the cDNA for HA has sequences for a heterologous HA; and b) a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, and a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus M2, or a vector comprising a promoter operably linked to a DNA segment encoding influenza virus NS2, wherein the plurality of vectors of a)i) or a)ii) and b), when introduced to cells, result in production of influenza virus which is capable of enhanced replication in embryonated eggs relative to a corresponding influenza virus that does not have a NA with sequences that encode polypeptide having at least 90% contiguous amino acid sequence identity to a corresponding polypeptide encoded by SEQ ID NO:8, does not have a NA from an influenza virus that replicates to high titers in embryonated eggs or does not have sequences for a heterologous NA, or does not have a NS with a Glu residue at position 55 corresponding to position 55 in a NS1 polypeptide encoded by SEQ ID NO:38; or wherein the plurality of vectors of a)iii) and b), when introduced to cells, result in production of influenza virus which is capable of enhanced replication in MDCK cells relative to a corresponding influenza virus that does not have a NA with sequences for a heterologous NA, has a PB2 with a serine at position 360, or does not have a NS with a Glu residue at position 55 corresponding to position 55 in a NS1 polypeptide encoded by SEQ ID NO:38.

2. The composition of claim 1, wherein the cDNAs for PB1, PB2, PA, NP, and M encode a polypeptide encoded by SEQ ID NOs:1-5.

3. The composition of claim 1, wherein the cDNA for NS encodes a polypeptide encoded by SEQ ID NO:38.

4. The composition of claim 1, wherein the promoter is a RNA polymerase I promoter, a RNA polymerase II promoter, a RNA polymerase III promoter, a T3 promoter or a T7 promoter.

5. The composition of claim 1, wherein a plurality of the vectors of a) comprise a RNA polymerase I promoter or a RNA polymerase II promoter.

6. The composition of claim 5, wherein the RNA polymerase I promoter is a human RNA polymerase I promoter.

7. The composition of claim 1, wherein each vector of a) is on a separate plasmid.

8. The composition of claim 1, wherein the NA or HA is a chimeric NA or HA.

9. The composition of claim 1, wherein the cDNA for HA does not encode a polypeptide corresponding to the polypeptide encoded by SEQ ID NO:7.

10. A method to prepare influenza virus, comprising: contacting a cell with one of:
i) a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the cDNAs for PB1, PB2, PA, NP, NA, and M have sequences that encode a polypeptide having at least 99% contiguous amino acid sequence identity to a corresponding polypeptide encoded by SEQ ID NOs:1-5 and a polypeptide having at least 90% contiguous amino acid sequence identity to a corresponding polypeptide encoded by SEQ ID NO:8, a cDNA for NS that has a Glu residue at position 55 corresponding to position 55 in a NS1 polypeptide encoded by SEQ ID NO:38 and encodes a polypeptide having at least 97% contiguous amino acid sequence identity to a corresponding polypeptide encoded by SEQ ID NO:6, and wherein the cDNA for HA has sequences from a different influenza virus strain than a strain having gene segments with sequences corresponding to the cDNAs for PB1, PB2, PA, NP, M, NS, and NA having SEQ ID Nos. 1-6 and 8;

and a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, and a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus M2, or a vector comprising a promoter operably linked to a DNA segment encoding influenza virus NS2;

ii) a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the cDNAs for PB1, PB2, PA, NP, and M have sequences that encode a polypeptide having at least 99% contiguous amino acid sequence identity to a corresponding polypeptide encoded by SEQ ID NOs:1-5, a cDNA for NS that has a Glu residue at position 55 corresponding to position 55 in a NS1 polypeptide encoded by SEQ ID NO:38 and encodes a polypeptide having at least 97% contiguous amino acid sequence identity to a corresponding polypeptide encoded by SEQ ID NO:6, wherein the cDNA for NA is from the one or more influenza viruses that replicate to high titers in embryonated eggs or has sequences for a heterologous NA, and wherein the cDNA for HA has sequences for a heterologous HA; and a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, and a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus M2, or a vector comprising a promoter operably linked to a DNA segment encoding influenza virus NS2; or iii) a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising a promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the cDNAs for PB1, PB2, PA, NP, and M have sequences that encode a polypeptide having at least 99% contiguous amino acid sequence identity to a corresponding polypeptide encoded by SEQ ID NOs:1-5, wherein the PB2 has a tyrosine at position 360, a cDNA for NS that has a Glu residue at position 55 corresponding to position 55 in a NS1 polypeptide encoded by SEQ ID NO:38 and encodes a polypeptide having at least 97% contiguous amino acid sequence identity to a corresponding polypeptide encoded by SEQ ID NO:6, wherein the cDNA for NA has sequences for a heterologous NA, and wherein the cDNA for HA has sequences for a heterologous HA; and a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, and a vector comprising a promoter operably linked to a DNA segment encoding influenza virus NP, and optionally a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding influenza virus M2, or a vector comprising a promoter operably linked to a DNA segment encoding influenza virus NS2;

in an amount effective to yield infectious influenza virus, wherein the vectors of i) or ii), when introduced to cells, result in production of influenza virus which is capable of enhanced replication in embryonated eggs relative to a corresponding influenza virus that does not have a NA with sequences that encode polypeptide having at least 90% contiguous amino acid sequence identity to a corresponding polypeptide encoded by SEQ ID NO:8, does not have a NA from an influenza virus that replicates to high titers in embryonated eggs or does not have sequences for a heterologous NA, or does not have a NS with a Glu residue at position 55 corresponding to position 55 in a NS1 polypeptide encoded by SEQ ID NO:38; or wherein the vectors of iii), when introduced to cells, result in production of influenza virus which is capable of enhanced replication in MDCK cells relative to a corresponding influenza virus that does not have a NA with sequences for a heterologous NA, has a PB2 with a serine at position 360, or does not have a NS with a Glu residue at position 55 corresponding to position 55 in a NS1 polypeptide encoded by SEQ ID NO:38.

11. The method of claim 10 further comprising isolating the virus.

12. An isolated recombinant influenza virus comprising i) a viral segment for PB1, PB2, PA, NP, M, and NA that is from an influenza virus that replicates to high titers in embryonated eggs, a viral segment for NS with a Glu residue at position 55 which corresponds to position 55 in a NS1 polypeptide encoded by SEQ ID NO:6, and a viral segment for a heterologous HA; ii) a viral segment for PB1, PB2, PA, NP, and M that is from an influenza virus that replicates to high titers in embryonated eggs, a viral segment for NS with a Glu residue at position 55 which corresponds to position 55 in a NS1 polypeptide encoded by SEQ ID NO:6, a viral segment for NA that is from a virus that replicates to high titers in embryonated eggs, and a viral segment for a heterologous HA; or iii) a viral segment for PB2 that encodes a PB2 having at least 99% amino acid sequence identity to a PB2 encoded by SEQ ID NO:3 or SEQ ID NO:33 which PB2 has a serine or tyrosine at position 360 which corresponds to position 360 in a PB2 polypeptide encoded by SEQ ID NO:3 but which viral segment does not encode a PB2 encoded by SEQ ID NO:3 or SEQ ID NO:33.

13. The isolated recombinant virus of claim 12, wherein the influenza virus that replicates to high titers is PR8HG.

14. The isolated recombinant influenza virus of claim 12 ii, wherein the viral segment for PB1, PB2, PA, NP, and M is from PR8HG.

15. The isolated recombinant influenza virus of claim 12 ii, wherein the viral segment for NA is from PR8.

16. The isolated recombinant influenza virus of claim 12 ii, wherein the viral segment for NA is heterologous to the viral segments for PB1, PB2, PA, NP, and M.

17. The isolated recombinant influenza virus of claim 12 ii, wherein the viral segment for HA is for H5.

18. The isolated recombinant virus of claim 12 iii, which has one or more but less than 20 substitutions relative to SEQ ID NO:3.

19. The isolated recombinant virus of claim 18, wherein the one or more substitutions include conservative substitutions.

20. The composition of claim 1 a)i), wherein the PB2 has a serine at position 360.

21. The composition of claim 1 a)ii), wherein the cDNAs for PB1, PB2, PA, or NP encode a polypeptide encoded by one of SEQ ID NOs:33-36.

22. The composition of claim 1 a)ii), wherein the PB2 has a serine at position 360.

23. The composition of claim 1 a)iii), wherein the cDNAs for PB1, PB2, PA, and NP do not encode a polypeptide encoded by one of SEQ ID NOs:33-36.

* * * * *

SEQUENCE LISTING

<160> NUMBER OF SEQ ID NOS: 38

<210> SEQ ID NO 1
<211> LENGTH: 2233
<212> TYPE: DNA
<213> ORGANISM: Influenza A

<400> SEQUENCE: 1

```
agcgaaagca ggtactgatc caaaatggaa gattttgtgc gacaatgctt caatccgatg      60
attgtcgagc ttgcggaaaa aacaatgaaa gagtatgggg aggacctgaa aatcgaaaca     120
```

```
aacaaatttg cagcaatatg cactcacttg gaagtatgct tcatgtattc agattttcac    180
ttcatcaatg agcaaggcga gtcaataatc gtagaacttg gtgatccaaa tgcacttttg    240
aagcacagat ttgaaataat cgagggaaga gatcgcacaa tggcctggac agtagtaaac    300
agtatttgca acactacagg ggctgagaaa ccaaagtttc taccagattt gtatgattac    360
aaggagaata gattcatcga aattggagta acaaggagag aagttcacat atactatctg    420
gaaaaggcca ataaaattaa atctgagaaa acacacatcc acattttctc gttcactggg    480
gaagaaatgg ccacaaaggc agactacact ctcgatgaag aaagcagggc taggatcaaa    540
accagactat tcaccataag acaagaaatg ccagcagag gcctctggga ttcctttcgt     600
cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc ttttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaaaggg aataaatcca   1020
aattatcttc tgtcatggaa gcaagtactg cagaactgc aggacattga gaatgaggag    1080
aaaattccaa agactaaaaa tatgaagaaa acaagtcagc taaagtgggc acttggtgag   1140
aacatggcac cagaaaaggt agactttgac gactgtaaag atgtaggtga tttgaagcaa   1200
tatgatagtg atgaaccaga attgaggtcg cttgcaagtt ggattcagaa tgagtttaac   1260
aaggcatgcg aactgacaga ttcaagctgg atagagctcg atgagattgg agaagatgtg   1320
gctccaattg aacacattgc aagcatgaga aggaattatt tcacatcaga ggtgtctcac   1380
tgcagagcca cagaatacat aatgaaggga gtgtacatca atactgcctt gcttaatgca   1440
tcttgtgcag caatggatga tttccaatta attccaatga taagcaagtg tagaactaag   1500
gagggaaggc gaaagaccaa cttgtatggt tcatcataa aaggaagatc ccacttaagg    1560
aatgacaccg acgtggtaaa cttttgtgagc atggagtttt ctctcactga cccaagactt   1620
gaaccacata atgggagaa gtactgtgtt cttgagatag gagatatgct tataagaagt    1680
gccataggcc aggtttcaag gcccatgttc ttgtatgtga gaacaaatgg aacctcaaaa   1740
attaaaatga aatggggaat ggagatgagg cgttgcctcc tccagtcact tcaacaaatt   1800
gagagtatga ttgaagctga gtcctctgtc aaagagaaag acatgaccaa agagttcttt   1860
gagaacaaat cagaaacatg gcccattgga gagtccccca aggagtgga ggaaagttcc    1920 attgggaagg tctgcaggac tttattagca aagtcggtat tcaacagctt gtatgcatct   1980
ccacaactag aaggattttc agctgaatca agaaaactgc ttcttatcgt tcaggctctt   2040
agggacaacc tggaacctgg gacctttgat cttggggggc tatatgaagc aattgaggag   2100
tgcctgatta atgatccctg ggttttgctt aatgcttctt ggttcaactc cttccttaca   2160
catgcattga gttagttgtg gcagtgctac tatttgctat ccatactgtc caaaaaagta   2220 ccttgttct act                                                       2233

<210> SEQ ID NO 2
<211> LENGTH: 2341
<212> TYPE: DNA
<213> ORGANISM: Influenza A
```

```
<400> SEQUENCE: 2
agcgaaagca ggcaaaccat ttgaatggat gtcaatccga ccttacttt cttaaaagtg      60 ccagcacaaa atgctataag cacaacttc ccttatactg gagaccctcc ttacagccat     120
gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
gctttccttg aggaatccca tcctggtatt tttgaaaact cgtgtattga aacgatggag    360
gttgttcagc aaaacgagt agacaagctg acacaaggcc gacagaccta tgactggact    420
ctaaatagaa accaacctgc tgcaacagca ttggccaaca caatagaagt gttcagatca    480
aatggcctca cggccaatga gtctggaagg ctcatagact ccttaagga tgtaatggag    540 tcaatgaaca agaagaaat ggggatcaca actcatttc agagaaagag acgggtgaga     600
gacaatatga ctaagaaaat gataacacag agaacaatgg gtaaaagaa gcagagattg    660 aacaaaagga gttatctaat tagagcattg accctgaaca caatgaccaa agatgctgag    720
agagggaagc taaaacggag agcaattgca accccaggga tgcaaataag ggggtttgta    780
tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaactttc tttccaccatc actggagata caccaaatg gaacgaaaat    960 cagaatcctc ggatgttttt ggccatgatc acatatatga ccagaaatca gcccgaatgg   1020
ttcagaaatg ttctaagtat tgctccaata atgttctcaa acaaaatggc gagactggga   1080 aagggtata tgtttgagag caagagtatg aaacttagaa ctcaaatacc tgcagaaatg   1140
ctagcaagca tcgatttgaa atatttcaat gattcaacaa gaagaagat tgaaaaaatc   1200 cgaccgctct aatagaggg gactgcatca ttgagccctg aatgatgat gggcatgttc   1260 aatatgttaa gcactgtatt aggcgtctcc atcctgaatc ttggacaaaa gagatacacc   1320
aagactactt actggtggga tggtcttcaa tcctctgacg attttgctct gattgtgaat   1380
gcacccaatc atgaagggat tcaagccgga gtcgacaggt tttatcgaac ctgtaagcta   1440
cttggaatca atatgagcaa gaaaaagtct tacataaaca gaacaggtac atttgaattc   1500
acaagttttt tctatcgtta tgggtttgtt gccaatttca gcatggagct tcccagtttt   1560
ggggtgtctg ggatcaacga gtcagcggac atgagtattg gagttactgt catcaaaaac   1620
aatatgataa acaatgatct tggtccagca acagctcaaa tggcccttca gttgttcatc   1680
aaagattaca ggtacacgta ccgatgccat ataggtgaca cacaaataca aacccgaaga   1740
tcatttgaaa taagaaact gtgggagcaa acccgttcca aagctggact gctggtctcc   1800
gacggaggcc caaatttata caacattaga atctccaca ttcctgaagt ctgcctaaaa   1860
tgggaattga tggatgagga ttaccagggg cgtttatgca acccactgaa cccatttgtc   1920
agccataaag aaattgaatc aatgaacaat gcagtgatga tgccagcaca tggtccagcc   1980
aaaaacatgg agtatgatgc tgttgcaaca acacactcct ggatccccaa agaaatcga   2040 tccatcttga atacaagtca agaggagta cttgaggatg aacaaatgta ccaaaggtgc   2100
tgcaatttat ttgaaaaatt cttccccagc agttcataca agaccagtc gggatatcc   2160 agtatggtgg aggctatggt ttccagagcc cgaattgatg cacggattga tttcgaatct   2220
ggaaggataa agaagaaga gttcactgag atcatgaaga tctgttccac cattgaagag   2280
ctcagacggc aaaaatagtg aatttagctt gtccttcatg aaaaaatgcc ttgtttctac   2340
```

-continued t 2341

<210> SEQ ID NO 3
<211> LENGTH: 2341
<212> TYPE: DNA
<213> ORGANISM: Influenza A

<400> SEQUENCE: 3
agcgaaagca ggtcaattat attcaatatg gaaagaataa aagaactacg aaatctaatg 60
tcgcagtctc gcacccgcga gatactcaca aaaaccaccg tggaccatat ggccataatc 120
aagaagtaca catcaggaag acaggagaag aacccagcac ttaggatgaa atggatgatg 180
gcaatgaaat atccaattac agcagacaag aggataacgg aaatgattcc tgagagaaat 240
gagcaaggac aaactttatg gagtaaaatg aatgatgccg gatcagaccg agtgatggta 300
tcacctctgg ctgtgacatg gtggaatagg aatggaccaa taacaaatac agttcattat 360
ccaaaaatct acaaaactta ttttgaaaga gtcgaaaggc taaagcatgg aacctttggc 420
cctgtccatt ttagaaacca agtcaaaata cgtcggagag ttgacataaa tcctggtcat 480
gcagatctca gtgccaagga ggcacaggat gtaatcatgg aagttgtttt ccctaacgaa 540
gtgggagcca ggatactaac atcggaatcg caactaacga taaccaaaga gaagaaagaa 600
gaactccagg attgcaaaat ttctcctttg atggttgcat acatgttgga gagagaactg 660
gtccgcaaaa cgagattcct cccagtggct ggtggaacaa gcagtgtgta cattgaagtg 720
ttgcatttga ctcaaggaac atgctgggaa cagatgtata ctccaggagg ggaagtgagg 780
aatgatgatg ttgatcaaag cttgattatt gctgctagga acatagtgag aagagctgca 840
gtatcagcag atccactagc atctttattg gagatgtgcc acagcacaca gattggtgga 900
attaggatgg tagacatcct taggcagaac ccaacagaag agcaagccgt ggatatatgc 960
aaggctgcaa tgggactgag aattagctca tccttcagtt ttggtggatt cacatttaag 1020
agaacaagcg gatcatcagt caagagagag gaagaggtgc ttacgggcaa tcttcaaaca 1080
ttgaagataa gagtgcatga gggatatgaa gagttcacaa tggttgggag aagagcaaca 1140
gccatactca gaaaagcaac caggagattg attcagctga tagtgagtgg gagagacgaa 1200
cagtcgattg ccgaagcaat aattgtggcc atggtatttt cacaagagga ttgtatgata 1260
aaagcagtca gaggtgatct gaatttcgtc aatagggcga atcaacgatt gaatcctatg 1320
catcaacttt taagacattt tcagaaggat gcgaaagtgc tttttcaaaa ttggggagtt 1380
gaacctatcg acaatgtgat gggaatgatt gggatattgc ccgacatgac tccaagcatc 1440
gagatgtcaa tgagaggagt gagaatcagc aaaatgggtg tagatgagta ctccagcacg 1500
gagagggtag tggtgagcat tgaccgtttt ttgagaatcc gggaccaacg aggaaatgta 1560
ctactgtctc ccgaggaggt cagtgaaaca cagggaacag agaaactgac aataacttac 1620
tcatcgtcaa tgatgtggga gattaatggt cctgaatcag tgttggtcaa tacctatcaa 1680
tggatcatca gaaactggga aactgttaaa attcagtggt cccagaaccc tacaatgcta 1740
tacaataaaa tggaatttga accatttcag tctttagtac ctaaggccat tagaggccaa 1800
tacagtgggt ttgtaagaac tctgttccaa caaatgaggg atgtgcttgg gacatttgat 1860
accgcacaga taataaaact tcttcccttc gcagccgctc caccaaagca aagtagaatg 1920
cagttctcct catttactgt gaatgtgagg ggatcaggaa tgagaatact tgtaaggggc 1980
aattctcctg tattcaacta taacaaggcc acgaagagac tcacagttct cggaaaggat 2040

```
gctggcactt taactgaaga cccagatgaa ggcacagctg gagtggagtc cgctgttctg    2100 agggattcc tcattctggg caaagaagac aagagatatg gccagcact aagcatcaat    2160 gaactgagca accttgcgaa aggagagaag gctaatgtgc taattgggca aggagacgtg    2220
gtgttggtaa tgaaacggaa acgggactct agcatactta ctgacagcca gacagcgacc    2280
aaaagaattc ggatggccat caattagtgt cgaatagttt aaaaacgacc ttgtttctac    2340
t                                                                     2341
```

<210> SEQ ID NO 4
<211> LENGTH: 1565
<212> TYPE: DNA
<213> ORGANISM: Influenza A

<400> SEQUENCE: 4

```
agcaaaagca gggtagataa tcactcactg agtgacatca aaatcatggc gtctcaaggc      60
accaaacgat cttacgaaca gatggagact gatggagaac gccagaatgc cactgaaatc     120
agagcatccg tcggaaaaat gattggtgga attgacgat tctacatcca aatgtgcacc     180
gaactcaaac tcagtgatta tgagggacgg ttgatccaaa acagcttaac aatagagaga     240
atggtgctct ctgcttttga cgaaaggaga ataaatacc ttgaagaaca tcccagtgcg     300
gggaaagatc ctaagaaaac tggaggacct atatcagga gagtaaacgg aaagtggatg     360
agagaactca tcctttatga caaagaagaa ataaggcgca tctggcgcca agctaataat     420
ggtgacgatg caacggctgg tctgactcac atgatgatct ggcattccaa tttgaatgat     480
gcaacttatc agaggacaag agctcttgtt cgcaccggaa tggatcccag gatgtgctct     540
ctgatgcaag gttcaactct ccctaggagg tctggagccg caggtgctgc agtcaaagga     600
gttggaacaa tggtgatgga attggtcaga atgatcaaac gtgggatcaa tgatcggaac     660
ttctggaggg gtgagaatgg acgaaaaaca agaattgctt atgaaagaat gtgcaacatt     720
ctcaaaggga aatttcaaac tgctgcacaa aaagcaatga tggatcaagt gagagagagc     780
cggaacccag ggaatgctga gttcgaagat ctcactttc tagcacggtc tgcactcata     840
ttgagagggt cggttgctca caagtcctgc ctgcctgcct gtgtgtatgg acctgccgta     900
gccagtgggt acgactttga aagggaggga tactctctag tcggaataga cccttttcaga     960 ctgcttcaaa acagccaagt gtacagccta atcagaccaa atgagaatcc agcacacaag    1020
agtcaactgg tgtggatggc atgccattct gccgcatttg aagatctaag agtattaagc    1080
ttcatcaaag gacgaaggt gctcccaaga gggaagcttt ccactagagg agttcaaatt    1140
gcttccaatg aaaatatgga gactatggaa tcaagtacac ttgaactgag aagcaggtac    1200
tgggccataa ggaccagaag tggaggaaac accaatcaac agagggcatc tgcgggccaa    1260
atcagcatac aacctacgtt ctcagtacag agaaatctcc cttttgacag aacaaccatt    1320
atggcagcat tcaatgggaa tacagagggg agaaacatctg acatgaggac cgaaatcata    1380
aggatgatgg aaagtgcaag accagaagat gtgtctttcc aggggcgggg agtcttcgag    1440
ctctcggacg aaaaggcagc gagcccgatc gtgccttcct ttgacatgag taatgaagga    1500
tcttatttct tcggagacaa tgcagaggag tacgacaatt aaagaaaaat accccttgttt    1560 ctact                                                               1565
```

<210> SEQ ID NO 5
<211> LENGTH: 1027
<212> TYPE: DNA
<213> ORGANISM: Influenza A

<400> SEQUENCE: 5

```
agcaaaagca ggtagatatt gaaagatgag tcttctaacc gaggtcgaaa cgtacgtact      60
ctctatcatc ccgtcaggcc ccctcaaagc cgagatcgca cagagacttg aagatgtctt     120
tgcagggaag aacaccgatc ttgaggttct catggaatgg ctaaagacaa gaccaatcct     180
gtcacctctg actaagggga ttttaggatt tgtgttcacg ctcaccgtgc ccagtgagcg     240
aggactgcag cgtagacgct ttgtccaaaa tgcccttaat gggacgggg atccaaataa      300
catggacaaa gcagttaaac tgtataggaa gctcaagagg gagataacat tccatggggc     360
caaagaaatc tcactcagtt attctgctgg tgcacttgcc agttgtatgg gcctcatata     420
caacaggatg ggggctgtga ccactgaagt ggcatttggc ctggtatgtg caacctgtga     480
acagattgct gactcccagc atcggtctca taggcaaatg gtgacaacaa ccaatccact     540
aatcagacat gagaacagaa tggttttagc cagcactaca gctaaggcta tggagcaaat     600
ggctggatcg agtgagcaag cagcagaggc catggaggtt gctagtcagg ctagacaaat     660
ggtgcaagcg atgagaacca ttgggactca tcctagctcc agtgctggtc tgaaaaatga     720
tcttcttgaa aatttgcagg cctatcagaa acgaatgggg gtgcagatgc aacggttcaa     780
gtgatcctct cactattgcc gcaaatatca ttgggatctt gcacttgaca ttgtggattc     840
ttgatcgtct ttttttcaaa tgcatttacc gtcgctttaa atacgactg aaaggagggc      900
cttctacgga aggagtgcca agtctatga gggaagaata tcgaaggaa cagcagagtg       960
ctgtggatgc tgacgatggt cattttgtca gcatagagct ggagtaaaaa actaccttgt    1020
ttctact                                                              1027
```

<210> SEQ ID NO 6
<211> LENGTH: 890
<212> TYPE: DNA
<213> ORGANISM: Influenza A

<400> SEQUENCE: 6

```
agcaaaagca gggtgacaaa aacataatgg atccaaacac tgtgtcaagc tttcaggtag      60
attgctttct ttggcatgtc cgcaaacgag ttgcagacca agaactaggc gatgccccat     120
tccttgatcg gcttcgccga gatcagaaat ccctaagagg aaggggcagt actctcggtc     180
tggacatcaa gacagccaca cgtgctggaa agcagatagt ggagcggatt ctgaaagaag     240
aatccgatga ggcacttaaa atgaccatgg cctctgtacc tgcgtcgcgt tacctaactg     300
acatgactct tgaggaaatg tcaagggact ggtccatgct catacccaag cagaaagtgg     360
caggccctct ttgtatcaga atggaccagg cgatcatgga taagaacatc atactgaaag     420
cgaacttcag tgtgattttt gaccggctgg agactctaat attgctaagg ctttccaccg     480
aagagggagc aattgttggc gaaatttcac cattgccttc tcttccagga catactgctg     540
aggatgtcaa aaatgcagtt ggagtcctca tcggaggact tgaatggaat gataacacag     600
ttcgagtctc tgaaactcta cagagattcg cttggagaag cagtaatgag aatgggagac     660
ctccactcac tccaaaacag aaacgagaaa tggcgggaac aattaggtca gaagtttgaa     720
gaaataagat ggttgattga agaagtgaga cacaaactga gataacaga gaatagttt      780
gagcaaataa catttatgca agccttacat ctattgcttg aagtggagca agagataaga     840
actttctcgt ttcagcttat ttagtactaa aaaacaccct tgtttctact                 890
```

<210> SEQ ID NO 7

```
<211> LENGTH: 1775
<212> TYPE: DNA
<213> ORGANISM: Influenza A

<400> SEQUENCE: 7
agcaaaagca ggggaaaata aaaacaacca aaatgaaggc aaacctactg gtcctgttat     60
gtgcacttgc agctgcagat gcagacacaa tatgtatagg ctaccatgcg aacaattcaa    120
ccgacactgt tgacacagta ctcgagaaga atgtgacagt gacacactct gttaacctgc    180
tcgaagacag ccacaacgga aaactatgta gattaaaagg aatagcccca ctacaattgg    240
ggaaatgtaa catcgccgga tggctcttgg gaaacccaga atgcgaccca ctgcttccag    300
tgagatcatg gtcctacatt gtagaaacac caaactctga gaatggaata tgttatccag    360
gagatttcat cgactatgag gagctgaggg agcaattgag ctcagtgtca tcattcgaaa    420
gattcgaaat atttcccaaa gaaagctcat ggcccaacca caacacaaac ggagtaacgg    480
cagcatgctc ccatgagggg aaaagcagtt tttacagaaa tttgctatgg ctgacggaga    540
aggagggctc atacccaaag ctgaaaaatt cttatgtgaa caaaaaaggg aaagaagtcc    600
ttgtactgtg ggtattcat cacccgccta acagtaagga acaacagaat ctctatcaga    660
atgaaaatgc ttatgtctct gtagtgactt caaattataa caggagattt accccggaaa    720
tagcagaaag acccaaagta agagatcaag ctgggaggat gaactattac tggaccttgc    780
taaaacccgg agacacaata atatttgagg caaatggaaa tctaatagca ccaatgtatg    840
ctttcgcact gagtagaggc tttgggtccg gcatcatcac ctcaaacgca tcaatgcatg    900
agtgtaacac gaagtgtcaa acacccctgg gagctataaa cagcagtctc ccttaccaga    960
atatacaccc agtcacaata ggagagtgcc caaaatacgt caggagtgcc aaattgagga   1020
tggttacagg actaaggaac attccgtcca ttcaatccag aggtctattt ggagccattg   1080
ccggttttat tgaagggggga tggactggaa tgatagatgg atggtatggt tatcatcatc   1140
agaatgaaca gggatcaggc tatgcagcgg atcaaaaaag cacacaaaat gccattaacg   1200
ggattacaaa caaggtgaac actgttatcg agaaaatgaa cattcaattc acagctgtgg   1260
gtaaagaatt caacaaatta gaaaaaagga tggaaaattt aaataaaaaa gttgatgatg   1320
gatttctgga catttggaca tataatgcag aattgttagt tctactggaa aatgaaagga   1380
ctctggattt ccatgactca aatgtgaaga atctgtatga gaaagtaaaa agccaattaa   1440
agaataatgc caaagaaatc ggaaatggat gttttgagtt ctaccacaag tgtgacaatg   1500
aatgcatgga aagtgtaaga aatgggactt atgattatcc caaatattca gaagagtcaa   1560
agttgaacag ggaaaaggta gatggagtga aattggaatc aatggggatc tatcagattc   1620
tggcgatcta ctcaactgtc gccagttcac tggtgctttt ggtctccctg gggggcaatca  1680 gtttctggat gtgttctaat ggatctttgc agtgcagaat atgcatctga gattagaatt   1740
tcagagatat gaggaaaaac acccttgttt ctact                              1775

<210> SEQ ID NO 8
<211> LENGTH: 1413
<212> TYPE: DNA
<213> ORGANISM: Influenza A

<400> SEQUENCE: 8
agcaaaagca ggggtttaaa atgaatccaa atcagaaaat aataaccatt ggatcaatct     60
gtctggtagt cggactaatt agcctaatat tgcaaatagg gaatataatc tcaatatgga    120
ttagccattc aattcaaact ggaagtcaaa accatactgg aatatgcaac caaaacatca    180
```

```
ttacctataa aaatagcacc tgggtaaagg acacaacttc agtgatatta accggcaatt      240
catctctttg tcccatccgt gggtgggcta tatacagcaa agacaatagc ataagaattg      300
gttccaaagg agacgttttt gtcataagag agcccttat ttcatgttct cacttggaat      360
```

(Note: line 360 reads: gttccaaagg agacgttttt gtcataagag agcccttat ttcatgttct cacttggaat)

```
gcaggacctt ttttctgacc caaggtgcct tactgaatga caagcattca agtgggactg      420
ttaaggacag aagcccttat agggccttaa tgagctgccc tgtcggtgaa gctccgtccc      480
cgtacaattc aagatttgaa tcggttgctt ggtcagcaag tgcatgtcat gatggcatgg      540
gctggctaac aatcggaatt tcaggtccag ataatggagc agtggctgta ttaaaataca      600
acggcataat aactgaaacc ataaaaagtt ggaggaagaa aatattgagg acacaagagt      660
ctgaatgtgc ctgtgtaaat ggttcatgtt ttactataat gactgatggc ccgagtgatg      720
ggctggcctc gtacaaaatt ttcaagatcg aaaaggggaa ggttactaaa tcaatagagt      780
tgaatgcacc taattctcac tatgaggaat gttcctgtta ccctgatacc ggcaaagtga      840
tgtgtgtgtg cagagacaat tggcatggtt cgaaccggcc atgggtgtct ttcgatcaaa      900
acctggatta tcaaatagga tacatctgca gtggggtttt cggtgacaac ccgcgtcccg      960
aagatggaac aggcagctgt ggtccagtgt atgttgatgg agcaaacgga gtaaagggat      1020
tttcatatag gtatggtaat ggtgtttgga taggaaggac caaaagtcac agttccagac      1080
atgggtttga gatgatttgg gatcctaatg gatggacaga gactgatagt aagttctctg      1140
tgaggcaaga tgttgtggca atgactgatt ggtcagggta tagcggaagt ttcgttcaac      1200
atcctgagct gacagggcta gactgtatga ggccgtgctt ctgggttgaa ttaatcaggg      1260
gacgacctaa agaaaaaaca atctggacta gtgcgagcag catttctttt tgtggcgtga      1320
atagtgatac tgtagattgg tcttggccag acggtgctga gttgccattc agcattgaca      1380
agtagtctgt tcaaaaaact ccttgtttct act                                  1413
```

<210> SEQ ID NO 9
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 9

```
cacacacggt ctccgggagc gaaagcaggc a                                    31
```

<210> SEQ ID NO 10
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 10

```
ccaggacact gaaatttctt tcac                                            24
```

<210> SEQ ID NO 11
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 11

```
cacacaggtc tcctattagt agaaacaagg cattt                                35
```

<210> SEQ ID NO 12
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 12
cacacaggtc tccgggagcg aaagcaggtc                                     30

<210> SEQ ID NO 13
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 13
cacacacgtc tccatcatac aatcctcttg                                     30

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 14
ctcctctgat ggtggcatac                                                20

<210> SEQ ID NO 15
<211> LENGTH: 36
<212> TYPE: DNA
<213> ORGANISM: Artificial Sequence
<220> FEATURE:
<223> OTHER INFORMATION: A synthetic oligonucleotide

<400> SEQUENCE: 15
cacacaggtc tcctattagt agaaacaagg tcgttt                              36

<210> SEQ ID NO 16
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 16
cacacacgtc tccgggagcg aaagcaggta c                                   31

<210> SEQ ID NO 17
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 17
cacacacgtc tcctattagt agaaacaagg tactt                               35

<210> SEQ ID NO 18
<211> LENGTH: 30
<212> TYPE: DNA
<213> ORGANISM: Artificial Sequence
<220> FEATURE:
<223> OTHER INFORMATION: A synthetic oligonucleotide

```
-continued

<400> SEQUENCE: 18
cacacacgtc tccgggagca aaagcagggg                                    30

<210> SEQ ID NO 19
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 19
cacacacgtc tcctattagt agaaacaagg gtgtttt                            37

<210> SEQ ID NO 20
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 20
cacacacgtc tccgggagca aaagcagggt a                                  31

<210> SEQ ID NO 21
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 21
cacacacgtc tcctattagt agaaacaagg gtattttt                           38

<210> SEQ ID NO 22
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 22
cacacaggtc tccgggagca aaagcaggag t                                  31

<210> SEQ ID NO 23
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 23
cacacaggtc tggtattagt agaaacaagg agtttttt                           38

<210> SEQ ID NO 24
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 24
cacacacgtc tccgggagca aaagcaggta g                                  31

<210> SEQ ID NO 25
```

-continued

```
<211> LENGTH: 38
<212> TYPE: DNA
<213> ORGANISM: Artificial Sequence
<220> FEATURE:
<223> OTHER INFORMATION: A synthetic oligonucleotide

<400> SEQUENCE: 25
cacacacgtc tcctattagt agaaacaagg tagttttt                              38

<210> SEQ ID NO 26
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 26
cacacacgtc tccgggagca aaagcagggt g                                     31

<210> SEQ ID NO 27
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 27
cacacacgtc tcctattagt agaaacaagg gtgtttt                               37

<210> SEQ ID NO 28
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 28
gggtttgtat ttgtgtgtca cc                                               22

<210> SEQ ID NO 29
<211> LENGTH: 8
<212> TYPE: PRT
<213> ORGANISM: Influenza A

<400> SEQUENCE: 29

Arg Glu Arg Arg Arg Lys Lys Arg
 1               5

<210> SEQ ID NO 30
<211> LENGTH: 4
<212> TYPE: PRT
<213> ORGANISM: Artificial Sequence
<220> FEATURE:
<223> OTHER INFORMATION: A synthetic peptide

<400> SEQUENCE: 30

Thr Glu Thr Arg
 1

<210> SEQ ID NO 31
<211> LENGTH: 4
<212> TYPE: PRT
<213> ORGANISM: Artificial Sequence
<220> FEATURE:
<223> OTHER INFORMATION: A synthetic peptide

<400> SEQUENCE: 31
```

Arg Glu Thr Arg
 1

<210> SEQ ID NO 32
<211> LENGTH: 20
<212> TYPE: PRT
<213> ORGANISM: Artificial Sequence
<220> FEATURE:
<223> OTHER INFORMATION: A synthetic peptide

<400> SEQUENCE: 32

Cys Asn Gln Ser Ile Ile Thr Tyr Glu Asn Asn Thr Trp Val Asn Gln
 1               5                  10                  15

Thr Tyr Val Asn
            20

<210> SEQ ID NO 33
<211> LENGTH: 2341
<212> TYPE: DNA
<213> ORGANISM: Influenza A

<400> SEQUENCE: 33
agcgaaagca ggtcaattat attcaatatg gaaagaataa agaactaag aaatctaatg         60 tcgcagtctc gcacccgcga gatactcaca aaaaccaccg tggaccatat ggccataatc       120
aagaagtaca catcaggaag acaggagaag aacccagcac ttaggatgaa atggatgatg       180
gcaatgaaat atccaattac agcagacaag aggataacgg aaatgattcc tgagagaaat       240
gagcaaggac aaactttatg gagtaaaatg aatgatgccg gatcagaccg agtgatggta       300
tcacctctgg ctgtgacatg gtggaatagg aatggaccaa tgacaaatac agttcattat       360
ccaaaaatct acaaaactta ttttgaaaga gtcgaaaggc taaagcatgg aacctttggc       420
cctgtccatt ttagaaacca agtcaaaata cgtcggagag ttgacataaa tcctggtcat       480
gcagatctca gtgccaagga ggcacaggat gtaatcatgg aagttgtttt ccctaacgaa       540
gtgggagcca ggatactaac atcggaatcg caactaacga taaccaaaga gaagaaagaa       600
gaactccagg attgcaaaat ttctcctttg atggttgcat acatgttgga gagaactg         660 gtccgcaaaa cgagattcct cccagtggct ggtggaacaa gcagtgtgta cattgaagtg       720
ttgcatttga ctcaaggaac atgctgggaa cagatgtata ctccaggagg gaagtgaag        780 aatgatgatg ttgatcaaag cttgattatt gctgctagga acatagtgag aagagctgca       840
gtatcagcag acccactagc atctttattg gagatgtgcc acagcacaca gattggtgga       900
attaggatgg tagacatcct taagcagaac ccaacagaag agcaagccgt ggatatatgc       960
aaggctgcaa tgggactgag aattagctca tccttcagtt tggtggatt cacatttaag      1020 agaacaagcg gatcatcagt caagagagag gaagaggtgc ttacgggcaa tcttcaaaca      1080
ttgaagataa gagtgcatga gggatctgaa gagttcacaa tggttgggag aagagcaaca      1140
gccatactca gaaaagcaac caggagattg attcagctga tagtgagtgg gagagacgaa      1200
cagtcgattg ccgaagcaat aattgtggcc atggtatttt cacaagagga ttgtatgata      1260
aaagcagtta gaggtgatct gaatttcgtc aataggcga atcagcgact gaatcctatg      1320
catcaacttt taagacattt tcagaaggat gcgaaagtgc ttttttcaaaa ttggggagtt      1380 gaacctatcg acaatgtgat gggaatgatt gggatattgc ccgacatgac tccaagcatc      1440
gagatgtcaa tgagaggagt gagaatcagc aaaatgggtg tagatgagta ctccagcacg      1500
gagagggtag tggtgagcat tgaccggttc ttgagagtca gggaccaacg aggaaatgta      1560

```
ctactgtctc ccgaggaggt cagtgaaaca cagggaacag agaaactgac aataaacttac    1620 tcatcgtcaa tgatgtggga gattaatggt cctgaatcag tgttggtcaa tacctatcaa    1680
tggatcatca gaaactggga aactgttaaa attcagtggt cccagaaccc tacaatgcta    1740
tacaataaaa tggaatttga accatttcag tctttagtac ctaaggccat tagaggccaa    1800
tacagtgggt ttgtaagaac tctgttccaa caaatgaggg atgtgcttgg gacatttgat    1860
accgcacaga taataaaact tcttcccttc gcagccgctc caccaaagca agtagaatg     1920 cagttctcct catttactgt gaatgtgagg ggatcaggaa tgagaatact tgtaaggggc    1980
aattctcctg tattcaacta caacaaggcc acgaagagac tcacagttct cggaaaggat    2040
gctggcactt taaccgaaga cccagatgaa ggcacagctg gagtggagtc cgctgttctg    2100
aggggattcc tcattctggg caaagaagac aggagatatg gccagcatt aagcatcaat     2160 gaactgagca accttgcgaa aggagagaag gctaatgtgc taattgggca aggagacgtg    2220
gtgttggtaa tgaaacgaaa acgggactct agcatactta ctgacagcca gacagcgacc    2280
aaaagaattc ggatggccat caattagtgt cgaatagttt aaaaacgacc ttgtttctac    2340
t                                                                    2341

<210> SEQ ID NO 34
<211> LENGTH: 2341
<212> TYPE: DNA
<213> ORGANISM: Influenza A

<400> SEQUENCE: 34
agcgaaagca ggcaaaccat ttgaatggat gtcaatccga ccttactttt cttaaaagtg      60
ccagcacaaa atgctataag cacaactttc ccttataccg agaccctcc ttacagccat     120 gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaagcaatg    300
gctttccttg aggaatccca tcctggtatt tttgaaaact cgtgtattga acgatggag     360 gttgttcagc aaacacgagt agacaagctg acacaaggcc gacagaccta tgactggact    420
ttaaatagaa accagcctgc tgcaacagca ttggccaaca caatagaagt gttcagatca    480
aatggcctca cggccaatga gtcaggaagg ctcatagact ccttaagga gtaatggag      540 tcaatgaaaa agaagaaat ggggatcaca actcattttc agagaaagag acgggtgaga     600
gacaatatga ctaagaaaat gataacacag agaacaatag gtaaaggaa acagagattg     660 aacaaaaggg gttatctaat tagagcattg accctgaaca caatgaccaa agatgctgag    720
agagggaagc taaacggag agcaattgca accccaggga tgcaaataag ggggtttgta    780
tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaactttc tttcaccatc actggagata caccaaatg gaacgaaaat    960 cagaatcctc ggatgttttt ggccatgatc acatatatga ccagaaatca gcccgaatgg   1020
ttcagaaatg ttcaagtat tgctccaata atgttctcaa acaaaatggc gagactggga    1080 aagggtata tgtttgagag caagagtatg aaacttagaa ctcaaatacc tgcagaaatg    1140
ctagcaagca ttgatttgaa atatttcaat gattcaacaa gaagaagat tgaaaaaatc    1200 cgaccgctct aatagagggg gactgcatca ttgagccctg gaatgatgat gggcatgttc   1260
```

```
aatatgttaa gcactgtatt aggcgtctcc atcctgaatc ttggacaaaa gagatacacc    1320
aagactactt actggtggga tggtcttcaa tcctctgacg attttgctct gattgtgaat    1380
gcacccaatc atgaagggat tcaagccgga gtcgacaggt tttatcgaac ctgtaagcta    1440
cttggaatca atatgagcaa gaaaaagtct tacataaaca gaacaggtac atttgaattc    1500
acaagttttt tctatcgtta tgggtttgtt gccaatttca gcatggagct tcccagtttt    1560
ggggtgtctg ggatcaacga gtcagcggac atgagtattg gagttactgt catcaaaaac    1620
aatatgataa acaatgatct tggtccagca acagctcaaa tggcccttca gttgttcatc    1680
aaagattaca ggtacacgta ccgatgccat agaggtgaca cacaaataca aacccgaaga    1740
tcatttgaaa taagaaact gtgggagcaa acccgttcca aagctggact gctggtctcc    1800
gacggaggcc caaatttata caacattaga atctccaca ttcctgaagt ctgcctaaaa    1860
tgggaattga tggatgagga ttaccagggg cgtttatgca acccactgaa cccatttgtc    1920
agccataaag aaattgaatc aatgaacaat gcagtgatga tgccagcaca tggtccagcc    1980
aaaaacatgg agtatgatgc tgttgcaaca acacactcct ggatcccaa aagaaatcga    2040 tccatcttga atacaagtca agaggagta cttgaagatg aacaaatgta ccaaaggtgc    2100
tgcaatttat ttgaaaaatt cttccccagc agttcataca aagaccagt cgggatatcc    2160 agtatggtgg aggctatggt ttccagagcc cgaattgatg cacggattga tttcgaatct    2220
ggaaggataa agaagaaga gttcactgag atcatgaaga tctgttccac cattgaagag    2280
ctcagacggc aaaaatagtg aatttagctt gtccttcatg aaaaaatgcc ttgtttctac    2340
t                                                                   2341

<210> SEQ ID NO 35
<211> LENGTH: 2233
<212> TYPE: DNA
<213> ORGANISM: Influenza A

<400> SEQUENCE: 35
agcgaaagca ggtactgatt caaaatggaa gattttgtgc gacaatgctt caatccgatg     60
attgtcgagc ttgcggaaaa acaatgaaa gagtatgggg aggacctgaa atcgaaaca    120 aacaaatttg cagcaatatg cactcacttg gaagtatgct tcatgtattc agatttccac    180
ttcatcaatg agcaaggcga gtcaataatc gtagaacttg gtgatcctaa tgcacttttg    240
aagcacagat ttgaaataat cgagggaaga gatcgcacaa tggcctggac agtagtaaac    300
agtatttgca acactacagg ggctgagaaa ccaaagtttc taccagattt gtatgattac    360
aaggaaaata gattcatcga aattggagta acaaggagag aagttcacat atactatctg    420
gaaaaggcca ataaaattaa atctgagaaa acacacatcc atttttctc gttcactggg    480 gaagaaatgg ccacaagggc cgactacact ctcgatgaag aaagcagggc taggatcaaa    540
accaggctat tcaccataag acaagaaatg gccagcagag gcctctggga ttcctttcgt    600
cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc tttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaaaggg aataaatcca   1020
```

```
aattatcttc tgtcatggaa gcaagtactg gcagaactgc aggacattga gaatgaggag    1080
aaaattccaa agactaaaaa tatgaaaaaa acaagtcagc taaagtgggc acttggtgag    1140
aacatggcac cagaaaaggt agactttgac gactgtaaag atgtaggtga tttgaagcaa    1200
tatgatagtg atgaaccaga attgaggtcg cttgcaagtt ggattcagaa tgagttcaac    1260
aaggcatgcg aactgacaga ttcaagctgg atagagcttg atgagattgg agaagatgtg    1320
gctccaattg aacacattgc aagcatgaga aggaattatt tcacatcaga ggtgtctcac    1380
tgcagagcca cagaatacat aatgaagggg gtgtacatca atactgcctt acttaatgca    1440
tcttgtgcag caatggatga tttccaatta attccaatga taagcaagtg tagaactaag    1500
gagggaaggc gaaagaccaa cttgtatggt tcatcataa aaggaagatc ccacttaagg    1560
aatgacaccg acgtggtaaa ctttgtgagc atggagtttt ctctcactga cccaagactt    1620
gaaccacaca atgggagaa gtactgtgtt cttgagatag agatatgct tctaagaagt    1680 gccataggcc aggtttcaag gcccatgttc ttgtatgtga ggacaaatgg aacctcaaaa    1740
attaaaatga atggggaat ggagatgagg cgttgtctcc tccagtcact tcaacaaatt    1800
gagagtatga ttgaagctga gtcctctgtc aaagagaaag acatgaccaa agagttcttt    1860
gagaacaaat cagaaacatg gcccattgga gagtctccca aaggagtgga ggaaagttcc    1920
attgggaagg tctgcaggac tttattagca aagtcggtat ttaacagctt gtatgcatct    1980
ccacaactag aaggattttc agctgaatca agaaaactgc ttcttatcgt tcaggctctt    2040
agggacaatc tggaacctgg gacctttgat cttggggggc tatatgaagc aattgaggag    2100
tgcctaatta atgatccctg ggttttgctt aatgcttctt ggttcaactc cttccttaca    2160
catgcattga gttagttgtg gcagtgctac tatttgctat ccatactgtc caaaaaagta    2220 ccttgttttct act                                                    2233

<210> SEQ ID NO 36
<211> LENGTH: 1565
<212> TYPE: DNA
<213> ORGANISM: Influenza A

<400> SEQUENCE: 36
agcaaaagca gggtagataa tcactcactg agtgacatca aaatcatggc gtcccaaggc    60
accaaacggt cttacgaaca gatggagact gatggagaac gccagaatgc cactgaaatc    120
agagcatccg tcggaaaaat gattggtgga attggacgat tctacatcca aatgtgcaca    180
gaacttaaac tcagtgatta tgagggacgg ttgatccaaa acagcttaac aatagagaga    240
atggtgctct ctgcttttga cgaaaggaga aataaatacc tggaagaaca tcccagtgcg    300
gggaaagatc ctaagaaaac tggaggacct atatacagaa gagtaaacgg aaagtggatg    360
agagaactca tcctttatga caaagaagaa ataaggcgaa tctggcgcca agctaataat    420
ggtgacgatg caacggctgg tctgactcac atgatgatct ggcattccaa tttgaatgat    480
gcaacttatc agaggacaag ggctcttgtt cgcaccggaa tggatcccag gatgtgctct    540
ctgatgcaag gttcaactct ccctaggagg tctggagccg caggtgctgc agtcaaagga    600
gttggaacaa tggtgatgga attggtcagg atgatcaaac gtgggatcaa tgatcggaac    660
ttctggaggg gtgagaatgg acgaaaaaca agaattgctt atgaaagaat gtgcaacatt    720
ctcaaaggga aatttcaaac tgctgcacaa aaagcaatga tggatcaagt gagagagagc    780
cggaacccag ggaatgctga gttcgaagat ctcactttc tagcacggtc tgcactcata    840
```

```
ttgagagggt cggttgctca caagtcctgc ctgcctgcct gtgtgtatgg acctgccgta      900
gccagtgggt acgactttga aagagaggga tactctctag tcggaataga cccctttcaga    960
ctgcttcaaa acagccaagt gtacagccta atcagaccaa atgagaatcc agcacacaag    1020
agtcaactgg tgtggatggc atgccattct gccgcatttg aagatctaag agtattgagc    1080
ttcatcaaag ggacgaaggt ggtcccaaga gggaagcttt ccactagagg agttcaaatt    1140
gcttccaatg aaaatatgga gactatgaa tcaagtacac ttgaactgag aagcaggtac     1200
tgggccataa ggaccagaag tggaggaaac accaatcaac agagggcatc tgcgggccaa    1260
atcagcatac aacctacgtt ctcagtacag agaaatctcc cttttgacag aacaaccgtt    1320
atggcagcat tcactgggaa tacagagggg agaacatctg acatgaggac cgaaatcata    1380
aggatgatgg aaagtgcaag accagaagat gtgtctttcc aggggcgggg agtcttcgag    1440
ctctcggacg aaaaggcagc gagcccgatc gtgccttcct ttgacatgag taatgaagga    1500
tcttatttct tcggagacaa tgcagaggag tacgacaatt aaagaaaaat accccttgttt  1560
ctact                                                                1565

<210> SEQ ID NO 37
<211> LENGTH: 1027
<212> TYPE: DNA
<213> ORGANISM: Influenza A

<400> SEQUENCE: 37
agcaaaagca ggtagatatt gaaagatgag tcttctaacc gaggtcgaaa cgtacgttct      60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaacccact    540
aatcagacat gagaacagaa tggttttagc cagcactaca gctaaggcta tggagcaaat    600
ggctggatcg agtgagcaag cagcagaggc catggaggtt gctagtcagg ctaggcaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgatcctct cgctattgcc gcaaatatca ttgggatctt gcacttgata ttgtggattc    840
ttgatcgtct ttttttcaaa tgcatttacc gtcgctttaa atacggactg aaaggagggc    900
cttctacgga aggagtgcca aagtctatga gggaagaata tcgaaaggaa cagcagagtg    960
ctgtggatgc tgacgatggt catttgtca gcatagagct ggagtaaaaa actaccttgt  1020
ttctact                                                             1027

<210> SEQ ID NO 38
<211> LENGTH: 890
<212> TYPE: DNA
<213> ORGANISM: Influenza A

<400> SEQUENCE: 38
agcaaaagca gggtgacaaa gacataatgg atccaaacac tgtgtcaagc tttcaggtag     60
```

```
attgctttct ttggcatgtc cgcaaacgag ttgcagacca agaactaggt gatgccccat    120
tccttgatcg gcttcgccga gatcagaaat ccctaagagg aaggggcagc actcttggtc    180
tggacatcga gacagccaca cgtgctggaa agcagatagt ggagcggatt ctgaaagaag    240
aatccgatga ggcacttaaa atgaccatgg cctctgtacc tgcgtcgcgt tacctaaccg    300
acatgactct tgaggaaatg tcaagggaat ggtccatgct catacccaag cagaaagtgg    360
caggccctct ttgtatcaga atggaccagg cgatcatgga taaaaacatc atactgaaag    420
cgaacttcag tgtgattttt gaccggctgg agactctaat attgctaagg gctttcaccg    480
aagagggagc aattgttggc gaaatttcac cattgccttc tcttccagga catactgctg    540
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga aggtaacaga gaatagtttt    780
gagcaaataa catttatgca agccttacat ctattgcttg aagtggagca agagataaga    840
actttctcat ttcagcttat ttaataataa aaaacaccct tgtttctact                890
```

UNITED STATES PATENT AND TRADEMARK OFFICE
CERTIFICATE OF CORRECTION

PATENT NO. : 9,926,535 B2
APPLICATION NO. : 15/000851
DATED : March 27, 2018
INVENTOR(S) : Kawaoka et al.

Page 1 of 2

It is certified that error appears in the above-identified patent and that said Letters Patent is hereby corrected as shown below:

On the Title Page

In Column 2, under "Other Publications", Line 1, delete "Respojnse" and insert --Response-- therefor In Column 2, under "Other Publications", Line 8, delete "Examinsers" and insert --Examiners-- therefor On page 2, in Column 1, under "Foreign Patent Documents", Line 6, delete "171931 A" and insert --171831 A-- therefor On page 2, in Column 2, under "Foreign Patent Documents", Line 2, delete "2009-532352 a" and insert --2009-532352 A-- therefor On page 2, in Column 2, under "Other Publications", Line 11, delete "NCCBI" and insert --NCBI-- therefor On page 3, in Column 1, under "Other Publications", Line 1, delete "Respons" and insert --Response-- therefor On page 4, in Column 1, under "Other Publications", Lines 7-8, delete "Hemaggulutinin" and insert --Hemagglutinin-- therefor On page 4, in Column 1, under "Other Publications", Line 24, delete "millenium." and insert --millennium.-- therefor On page 5, in Column 1, under "Other Publications", Line 4, delete "Dec. 20, 2010"," and insert --Dec. 10, 2010",-- therefor On page 5, in Column 2, under "Other Publications", Line 41, delete "200480021259:9" and insert --200480021259.9-- therefor Signed and Sealed this
Second Day of June, 2020

Andrei Iancu
*Director of the United States Patent and Trademark Office*

CERTIFICATE OF CORRECTION (continued)
U.S. Pat. No. 9,926,535 B2

On page 6, in Column 2, under "Other Publications", Line 25, delete "Dec. 7," and insert --Dec. 17,-- therefor On page 7, in Column 2, under "Other Publications", Line 10, delete ""international" and insert --"International-- therefor On page 7, in Column 2, under "Other Publications", Line 69, delete "2006-533439,Office" and insert --2006-533439, Office-- therefor On page 7, in Column 2, under "Other Publications", Line 71, delete "2006-533439;" and insert --2006-533439,-- therefor On page 8, in Column 1, under "Other Publications", Line 8, delete "2011-111048." and insert --2011-111048,-- therefor On page 8, in Column 1, under "Other Publications", Line 24, delete "2006-513125,Final" and insert --2006-513125, Final-- therefor On page 8, in Column 2, under "Other Publications", Line 20, delete "542935" and insert --542935,-- therefor On page 8, in Column 2, under "Other Publications", Line 28, delete "Examinatiom" and insert --Examination-- therefor On page 9, in Column 1, under "Other Publications", Line 49, delete "Essentiial" and insert --Essential-- therefor On page 10, in Column 2, under "Other Publications", Line 25, delete "(HSN1)" and insert --(H5N1)-- therefor On page 11, in Column 1, under "Other Publications", Line 21, delete "Choramphenicol" and insert --Chloramphenicol-- therefor On page 12, in Column 2, under "Other Publications", Line 29, delete "Stomatitits" and insert --Stomatitis-- therefor In the Claims In Column 75, Line 11, in Claim 12, delete "embyronated" and insert --embryonated-- therefor In Column 75, Line 20, in Claim 13, after "recombinant", insert --influenza--

In Column 76, Line 8, in Claim 18, after "recombinant", insert --influenza--

In Column 76, Line 11, in Claim 19, after "recombinant", insert --influenza--